(12) United States Patent
Marino et al.

(10) Patent No.: US 8,124,725 B2
(45) Date of Patent: Feb. 28, 2012

(54) PDGF-Rβ BINDERS

(75) Inventors: Michael Ernest Marino, Clifton Park, NY (US); Faisal Ahmed Syud, Clifton Park, NY (US); Paul Schaffer, Clifton Park, NY (US); Brian Duh-Lan Lee, Rexford, NY (US); Rong Zhang, Niskayuna, NY (US); Malin Lindborg, Hagersten (SE); Elin Gunneriusson, Saltsjobaden (SE); Christopher Lendel, Farsta (SE)

(73) Assignee: General Electric Company, Niskayuna, NY (US)

( * ) Notice: Subject to any disclaimer, the term of this patent is extended or adjusted under 35 U.S.C. 154(b) by 643 days.

(21) Appl. No.: 12/336,780

(22) Filed: Dec. 17, 2008

(65) Prior Publication Data

US 2009/0191124 A1 Jul. 30, 2009

Related U.S. Application Data

(63) Continuation-in-part of application No. 12/002,972, filed on Dec. 19, 2007.

(51) Int. Cl.
| | |
|---|---|
| A61K 38/00 | (2006.01) |
| A61K 49/00 | (2006.01) |
| A61K 38/18 | (2006.01) |
| A61K 51/00 | (2006.01) |
| C07K 5/00 | (2006.01) |
| C07K 7/00 | (2006.01) |
| C07K 16/00 | (2006.01) |
| C07K 17/00 | (2006.01) |
| C07K 14/50 | (2006.01) |

(52) U.S. Cl. ........ 530/324; 424/9.1; 424/1.69; 530/300; 514/8.2

(58) Field of Classification Search .................. None
See application file for complete search history.

(56) References Cited

U.S. PATENT DOCUMENTS

| 6,020,163 | A | 2/2000 | Conklin |
| 6,673,559 | B1 | 1/2004 | Tsarfaty et al. |
| 7,118,915 | B2 | 10/2006 | Vogt et al. |
| 7,250,297 | B1 | 7/2007 | Beste et al. |
| 2002/0052488 | A1 | 5/2002 | Boone et al. |
| 2006/0177831 | A1 | 8/2006 | Stemmer et al. |

FOREIGN PATENT DOCUMENTS

| EP | 0329185 | 4/1994 |
| WO | 2009041062 | 4/2009 |
| WO | 2009041643 | 4/2009 |

OTHER PUBLICATIONS

PCT Search Report, PCT/EP2008/067774, Mar. 6, 2009.
J. M. Jeong et al.,"Application of High Affinity Binding Concept to Radiolabel Avidin with Tc-99m Labeled biotin and the Effect of pI on Biodistribution," Nuclear Medicine and Biology, Elsevier Science Ltd., vol. 21, No. 7, 1994, pp. 935-940.
S. F. Rosebrough et al., Biochemical Modification of Streptavidin and Avidin: In Vitro and In Vivo Analysis, The Journal of Nuclear Medicine, vol. 37, No. 8, Aug. 1996, pp. 1380-1384.
F.J. Burczynski et al., "Hepatocyte [3H]-palmitate uptake: effect of albumin surface charge modification," Canadian Journal of Physiology and Pharmacology, NRC Research Press, ISSN: 008-4212, Oct. 1, 2001, pp. 868-875.
WO2009041062 Abstract, Apr. 2, 2009.
WO2009041643 Abstract, Apr. 2, 2009.
A. Sierra, "Lipocalins as a Scaffold," Biochimica et Biophysics Acta 1482, 2000, pp. 337-350.
J. V. Mercader et al., "Generation of anticalins with specificity for a nonsymmetric phthalic acid ester,"Analytical Biochemistry, vol. 308, pp. 269-277.
I.P. Korndorfer et al., "Structural Mechanism of Specific Ligand Recognition by a Lipocalin Tailored for the Complexation of Digoxigenin," Science Direct, Journal Molecular Biology, vol. 330, 2003, pp. 385-396.
I. P. Korndorfer et al., "Crystallographic Analysis of an "Anticalin" with Tailored Specificity for Fluorescein Reveals High Structural Plasticity of the Lipocalin Loop Region," Proteins: Structure, function and Bioinformatics, vol. 53, 2003, pp. 121-129.

*Primary Examiner* — Maury Audet
(74) *Attorney, Agent, or Firm* — Jenifer E. Haeckl

(57) ABSTRACT

Provided herein are PDGF-Rβ imaging agents that are polypeptides labeled with a signal generator (e.g., paramagnetic label, a radionuclide, or a fluorophore), wherein the imaging agents bind specifically to PDGFR-β. Also provided are in vivo imaging methods using the imaging agents.

26 Claims, 27 Drawing Sheets

PDGF-Rβ BINDERS

CROSS REFERENCE TO RELATED APPLICATIONS

This application claims priority to U.S. patent application Ser. No. 12/002,972, entitled "Biokinetics of Fast-clearing Polypeptides", filed Dec. 19, 2007, which is incorporated herein by reference.

FIELD

The invention relates generally to agents that bind PDGF-Rβ. The invention more specifically relates to labeled agents that bind to PDGF-Rβ and detection methods using such agents.

BACKGROUND

PDGF-Rβ is a receptor tyrosine kinase implicated in fibrotic and oncologic disease, and represents a potentially valuable molecular imaging target. The ability to qualitatively or quantitatively visualize PDGF-Rβ, either in vivo or in vitro, confers upon researchers and clinicians important diagnostic and treatment tools. For example, the ability to visually identify liver-associated diseases, such as liver fibrosis, cirrhosis, or abnormal liver function. The ability to measure expression patterns of PDGF-Rβ in vivo in patients with such conditions would aid clinicians and researchers in diagnosing, prognosing, and treating liver-associated disease conditions.

Naturally occurring Staphylococcal protein A comprises domains that form three-helix structures that bind to the Fc region of IgG. The Z domain of the 58-residue polypeptide derived from the B domain of staphylococcal protein A retains binding.

Certain polypeptides, derived from the Z-domain of protein A, contain a scaffold composed of three α-helices connected by loops. Certain residues situated on two of these helices constitute a binding site for the Fc-portion of IgG. According to the terminology used in the field of protein engineering, the binding surface is a surface situated on a scaffold. Thus, the present scaffold is a three-helical bundle protein domain. Alternative binder molecules were created by substituting 13 surface exposed amino acid residues situated on helices 1 and 2, to replace the ability to bind the Fc-portion of IgG with binding to other molecules.

BRIEF DESCRIPTION

Provided herein are PDGF-Rβ imaging agents comprising the polypeptide of any of SEQ. ID Nos 1, 2, 3, 4, 5, 6, 7, 8, 9 or a conservative variant thereof labeled with a signal generator (e.g., paramagnetic label, a radionuclide, or a fluorophore), wherein the polypeptide binds specifically to PDGFR-β. In some embodiments, polypeptide has a binding affinity of at least 10 nM to PDGFR-β expressed by A772 cells, U87 cells or M231 cells.

In some embodiments, the polypeptide may comprise at least two amino acid sequences selected from SEQ. ID NOS. 1, 2, 3, 4, 5, 6, 7, 8, 9 to form a multivalent polypeptide. The multivalent polypeptide may includes two repeated amino acid sequences have greater than 90% sequence identity to produce a divalent homogenous polypeptide.

In some embodiments, the signal generator may be a radionuclide is selected from fluorine (e.g., F-18), iodine (I-123), technechium (e.g., Tc-99m), gallium, or gadolinium. In some embodiments, the F-18 or I-123 is attached to the polypeptide via an aminoxy linker. In some alternative embodiments the F-18 or I-123 is attached to the polypeptide via an aminoxy linker at the N-terminus of the polypeptide.

In some embodiments, the technecium may be attached to the polypeptide via an PN linker such as CPN216. Alternatively, Tc-99m maybe attached to the polypeptide via a PN linker at the N-terminus of the polypeptide.

The paramagnetic label may comprise Gd-157, Mn-55, Dy-162, Cr-52, and Fe-56 and may be attached to the polypeptide via a chelator selected from NOTA, DOTA, DTPA.

The radioactive label may comprise Gd-153 or Ga-67 and be attached to the polypeptide via a chelator selected from NOTA, DOTA, DTPA.

FIGURES

These and other features, aspects, and advantages of the present invention will become better understood when the following detailed description is read with reference to the accompanying figures wherein:

FIG. 1 shows surface plasmon resonance (SPR) of anti-PDGF-Rβ polypeptides. FIG. 1A shows the binding of Z2465 (SEQ. ID NO. 16) against human PDGF-Rβ. FIG. 1B shows the binding of Z2465 (SEQ. ID NO. 16) against murine PDGF-Rβ.

Figure 6A:
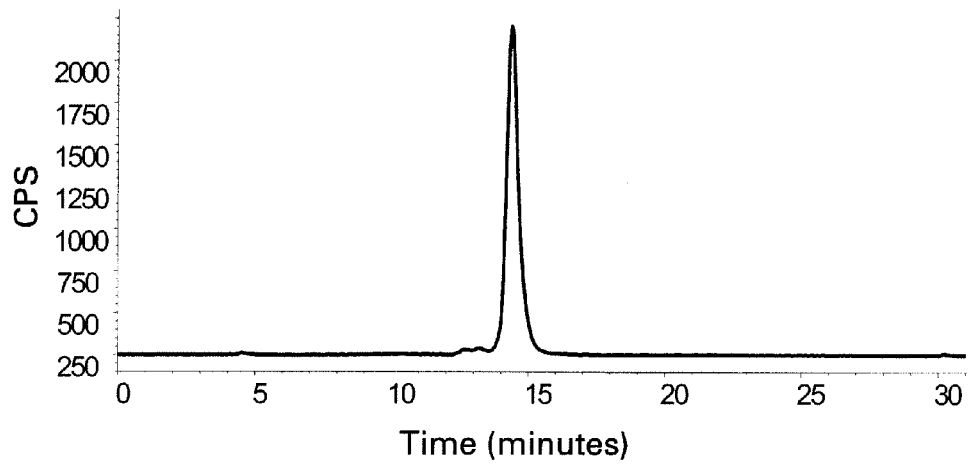
Figure 6B:
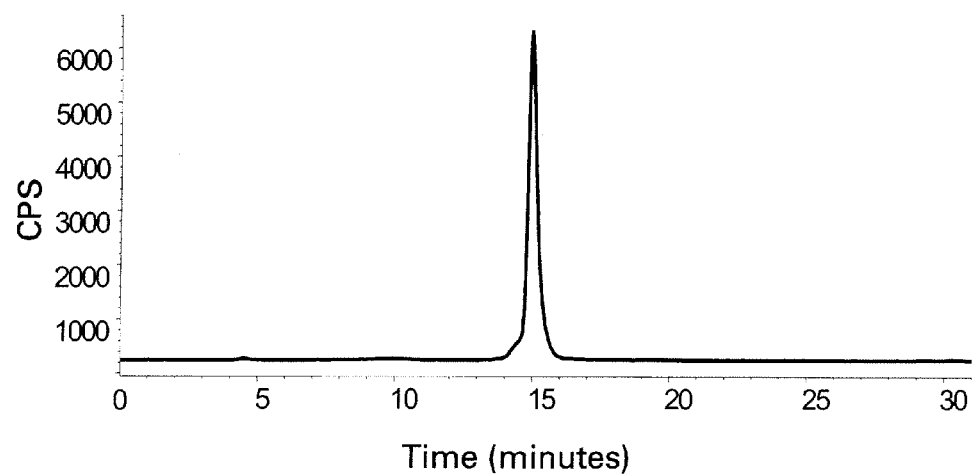

FIG. 6 shows HPLC gamma chromatograms of labeled Z2465 (SEQ. ID NO. 16). The chromatogram in FIG. 6A shows monomeric version and FIG. 6B shows the dimeric version (Z2465)$_2$(SEQ. ID NO. 19).

Figure 7A:
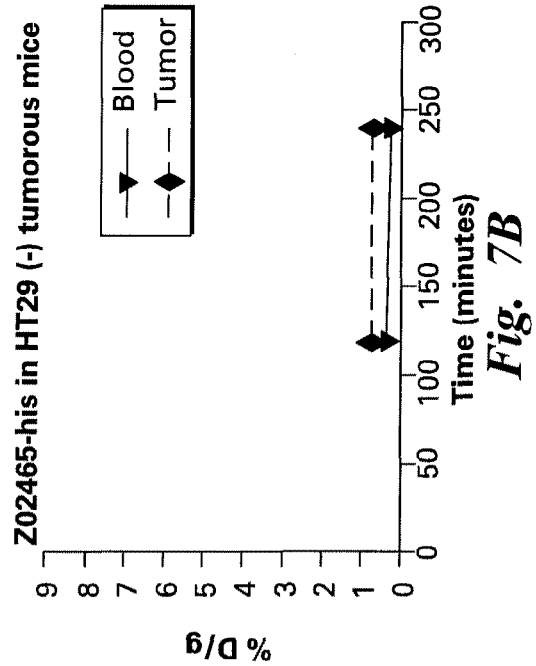
Figure 7C:
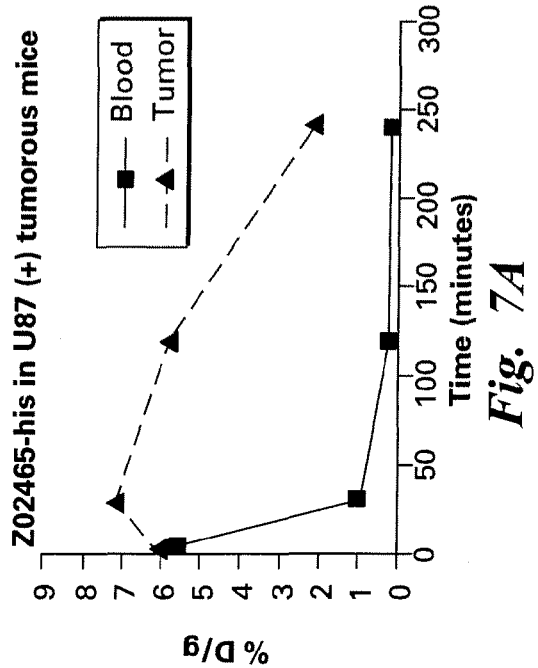
Figure 7B:
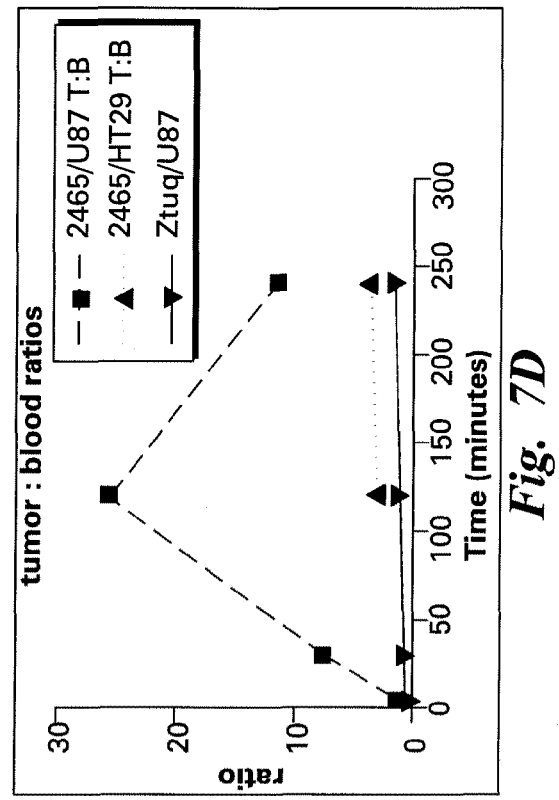
Figure 7D:
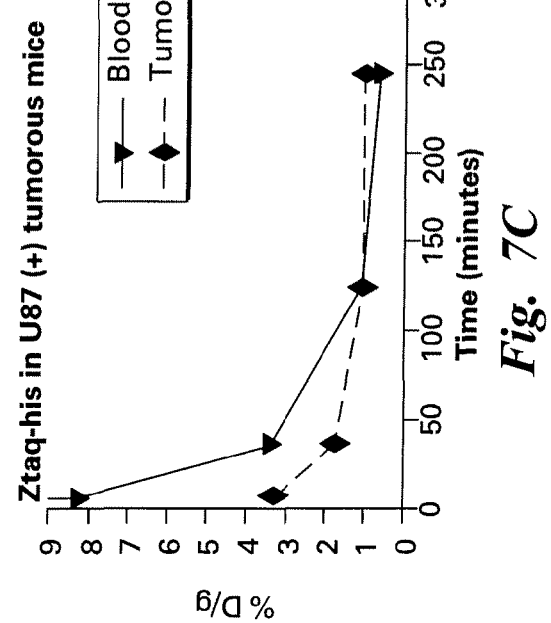

FIGS. 7A through 7D show in vivo biodistribution studies of Z2465 (SEQ. ID NO. 16) in blood and in tumor tissue. FIG. 7A shows the distribution of Z2465 (SEQ. ID NO. 16) in U87-tumored mice. FIG. 7B shows the distribution of Z2465 (SEQ. ID NO. 16) in HT-29-tumored mice. FIG. 7C shows the distribution of Ztaq (SEQ. ID NO. 10) in U87-tumored mice. And, FIG. 7D shows the tumor:blood ratios for the series of experiments depicted in FIGS. 7A-7C.

Figure 8A:
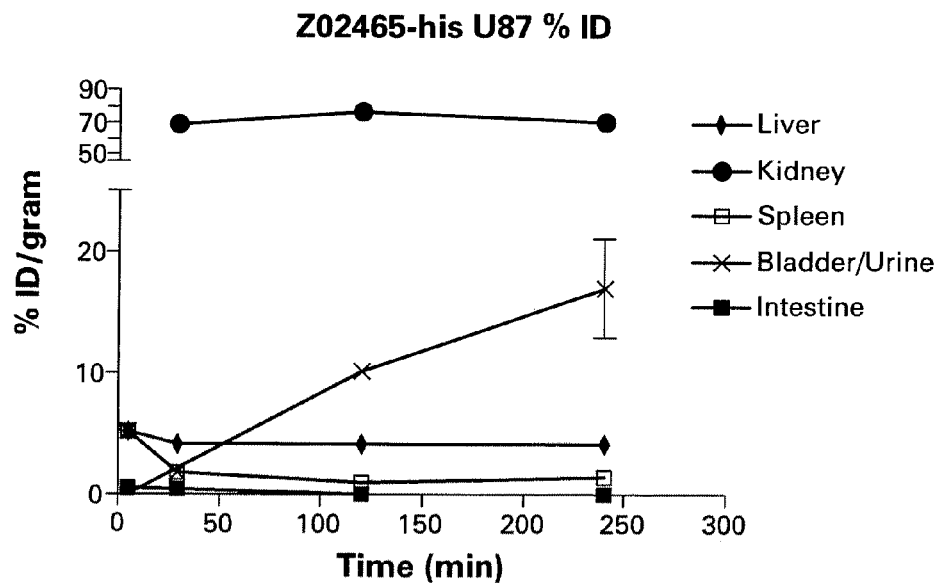
Figure 8B:
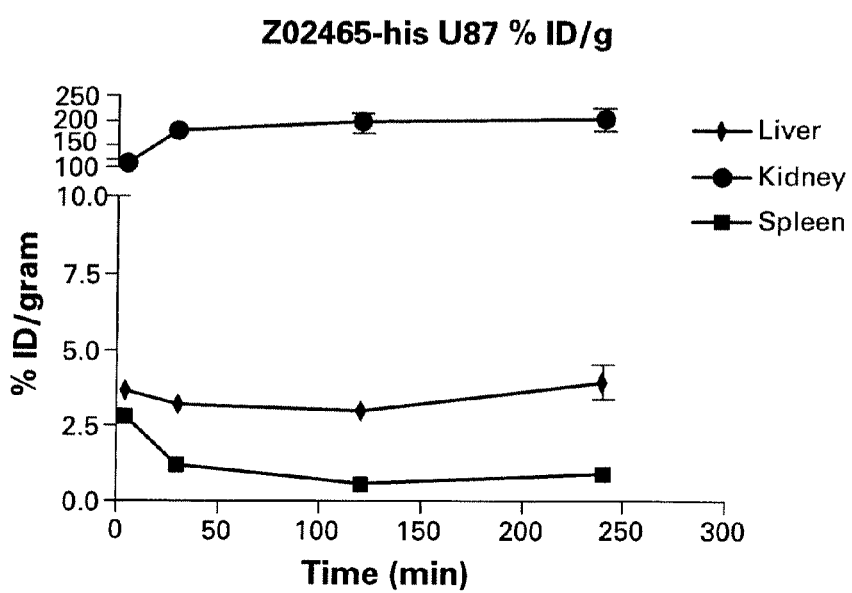

FIGS. 8A and 8B show the clearance patterns of Z2465 (SEQ. ID NO. 16). FIG. 8A shows the % ID [% injected dose] of Z2465 (SEQ. ID NO. 16) in liver, kidney, spleen, bladder/urine, and intestine. FIG. 8B shows the % ID/g [% injected dose/gram of tissue] for liver, kidney and spleen.

Figure 9A:
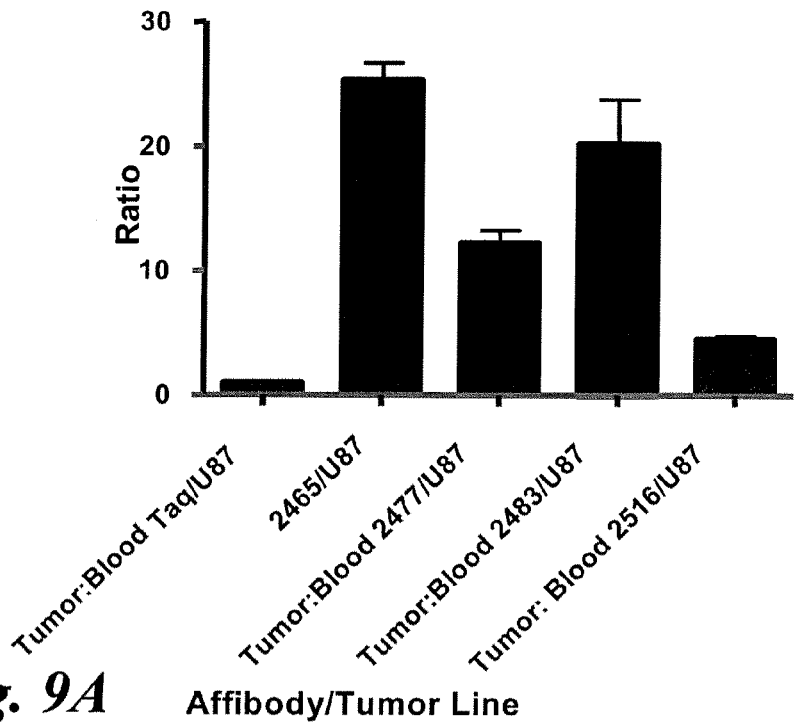
Figure 9B:
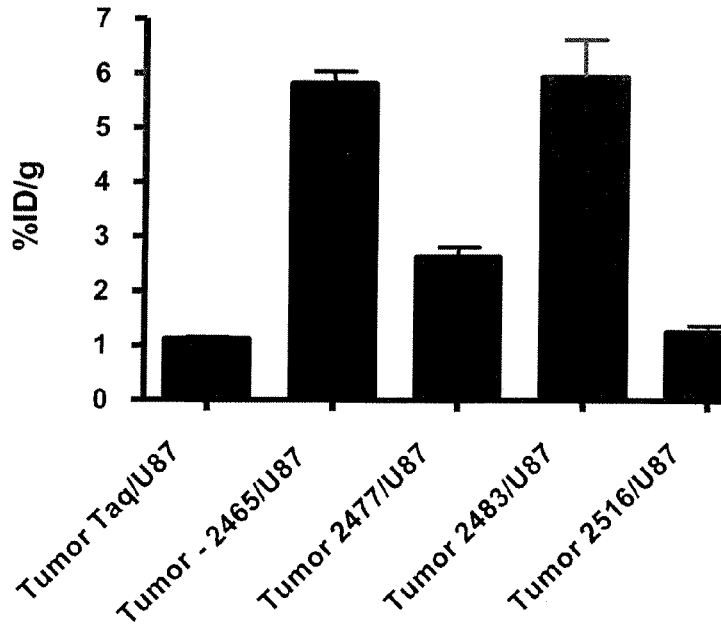

FIG. 9A shows the tumor:blood ratios at 2 hour post injection for five polypeptides Ztaq (SEQ. ID NO. 10), Z2465 (SEQ. ID NO. 16), Z2477 (SEQ. ID NO. 25), Z2483 (SEQ. ID. NO. 18), Z2516 (SEQ. ID NO. 17) using the U87 tumor cell line. FIG. 9B shows the tumor uptake at 2 hour post injection for five polypeptides using the U87 tumor cell line.

Figure 10A:
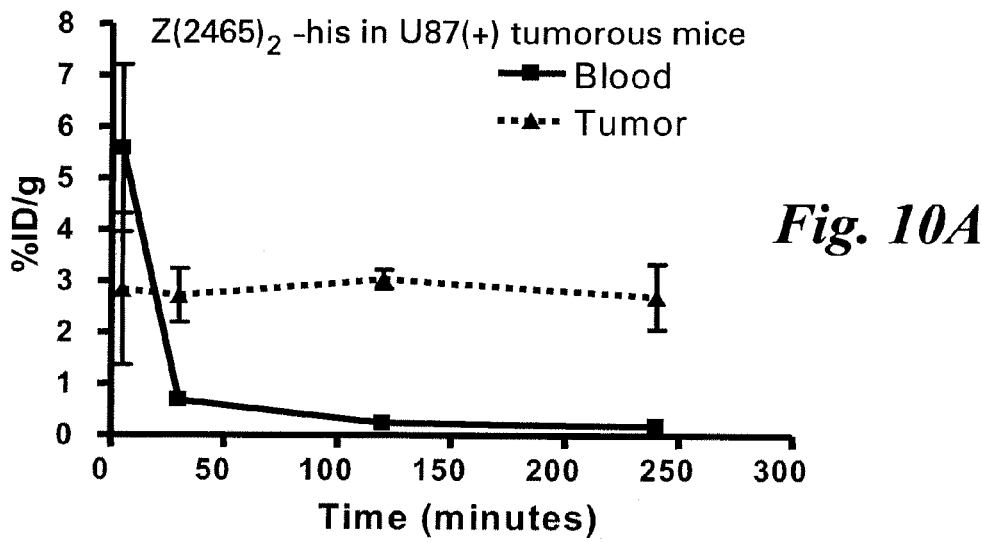
Figure 10B:
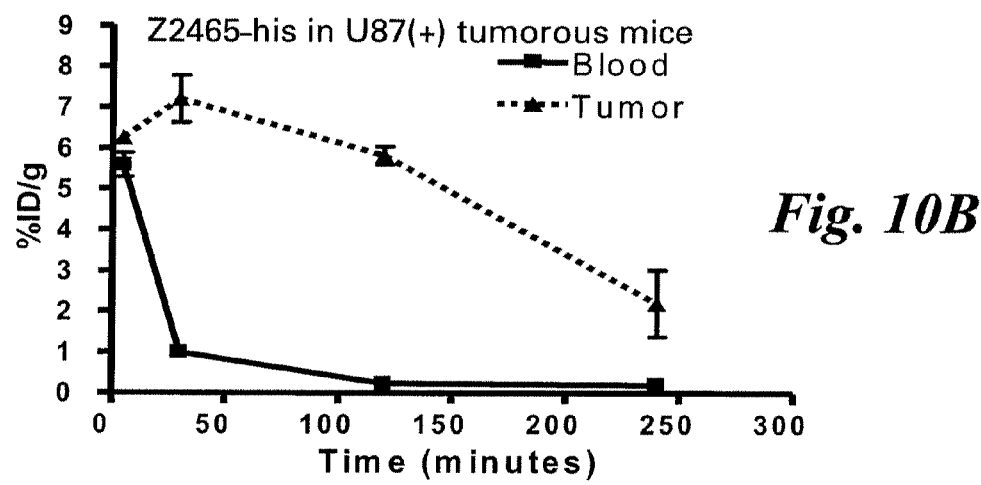
Figure 10C:
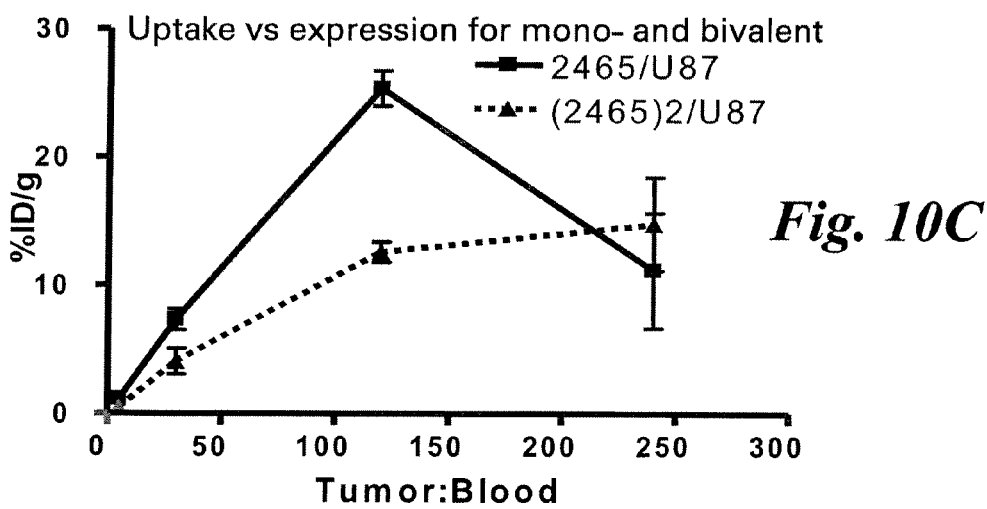

FIGS. 10A through 10C show valency comparisons for monovalent and bivalent version of the Z2465(SEQ. ID NO. 16 and 19) polypeptides. FIG. 10A shows the levels of the bivalent (Z2465)$_2$ (SEQ. ID NO. 19) in blood and tumor cells over time. FIG. 10B shows the levels of the monovalent Z2465 (SEQ. ID NO. 16) in blood and tumor cells over time. FIG. 10C shows a comparison of the monovalent (SEQ. ID. NO. 16) and bivalent (SEQ. ID. NO. 19) species.

Figure 11:
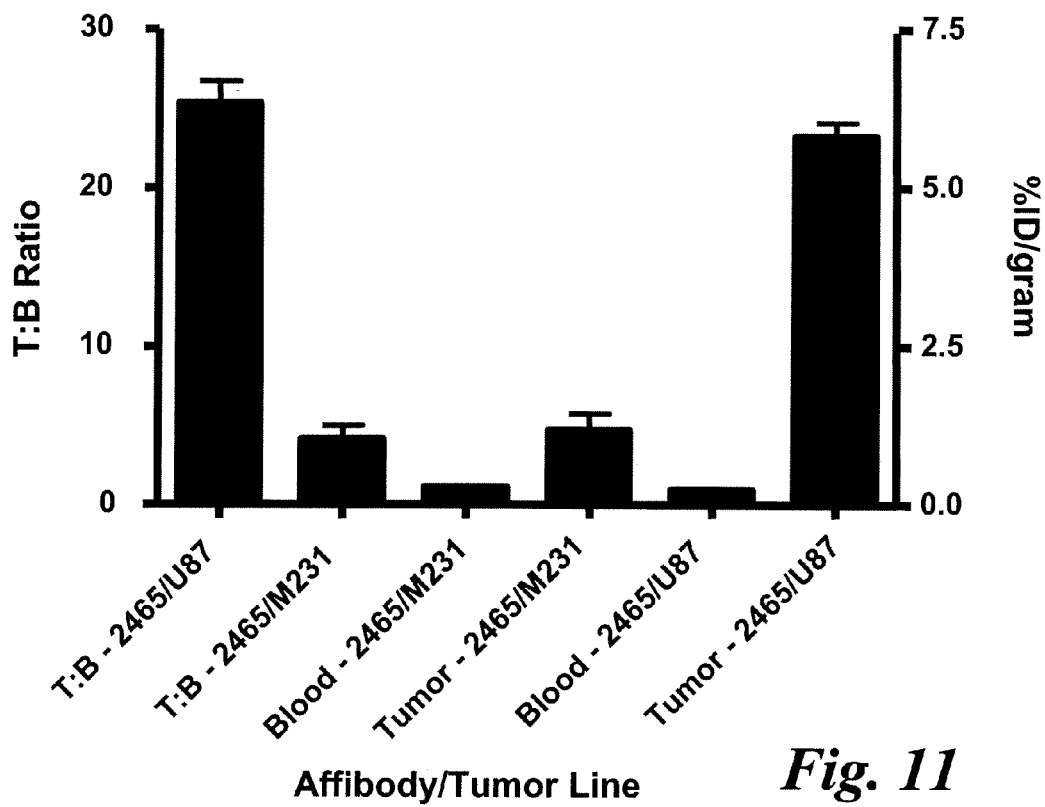

FIG. 11 shows the comparison of tumor:blood ratio with % ID/g of the $^{99m}$Tc-labeled Z2465 (SEQ. ID NO. 16) and (Z2465)2 (SEQ. ID NO. 19) in high (U87) and moderate/low (M231) expressing tumors.

Figure 12:
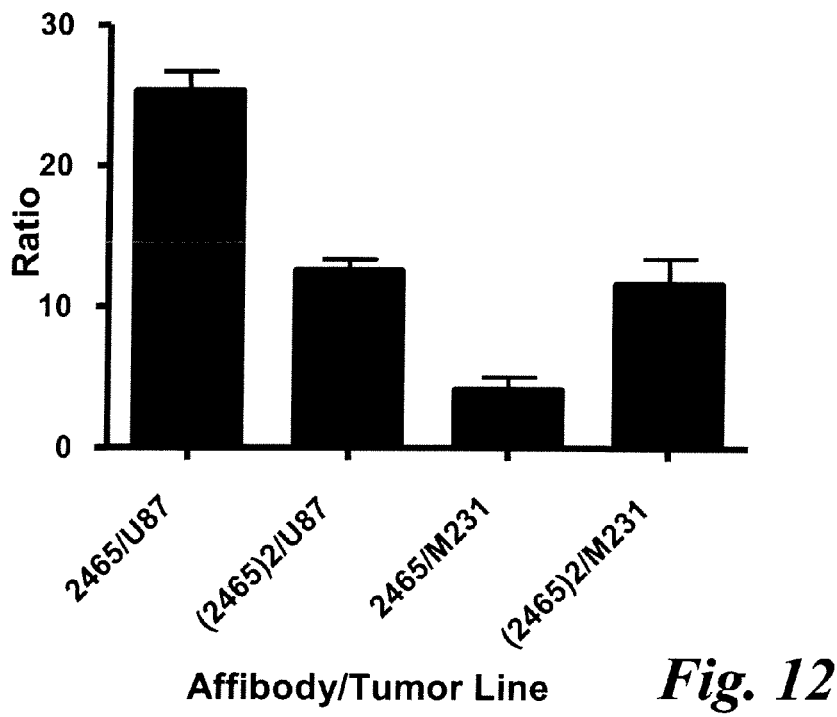

FIG. 12 shows tumor:blood ratios at 2 hour post injection for monovalent (SEQ. ID NO. 16) and bivalent polypeptides (SEQ. ID NO. 19) using high (U87) and moderate/low (M231) expressing tumors.

Figure 13:
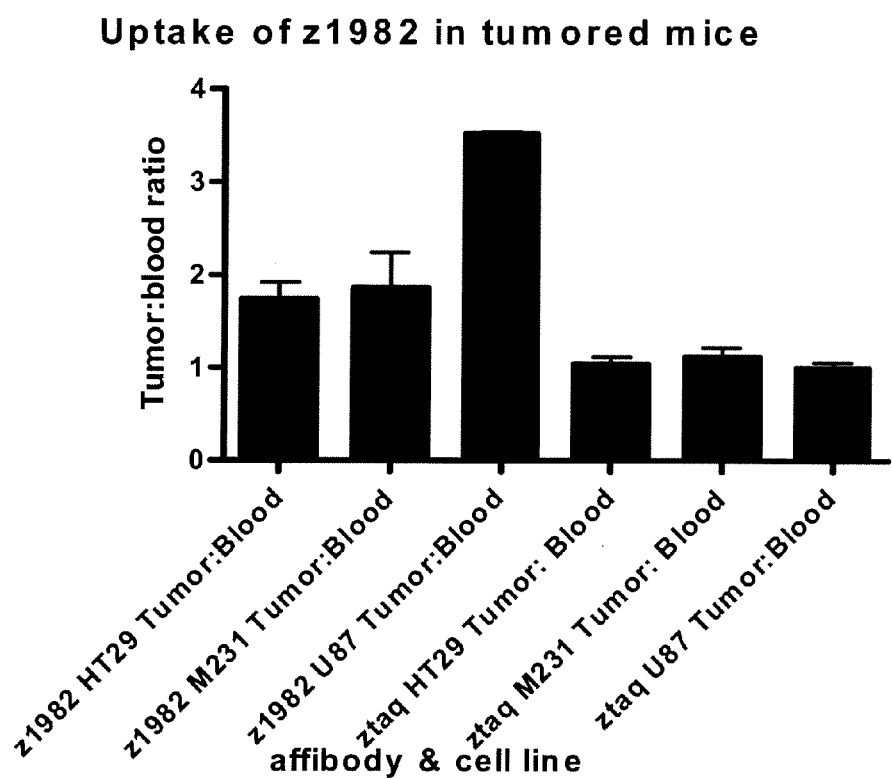

FIG. 13 shows the tumor:blood ratios for Ztaq (SEQ. ID NO. 10) and Z1982 (SEQ. ID NO. 14) in three cell lines: HT29, M231, and U87.

Figure 14:
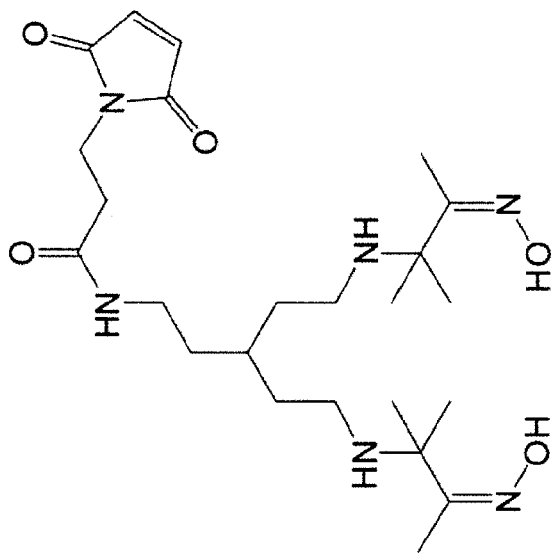

FIG. 14 shows the chemical structure for the Mal-cPn216 linker.

Figure 15:
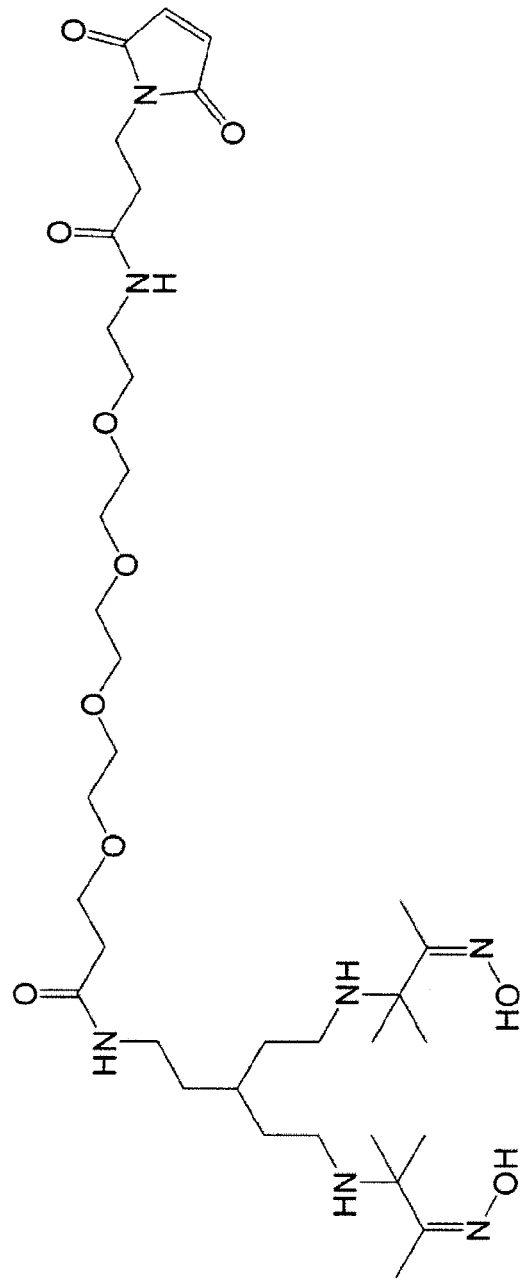

FIG. 15 shows the chemical structure for the Mal-PEG-cPn216.

Figure 16:
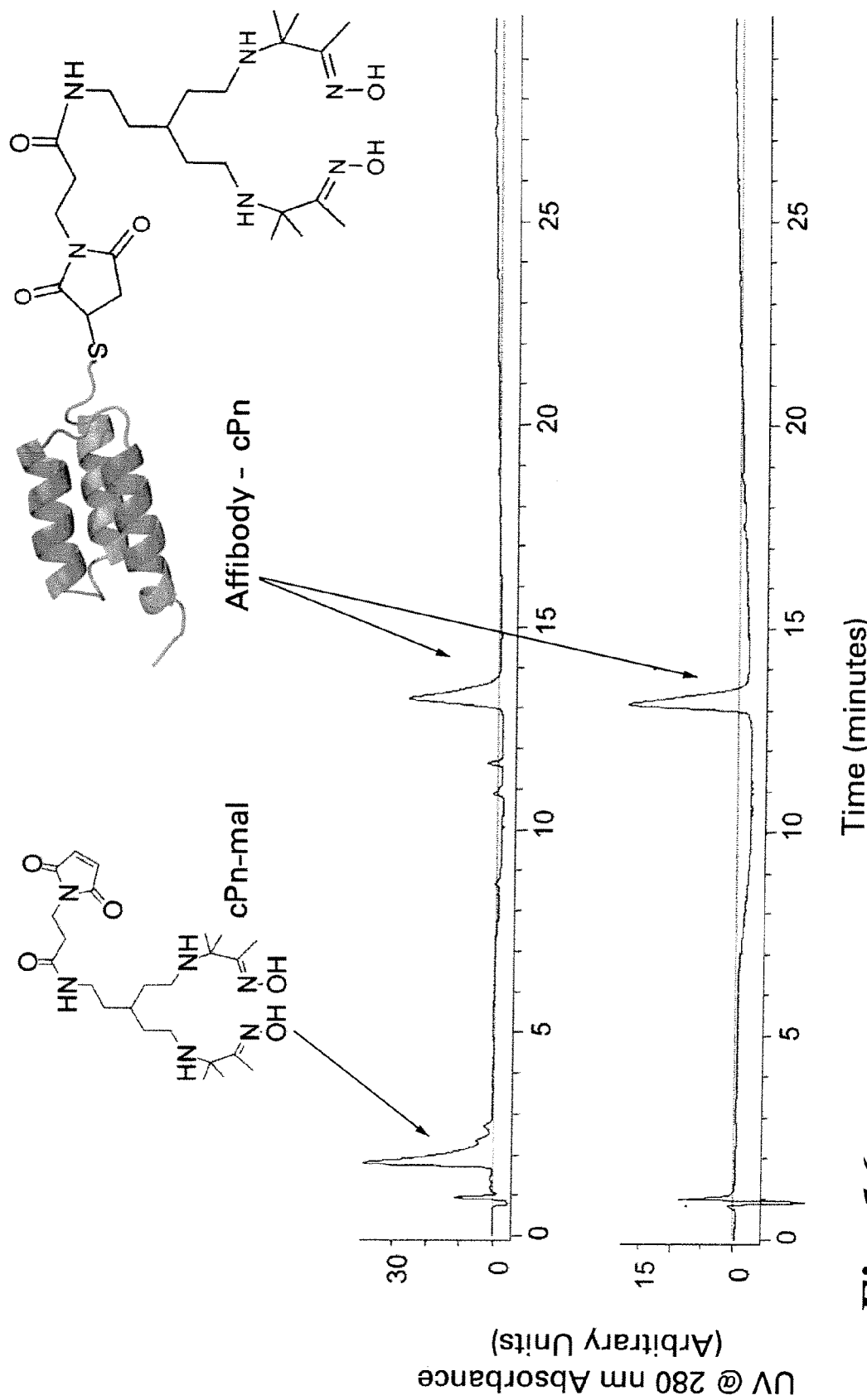

FIG. 16 shows the reverse phase high pressure liquid chromatography (HPLC) purification of the cPn216-labelled Z02465 (SEQ. ID NO. 23).

Figure 17:
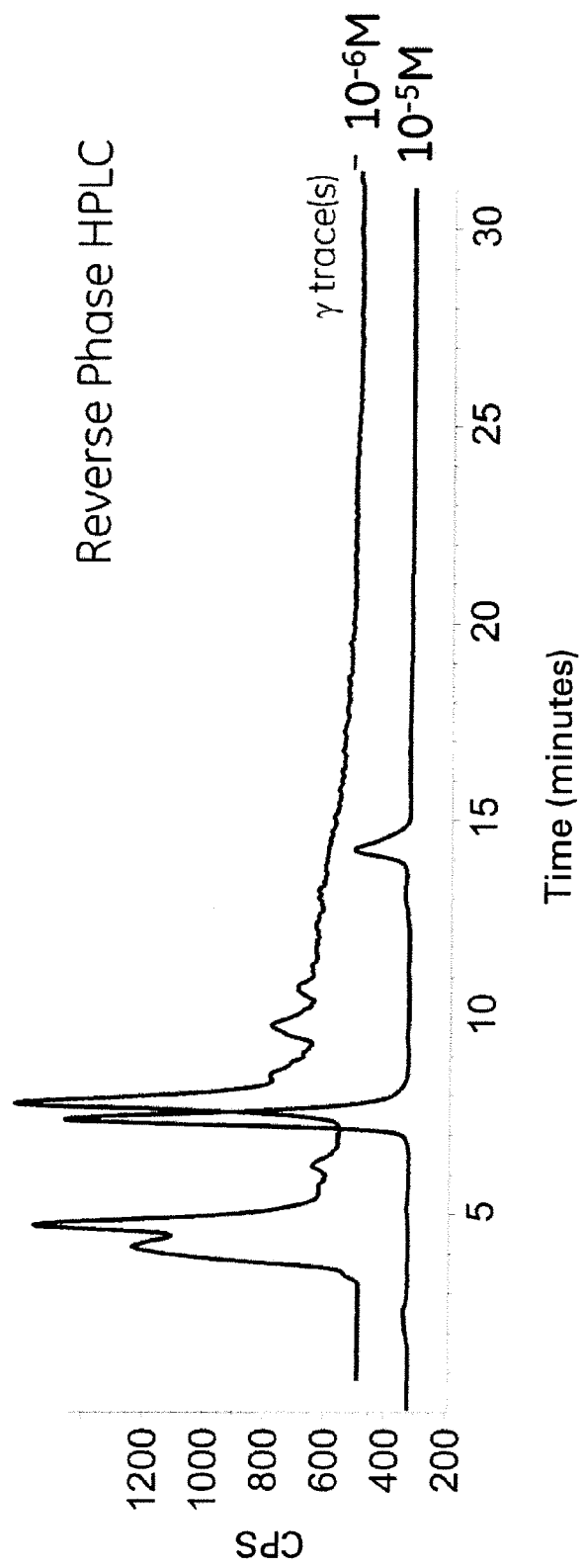

FIG. 17 illustrates the concentration dependence for the labeling of cPn216-labelled Z2465 (SEQ. ID NO. 16) with Tc-99m.

Figure 18:
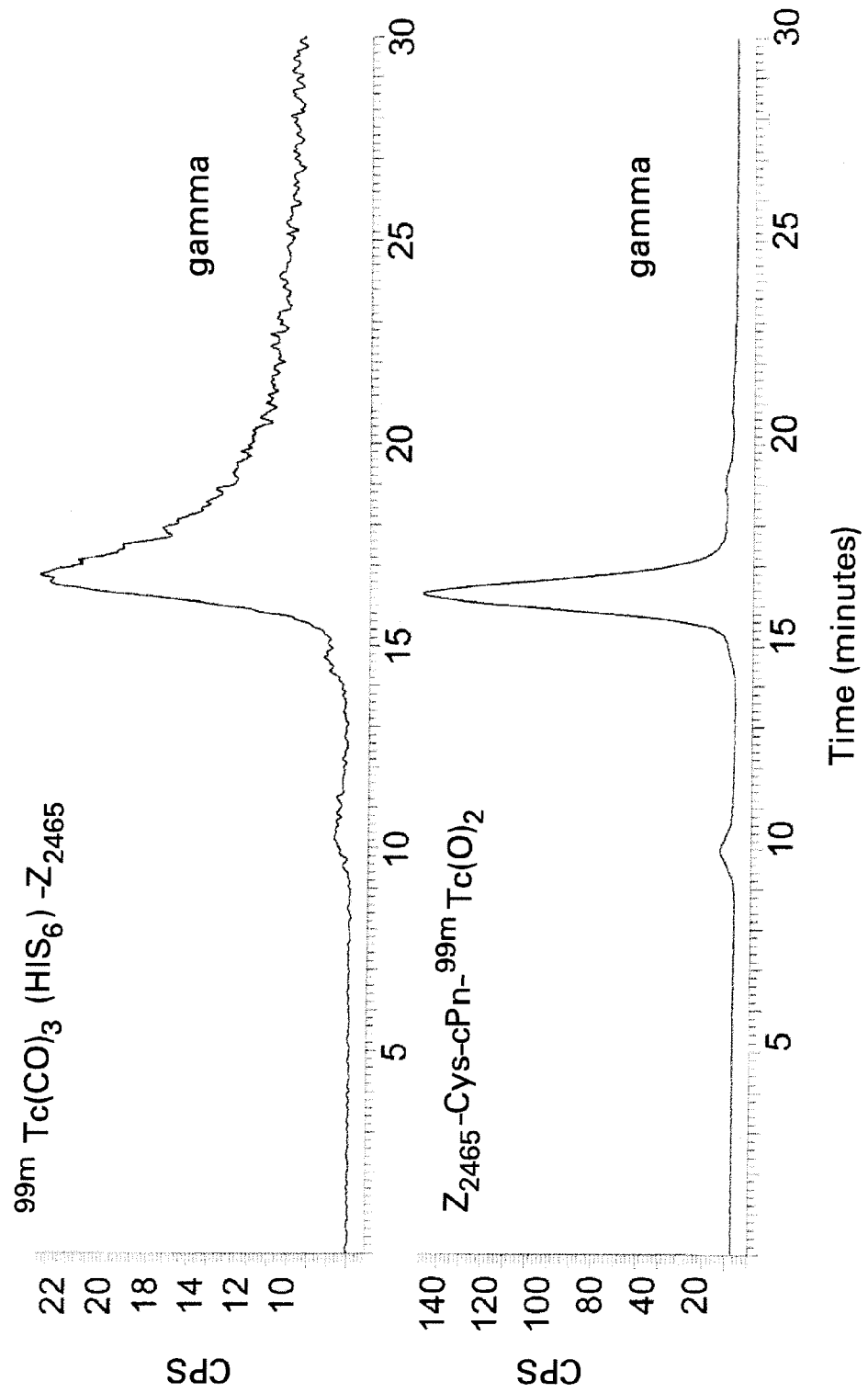

FIG. 18 illustrates the similarity in retention time by Size Exclusion Chromatography HPLC for Tc-99m labeled Z2465 (SEQ. ID NO. 16) and cPn216-labeled Z02465 (SEQ. ID NO. 23)

Figure 19:
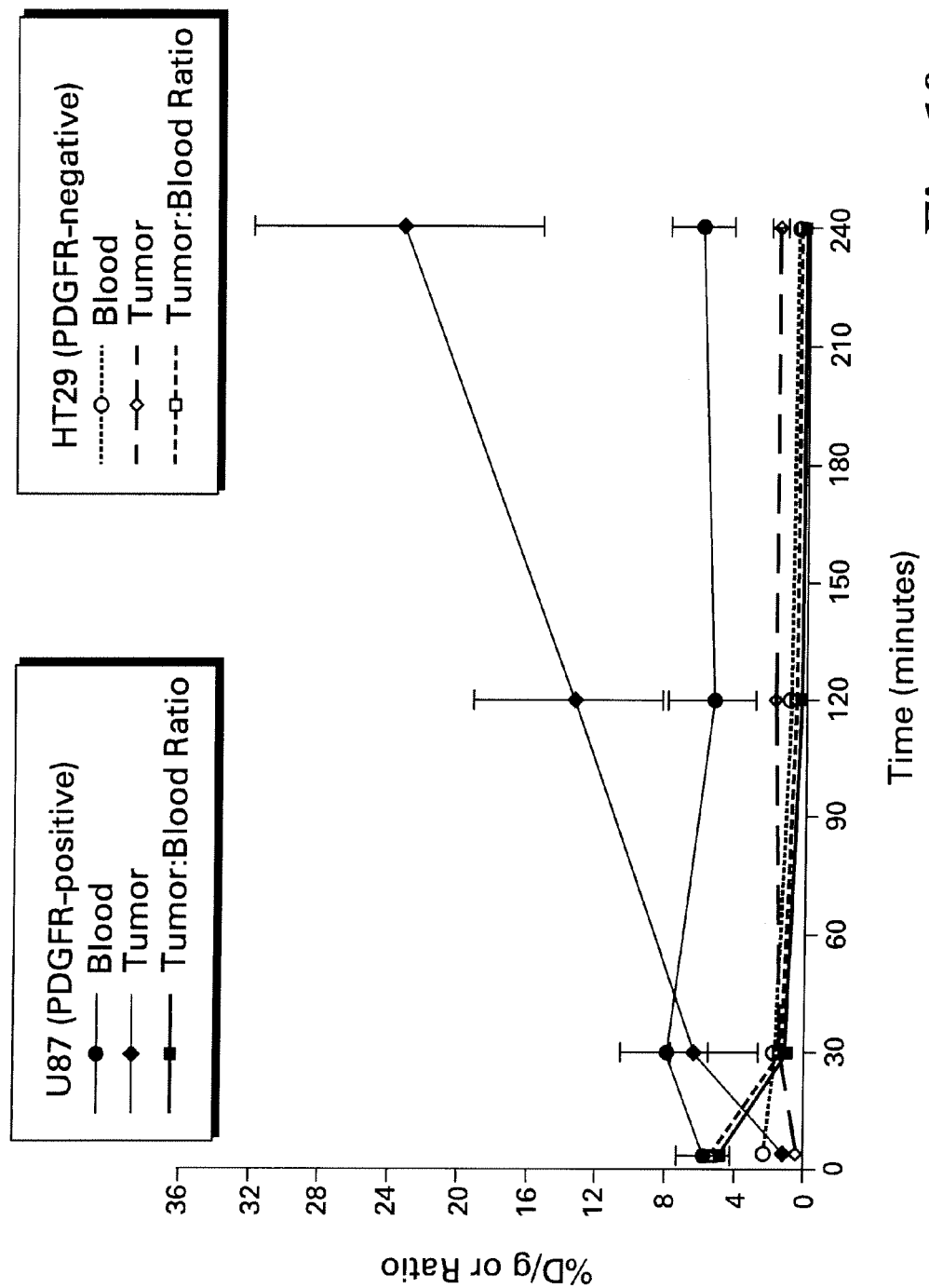

FIG. 19 shows tumor uptake U87 and HT 29 cells for that Z02465 (SEQ. ID NO. 23) labeled with Tc-99m via cPn216.

Figure 20:
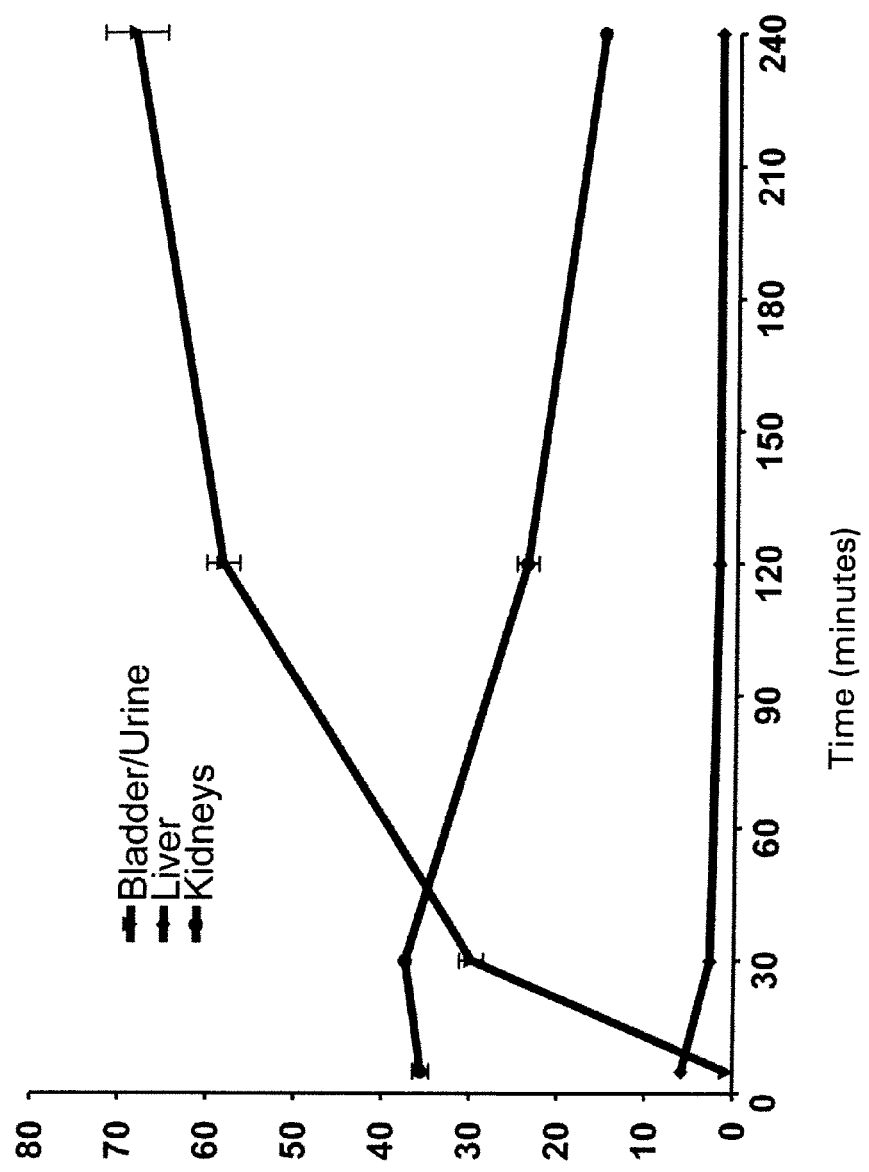

FIG. 20 shows the clearance profile (% ID, % injected dose) in liver, kidneys and bladder/urine of Z02465 (SEQ. ID NO. 23) labeled with Tc-99m via cPn216.

Figure 21A:
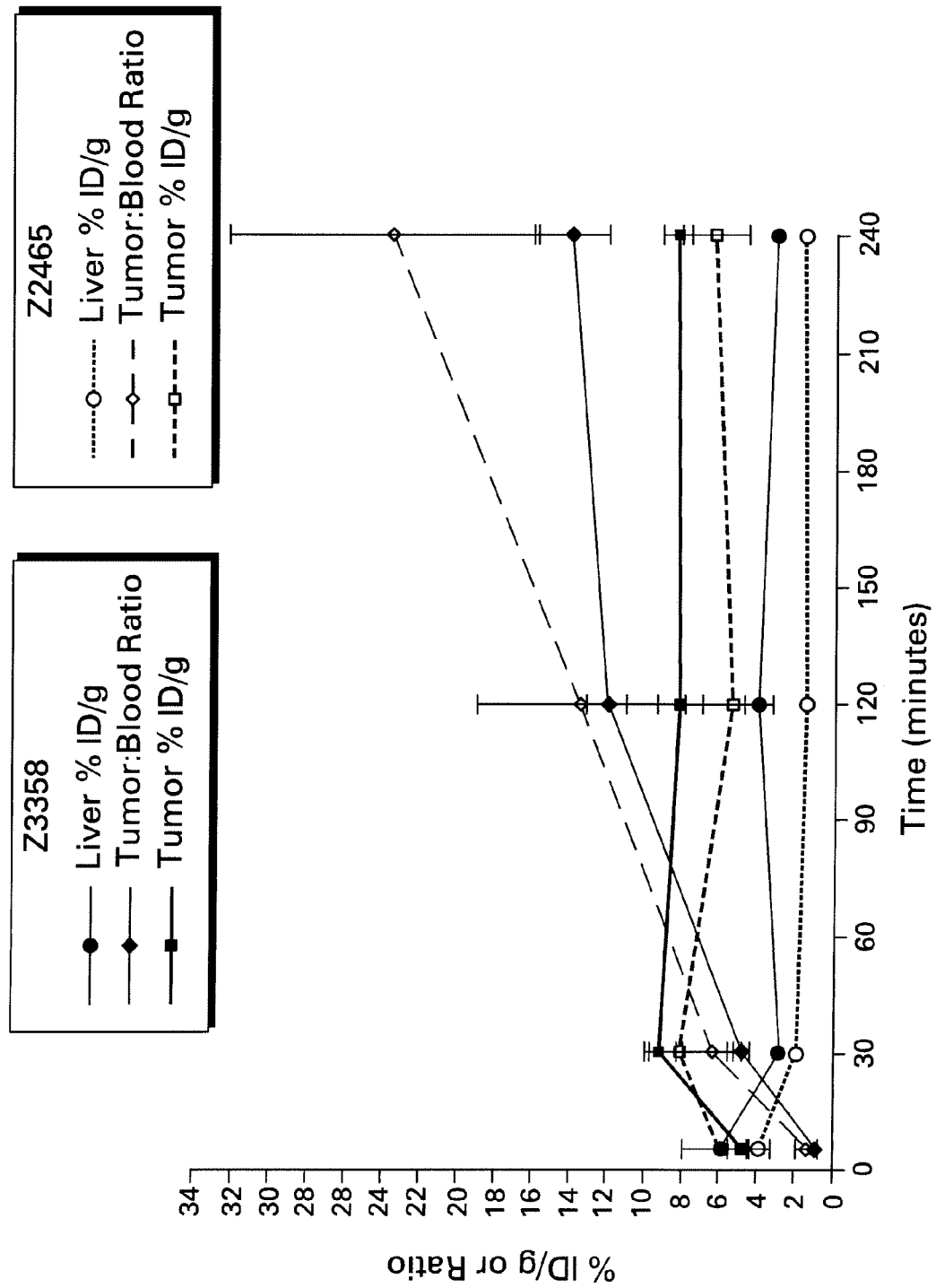
Figure 21B:
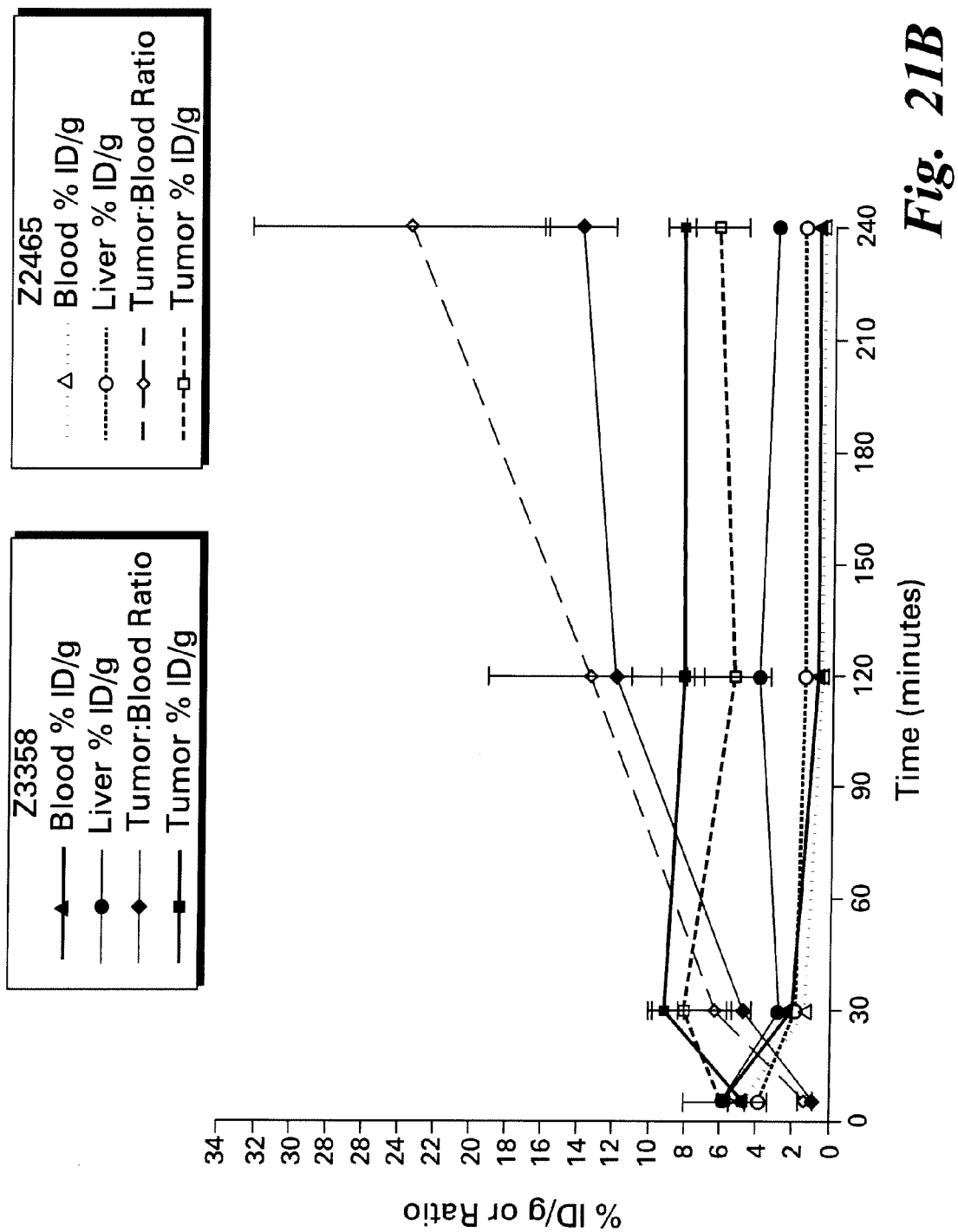

FIG. 21 shows that Z03358 (SEQ. ID NO. 24) demonstrates a biodistribution pattern similar to Z02465 (SEQ. ID NO. 23). Panel 21A shows the tumor:blood ratio, % ID/g in the tumor and % ID/g in the liver and Panel 21B shows the same but includes the % ID/g in the blood.

Figure 22:
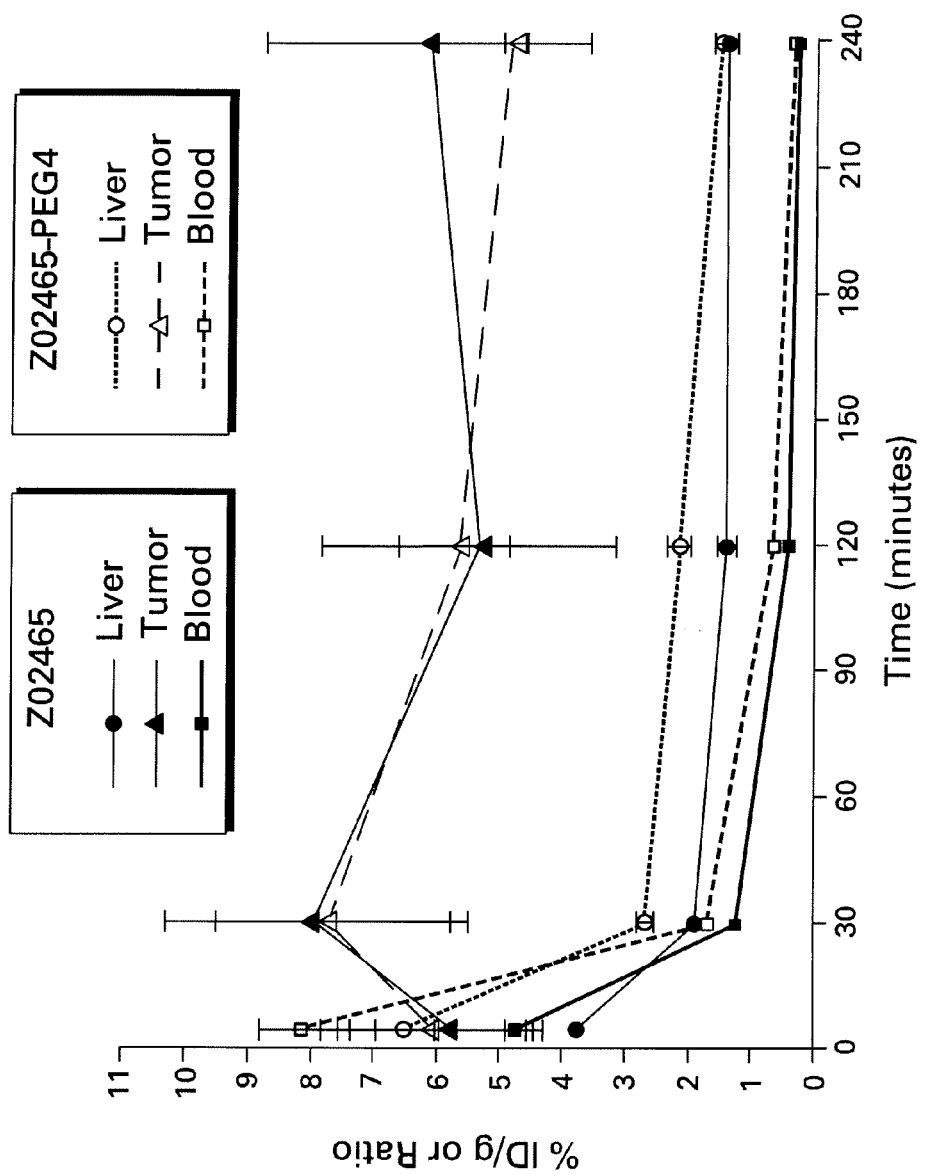

FIG. 22 shows tumor uptake U87 and HT-29 cells for that Z02465 (SEQ. ID NO. 23) labelled with Tc-99m via PEG$_4$-cPn216.

Figure 23A:
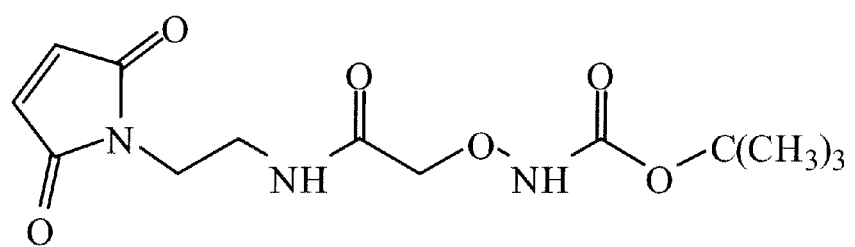
Figure 23B:
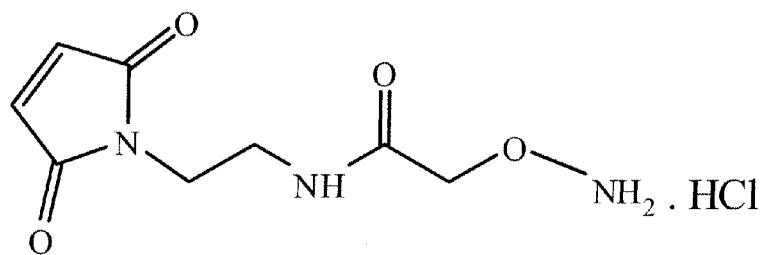

FIGS. 23A and 23B show the chemical structure for malimide-aminoxy (Mal-AO) linkers. FIG. 23A depicts the chemical structure for tert-butyl 2-(2-(2,5-dioxo-2,5-dihydro-1H-pyrrol-1-yl)ethylamino)-2-oxoethoxycarbamate and FIG. 23B depicts the chemical structure for 2-(aminooxy)-N-(2-(2,5-dioxo-2,5-dihydro-1H-pyrrol-1-yl)ethyl)acetamide hydrochloride.

Figure 24:
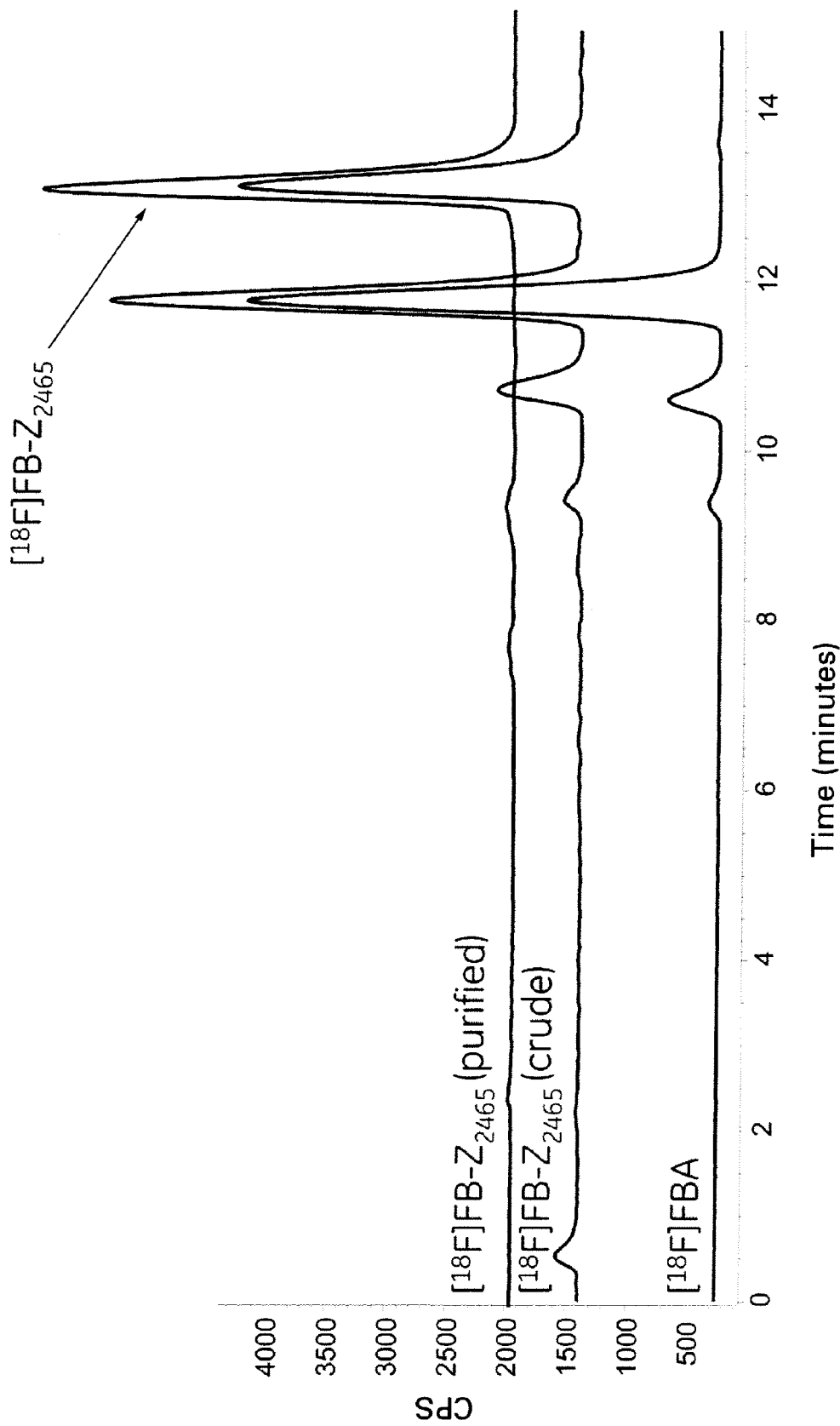

FIG. 24 shows the Z02465 (SEQ. ID NO. 23) polypeptide labeled with $^{18}$F.

Figure 25A:
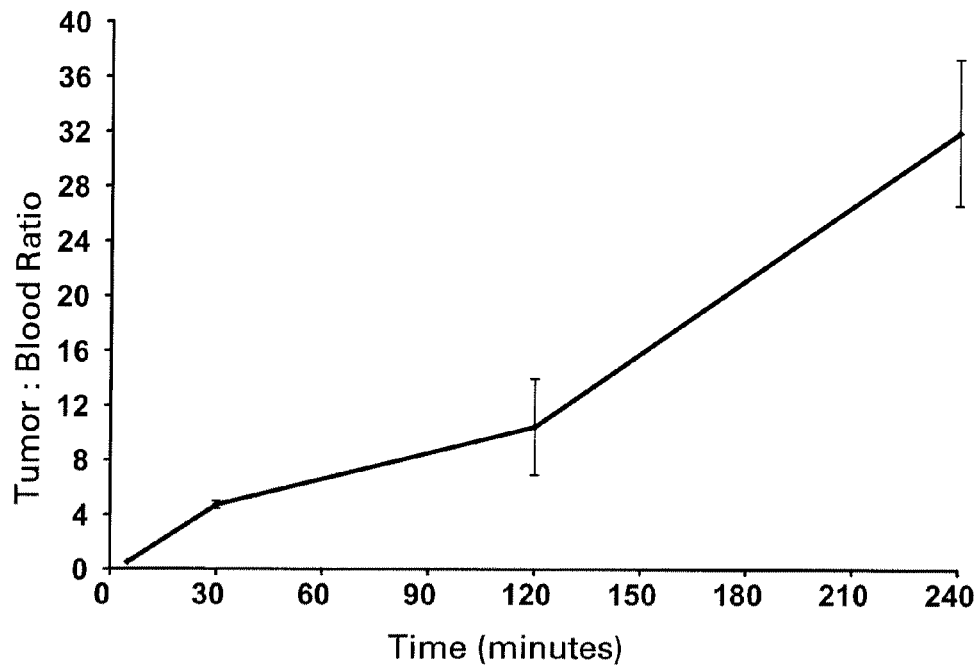
Figure 25B:
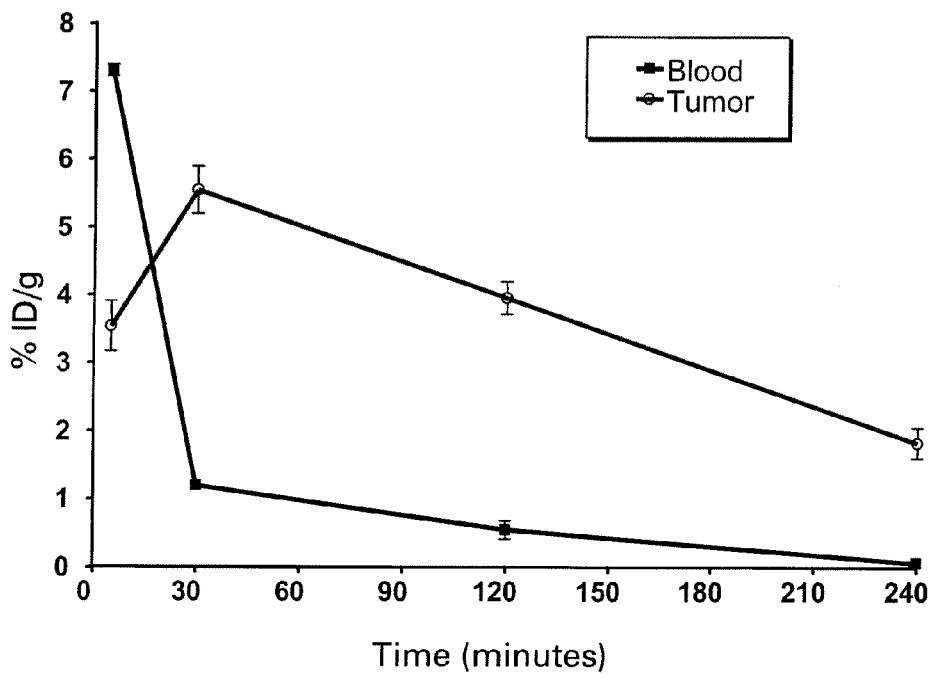

FIGS. 25A and 25B show the % ID/g (FIG. 25A) and the tumor:blood ratio (FIG. 25B) for the Z02465 (SEQ. ID NO. 23) polypeptide labeled with F-18 in U87-tumored animals.

Figure 26A:
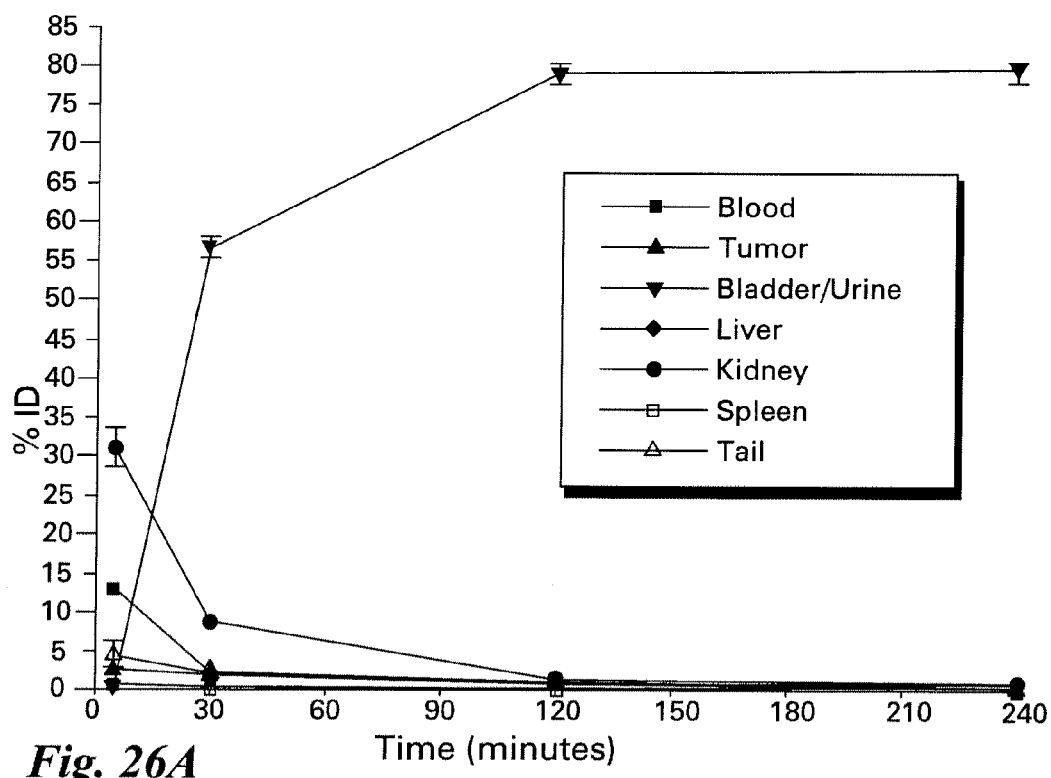
Figure 26B:
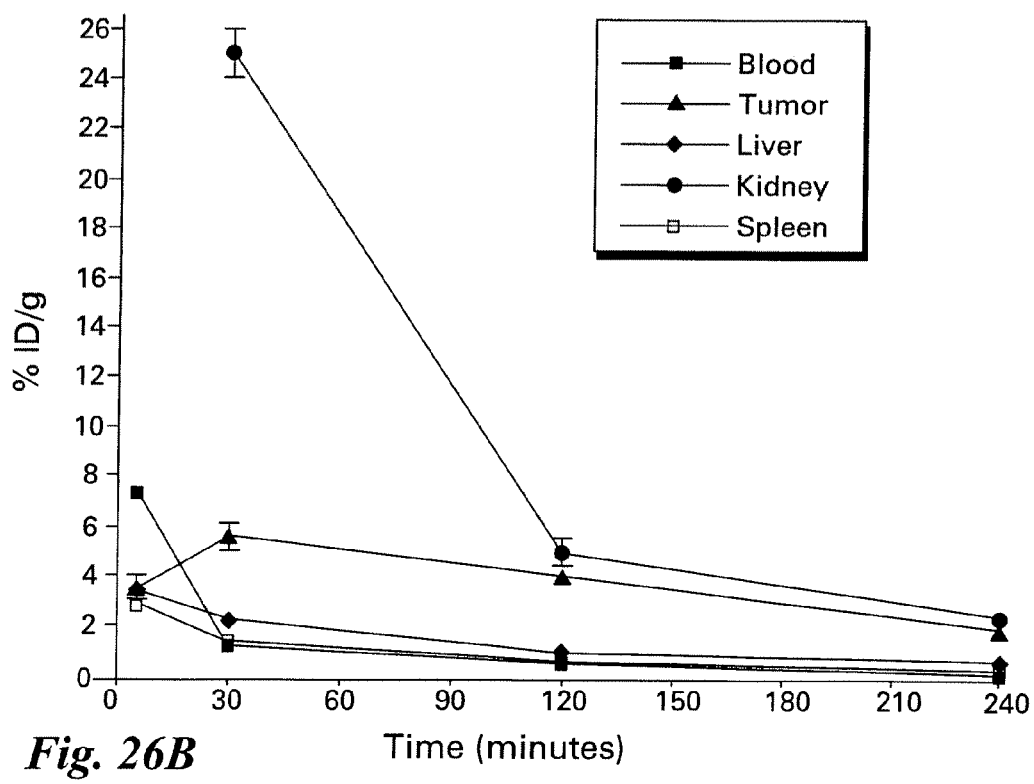

FIGS. 26A and 26B show the clearance profile of F-18 labeled Z02465 (SEQ. ID NO. 23) (% ID) of blood, tumor, bladder/urine, liver, kidneys, spleen, and tail (FIG. 26A) and % ID/g of blood, tumor, liver, kidneys, and spleen (FIG. 26B).

Figure 27:
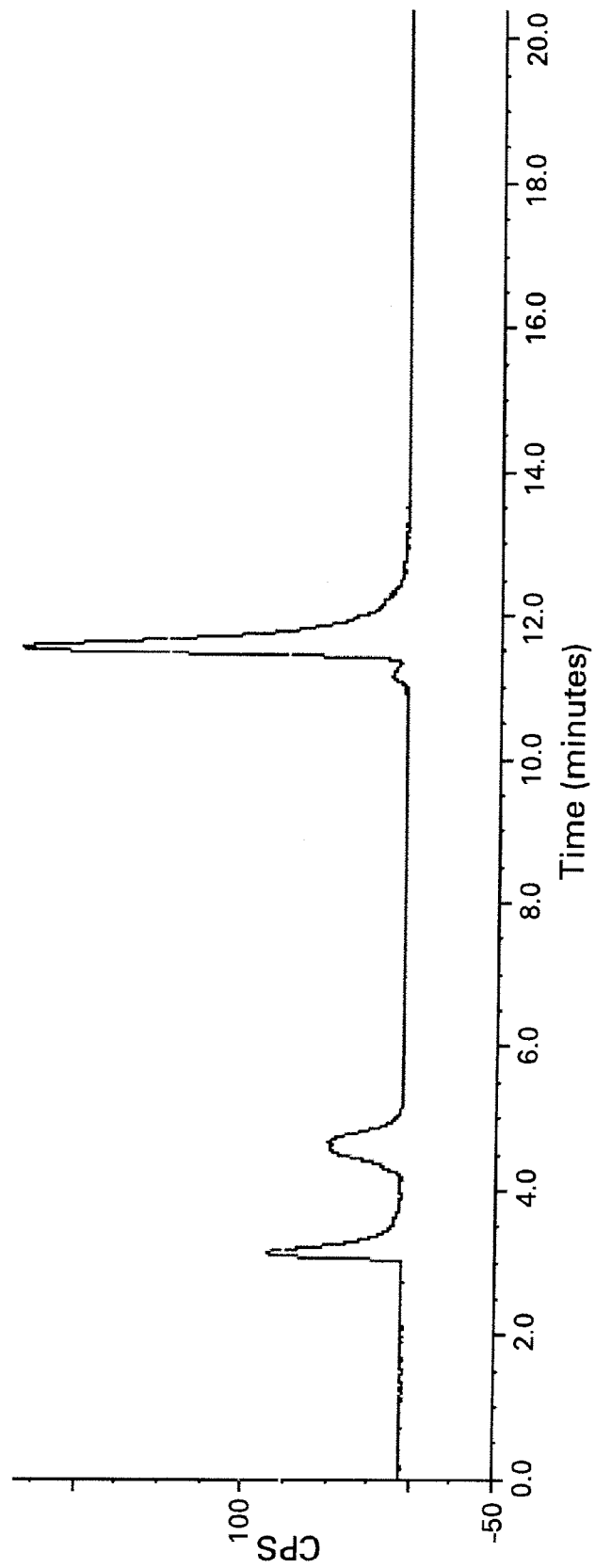

FIG. 27 shows the gamma trace HPLC for crude Gd-153-DOTA-labeled Z2465 (SEQ. ID NO. 16).

Figure 28:
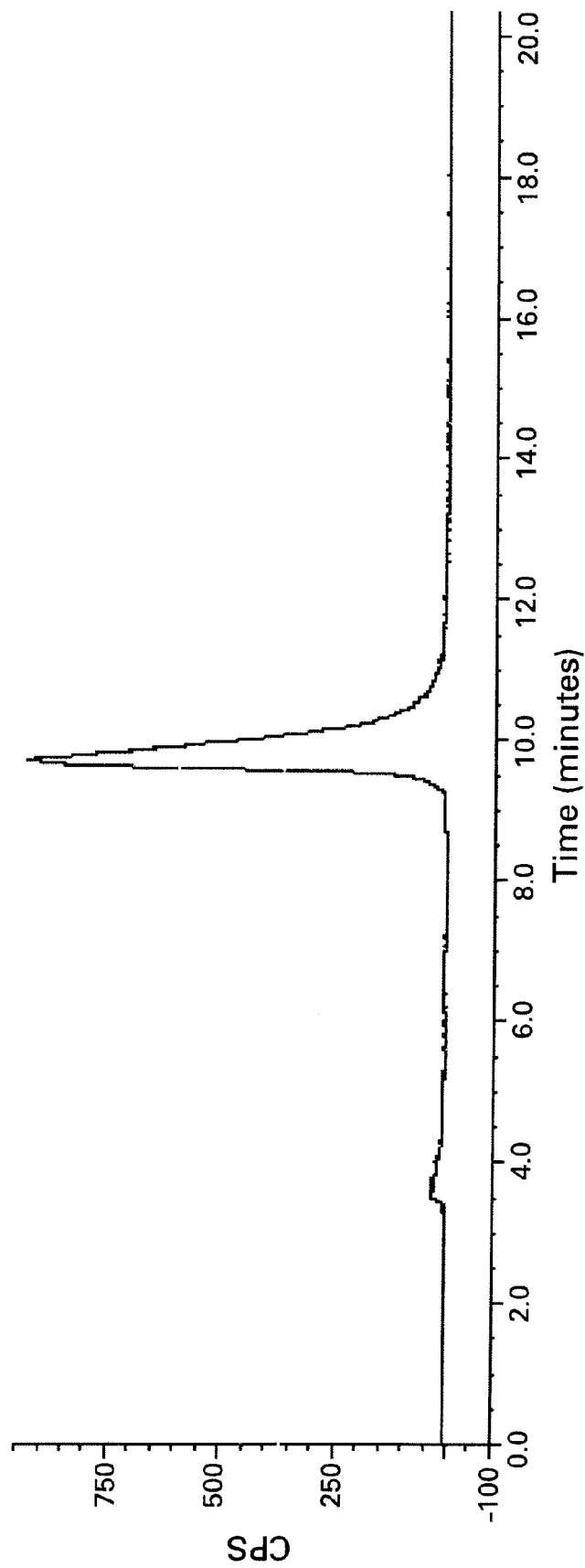

FIG. 28 shows the gamma trace HPLC for purified Gd-153-DOTA-labeled Z2465 (SEQ. ID NO. 16).

DETAILED DESCRIPTION

The following detailed description is exemplary and not intended to limit the invention of the application and uses of the invention. Furthermore, there is no intention to be limited by any theory presented in the preceding background of the invention of the following detailed description. To more clearly and concisely describe and point out the subject matter of the claimed invention, the following definitions are provided for specific terms that are used in the following description and the claims appended hereto.

Unless otherwise indicated, the word "a" refers to one or more than one of the word modified by the article "a."

The term "polypeptide" with reference generally refers to those residues of the polypeptide that provide the three-dimensional structure to adequately position the binding interface residues of the polypeptide such that binding to a target is enabled. Any sequence that preserves the binding site and binding activity with the same topology (the z-domain three-helical fold) is based on the polypeptide.

"Aliphatic Amino Acid" refers to a hydrophobic amino acid having an aliphatic hydrocarbon side chain. Genetically encoded aliphatic amino acids include Ala (A), Val (V), Leu (L), and Ile (I).

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, for example, hydroxyproline, γ-carboxyglutamate, O-phosphoserine, phosphothreonine, and phosphotyrosine. Categories of amino acids herein defined are not mutually exclusive. Thus, amino acids having side chains exhibiting two or more physical-chemical properties can be included in multiple categories. For example, amino acid side chains having aromatic moieties that are further substituted with polar substituents, such as Tyr (Y), may exhibit both aromatic hydrophobic properties and polar or hydrophilic properties, and can therefore be included in both the aromatic and polar categories. The appropriate categorization of any amino acid will be apparent to those of skill in the art, in light of the detailed disclosure provided herein.

"Acidic Amino Acid" refers to a hydrophilic amino acid having a side chain pK value of less than 7. Acidic amino acids typically have negatively charged side chains at physiological pH due to loss of a hydrogen ion. Genetically encoded acidic amino acids include Glu (E) and Asp (D).

"Amino acid analogs" refer to compounds that have the same basic chemical structure as a naturally occurring amino acid (i.e., a carbon that is bound to a hydrogen, a carboxyl group, an amino group) including a non-conventional R group, (e.g., homoserine, norleucine, methionine sulfoxide, or methionine methyl sulfonium). Such analogs have modified R groups (e.g., norleucine) or modified peptide backbones, but retain the same basic chemical structure as a naturally occurring amino acid.

"Aromatic Amino Acid" refers to a hydrophobic amino acid with a side chain having at least one aromatic or heteroaromatic ring. The aromatic or heteroaromatic ring may contain one or more substituents such as —OH, —SH, —CN, —F, —Cl, —Br, —I, —NO2, —NO, —NH2, —NHR, —NRR, —C(O)R, —C(O)OH, —C(O)OR, —C(O)NH2, —C(O)NHR, —C(O)NRR and the like where each R is independently (C1-C6)alkyl, substituted (C1-C6)alkyl, (C1-C6)alkenyl, substituted (C1-C6)alkenyl, (C1-C6)alkynyl, substituted (C1-C6)alkynyl, (C5-C20)aryl, substituted (C5-C20)aryl, (C6-C26)alkaryl, substituted (C6-C26)alkaryl, 5-20 membered heteroaryl, substituted 5-20 membered heteroaryl, 6-26 membered alkheteroaryl or substituted 6-26 membered alkheteroaryl. Genetically encoded aromatic amino acids include Phe (F), Tyr (Y), and Trp (W).

"Basic Amino Acid" refers to a hydrophilic amino acid having a side chain pK value of greater than 7. Basic amino acids typically have positively charged side chains at physiological pH due to association with hydronium ion. Genetically encoded basic amino acids include His (H), Arg (R), and Lys (K).

As used herein, the term "binding" refers to the ability of a polypeptide to preferentially bind to target with an affinity that is at least two-fold greater than its affinity for binding to a non-specific target (e.g., BSA or casein) other than the predetermined target or a closely related target. The polypeptides provided herein bind their respective targets with an affinity with a KD value less than about $5 \times 10^{-5}$ M, more preferably less than about $2 \times 10^{-7}$ M, and most preferably less than about $1 \times 10^{-8}$ M$^-$. Similarly, "specific binding" refers to the property of a polypeptide to bind to a predetermined antigen with an affinity with a KD value less than about $2 \times 10^{-7}$ M$^-$.

The terms "binding interface residue" and "binding interface residues" refer to those residues of the polypeptide involved in target binding, which are exemplified in the representative polypeptide shown in Table 1 and Table 2.

As used herein, the phrase "blood half-life" refers to the time required for the plasma concentration of an agent to decline by one-half when elimination is first-order or pseudo-first order. In the case of multiple decay phases, the term "blood half life" refers to either the apparent half-life (if the decay half-lives for different phases are similar) or the dominant half-life (that accounting for the bulk of the clearance) if the different half-lives are dissimilar.

The terms "conservative variant" and "conservative variants" used herein apply to both amino acid and nucleic acid sequences. With respect to particular amino acid sequences, conservative variants refer to a sequence where certain amino acids have been replaced by similar amino acids from the same category, e.g. acidic, basic, polar, hydrophobic, hydrophilic, aromatic, and aliphatic as outlined above.

As used herein the term "disease management" refers to medical attention to disease conditions associated with PDGFR-β expression or disregulation that may be facilitated using the agents of the invention. Disease management includes decisions made by medical professionals regarding the course of treatment for a subject afflicted with an PDGFR-β associated diseases, including without limitation, the success or failure of a treatment, the status of the diseased tissue, and/or whether chemical or surgical intervention is indicated. Where surgical or other non-systemic intervention is indicated, disease management also includes spatial localization of the diseased tissue.

As used herein, the term "fluorophore" refers to a chemical compound, which when excited by exposure to a particular wavelength of light, emits light (at a different wavelength. Fluorophores may be described in terms of their emission profile, or "color." Green fluorophores (for example Cy3, FITC, and Oregon Green) may be characterized by their emission at wavelengths generally in the range of 515-540 nanometers. Red fluorophores (for example Texas Red, Cy5, and tetramethylrhodamine) may be characterized by their emission at wavelengths generally in the range of 590-690 nanometers. Examples of fluorophores include, but are not limited to, 4-acetamido-4'-isothiocyanatostilbene-2,2'disulfonic acid, acridine, derivatives of acridine and acridine isothiocyanate; 5-(2'-aminoethyl)aminonaphthalene-1-sulfonic acid (EDANS), 4-amino-N-[3-vinylsulfonyl)phenyl] naphthalimide-3,5 disulfonate (Lucifer Yellow VS), N-(4-anilino-1-naphthyl)maleimide, anthranilamide, Brilliant Yellow, coumarin, coumarin derivatives, 7-amino-4-methyl-coumarin (AMC, Coumarin 120), 7-amino-trifluoromethyl-couluarin (Coumaran 151), cyanosine; 4',6-diaminidino-2-phenylindole (DAPI), 5',5"-dibromopyrogallol-sulfonephthalein (Bromopyrogallol Red), 7-diethylamino-3-(4'-isothiocyanatophenyl)-4-methylcoumarin, -, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), eosin, derivatives of eosin such as eosin isothiocyanate, erythrosine, derivatives of erythrosine such as erythrosine B and erythrosin isothiocyanate; ethidium; fluorescein and derivatives such as 5-carboxyfluorescein (FAM), 5-(4,6-dichlorotriazin-2-yl) aminofluorescein (DTAF), 2'7'-di methoxy-4'5'-dichloro-6-carboxyfluorescein (JOE), fluorescein, fluorescein isothiocyanate (FITC), QFITC (XRITC); fluorescamine derivative (fluorescent upon reaction with amines); IR144; IR1446; Malachite Green isothiocyanate; 4-methylumbelliferone; ortho cresolphthalein; nitrotyrosine; pararosaniline; Phenol Red, B-phycoerythrin; o-phthaldialdehyde derivative (fluorescent upon reaction with amines); pyrene and derivatives such as pyrene, pyrene butyrate and succinimidyl 1-pyrene butyrate; Reactive Red 4 (Cibacron® Brilliant Red 3B-A), rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl Rhodamine, tetramethyl rhodamine isothiocyanate (TRITC); riboflavin; rosolic acid and lathanide chelate derivatives, quantum dots, cyanines, and squaraines.

As used herein the term "paramagnetic metal ion", "paramagnetic ion" or "metal ion" refers to a metal ion that is magnetized parallel or antiparallel to a magnetic field to an extent proportional to the field. Generally, these are metal ions that have unpaired electrons. Examples of suitable paramagnetic metal ions, include, but are not limited to, gadolinium III ($Gd^{3+}$ or Gd(III)), iron III ($Fe^{3+}$ or Fe(III)), manganese II ($Mn^{2+}$ or Mn(II)), yttrium III ($Yt^{3+}$ or Yt(III)), dysprosium ($Dy^{3+}$ or Dy(III)), and chromium (Cr(III) or $Cr^{3+}$). In some embodiments, the paramagnetic ion is the lanthanide atom Gd(III), due to its high magnetic moment (u 2=63BM2), a symmetric electronic ground state (S8), and its current approval for diagnostic use in mammals.

"Percentage of sequence identity" means the value determined by comparing two optimally aligned sequences over a comparison window, wherein the portion of the polynucleotide or polypeptide sequence in the comparison window may comprise additions, substitutions, or deletions (i.e., gaps) as compared to the reference sequence (which does not comprise additions, substitutions, or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

As used herein the term "physiological conditions" refers to conditions generally present in a mammalian body. Thus, physiological conditions mean a pH of about 6.5 to about 7.5 and temperature ranging from about 36° C. to about 39° C.

As used herein, the term "signal generator" refers to a molecule capable of providing a detectable signal using one or more detection techniques (e.g., spectrometry, calorimetry, spectroscopy, or visual inspection). Suitable examples of a detectable signal may include an optical signal, and electrical signal, or a radioactive signal. Examples of signal generators useful in the inventive methods include, for example, a chromophore, a fluorophore, a Raman-active tag, a radioactive label, an enzyme, an enzyme substrate, or combinations thereof. Suitable radioisotopes may include H-3, C-11, C-14, F-18, P-32, S-35, I-123, I-124, I-125, I-131, Cr-51, Cl-36, Co-57, Fe-59, Se-75, and Eu-152. Isotopes of halogens (such as chlorine, fluorine, bromine and iodine), and metals including technetium, yttrium, rhenium, and indium are also useful labels. Typical examples of metallic ions that may be used as signal generators include Tc-99m, I-123, In-111, I-131, Ru-97, Cu-67, Ga-67, I-125, Ga-68, As-72, Zr-89, Gd-153 and TI-201. Radioisotopes for in vivo diagnostic imaging by positron emission tomography ("PET") include C-11, F-18, Ga-68 and I-124. Paramagnetic labels may be metal ions are present in the form of metal complexes or metal oxide particles. Suitable paramagnetic isotopes may include Gd-157, Mn-55, Dy-162, Cr-52, and Fe-56.

"Hydrophilic Amino Acid" refers to an amino acid exhibiting a hydrophobicity of less than zero according to the normalized consensus of the Eisenberg hydrophobicity scale. Genetically encoded hydrophilic amino acids include Thr (T), Ser (S), His (H), Glu (E), Asn (N), Gln (O), Asp (D), Lys (K), and Arg (R).

"Hydrophobic Amino Acid" refers to an amino acid exhibiting a hydrophobicity of greater than zero according to the normalized consensus hydrophobicity Eisenberg scale. Genetically encoded hydrophobic amino acids include Pro (P), Ile (I), Phe (F), Val (V), Leu (L), Trp (W), Met (M), Ala (A), Gly (G) and Tyr (Y).

"Nonpolar Amino Acid" refers to a hydrophobic amino acid having a side chain that is uncharged at physiological pH and which has bonds in which the pair of electrons shared in common by two atoms is generally held equally by each of the two atoms (i.e., the side chain is not polar). Genetically encoded apolar amino acids include Leu (L), Val (V), Ile (I), Met (M), Gly (G), and Ala (A).

The phrase "parenteral administration" refers to any means of introducing a substance or compound into a subject, that does not involve oral ingestion or direct introduction to the gastrointestinal tract, including but not limited to subcutaneous injection, intraperitoneal injection, intramuscular injection, intravenous injection, intrathecal injection, intracerebral injection, intracerebroventricular injection, or intraspinal injection, or any combination thereof.

As used herein, the phrase "PDGRF-β-associated pathology" generally refers to any condition in which the expression pattern of as PDGRF-β is causative of or associated with a syndrome, disease, or other pathological condition, such as, but not limited to liver fibrosis, cirrhosis or abnormal liver function, or any combination thereof.

"Polar Amino Acid" refers to a hydrophilic amino acid having a side chain that is uncharged at physiological pH, but which has at least one bond in which the pair of electrons shared in common by two atoms is held more closely by one of the atoms. Polar amino acids include Asn (N), Gln (O), Ser (S), and Thr (T).

The term "scaffold" with reference to helical polypeptides generally refers to those residues of the polypeptide that provides the three-dimensional structure to adequately position the binding interface residues of the polypeptide such that binding to a target is enabled.

As used herein, the term "signal generator" refers to a molecule capable of providing a detectable signal using one or more detection techniques including, for example, spectrometry, calorimetry, spectroscopy, or visual inspection.

As used herein, the term "activating group" refers to any group that makes a carbonyl group more reactive towards nucleophiles (e.g. N-hydroxysuccinimide, sulfo-N-hydroxysuccinimide, acid chloride, urea intermediates).

As used herein, the term "aldehyde-reactive terminus" refers to any functional group that can react with an aldehyde functional group. Some examples of aldehyde-reactive functional groups include, but are not limited to, —$ONH_2$, —$CONHNH_2$, —$NHNH_2$, —$NHCONH_2$, and —$NHCSNH_2$. The aldehyde-reactive functional group may also be a protected derivative that may either be deprotected prior to reaction with the aldehyde, or deprotected in situ during the reaction with the aldehyde. Some examples of protecting groups for the aldehyde-reactive terminus include alkyloxycarbonyl groups, aryloxycarbonyl groups, cycloalkyloxycarbonyl groups, alkylsulfonyl groups, arylsulfonyl groups, cycloalkylsulfonyl groups, and phosphinoyl groups. Some specific examples of protecting groups for aldehyde-reactive terminus include tert-butyloxycarbonyl, triphenylmethyl; 9-fluorenylmethylcarbonyl, benzyloxycarbonyl, 4-methoxybenzyloxycarbonyl, 4-azidobenzylcarbamate, 4-nitrobenzyloxycarbonyl, 9-fluorenylmethoxycarbonyl; 2,4-dinitrobenzenesulfonyl; and diphenylphosphinoyl.

As used herein, the term "aliphatic radical" or "aliphatic group" generally refers to an array of carbon atoms that is not cyclic and has a point of attachment that is an $sp^3$ carbon atom. The array of carbon atoms may further comprise any combination of $sp^3$, $sp^2$, or sp hybridized carbon atoms. Further, the array of carbon atoms may be monovalent, divalent, or trivalent. Examples of alkyl groups include methyl, ethyl, n-propyl, isopropyl, n-butyl, tert-butyl, isooctyl, benzyl, cyclohexylmethyl, phenethyl, 1',1'-dimethylbenzyl, and the like.

As used herein the term "ambient temperature" refers to temperature generally present in a clinical or laboratory setting. Thus, ambient temperature may range from about 0° C. to about 37° C.

As used herein, the terms "aromatic radical" or and "aromatic group" refers to a cyclic array of $sp^2$ hybridized carbon atoms and conjugated carbon-carbon double bonds, and has a point of attachment at an aromatic $sp^2$ hybridized carbon atom that forms part of the cyclic array of carbon atoms. The aromatic group or radical may have from one to the maximum permissible number of substituents. Examples of aryl groups include phenyl, substituted phenyl, tolyl, substituted tolyl, xylyl, mesityl, chlorophenyl, naphthyl, furyl, thienyl, pyrrolyl, and the like.

As used herein, the term "cycloalkyl radical" or a "cycloalkyl group" refers to a cyclic array of $sp^3$ hybridized carbon atoms, and has a point of attachment at an $sp^3$ hybridized carbon atom that forms part of the cyclic array of carbon atoms. The array of carbon atoms may further comprise any combination of $sp^3$, $sp^2$, or sp hybridized carbon atoms. Further, the cyclic array of carbon atoms may be substituted with one to the maximum permissible number of substituents. Furthermore, the array of cyclic atoms may comprise heteroatoms, such as O, N, or S. Examples of cycloalkyl groups include cyclohexyl, methylcyclohexyl, trimethylcyclohexyl, phenylcyclohexyl, tetrahydropyranyl, 4-thiacyclohexyl, cyclooctyl, and the like.

The terms "radical" and "group", as applied to the terms "alkyl", "aliphatic", "cycloaliphatic", and "aromatic" are used interchangeably herein.

As used herein, the term "substitution" refers generally to the replacement of one or more elements or radicals as a result of a chemical reaction. Suitable substituents include alkyl, alkylaryl, aryl, arylalkyl, and heteroaryl groups, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy groups.

As used herein the term "thiol-reactive terminus" refers to a functional group that may react with a thiol group or a mercaptan group (i.e., —SH group). Examples of thiol-reactive functional groups include, but are not limited to a maleimido group, a haloaliphatic group, a haloaromatic group, a halocycloaliphatic group, a (haloacetyl)alkyl group, a (haloacetyl)cycloalkyl group, a (haloacetyl)aryl group, an α, β-unsaturated sulfone group, a vinyl sulfone group, an α, β-unsaturated carbonyl group, an epoxy group, an aziridine group, and a disulfide group capable of a thiol exchange reaction with a thiol group.

The term "a disulfide group capable of a thiol exchange reaction with a thiol group" refers to groups that may react with a thiol group of a biomolecule, such as a thiol group of a polypeptide. Thus, a disulfide may be regarded as a thiol-reactive group. Pyridyl disulfide is a suitable example of such a disulfide. Suitable maleimido groups include the parent (unsubstituted) group as well as derivatives comprising aliphatic, cycloaliphatic or aromatic groups as substituents. Suitable α, β-unsaturated carbonyl groups include those comprising an acryloyl group. Suitable α, β-unsaturated carbonyl groups include α, β-unsaturated esters and α, β-unsaturated sulfones. Vinyl sulfone group is a specific example of an α, β-unsaturated sulfone group.

As used herein, the term "fluorine-substituted aldehyde" denotes an aldehyde-containing compound having at least one fluorine substituent. Further, the fluorine substituent may be of any isotopic variety, such as for example, F-18 and F-19. Further, the aldehyde may be an aliphatic aldehyde, a cycloaliphatic aldehyde, or an aromatic aldehyde. Furthermore, the cycloaliphatic aldehydes and aromatic aldehydes may have monocyclic, bicyclic, or polycyclic structures.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

EMBODIMENTS

In general, when used as a detection agent, the polypeptides binding PDGF-R may be modified to generate a signal by the addition of a label (e.g., a fluorophore or a radioisotope).

The binding polypeptides may be generated using standard solid phase synthesis techniques. Alternatively, the polypeptides may be generated using recombinant techniques. In embodiments where the polypeptides are generated using recombinant techniques, the DNA encoding the polypeptides or conservative variants thereof may be isolated. The DNA encoding the polypeptides or conservative variants thereof may be inserted into a cloning vector, introduced into a host cell (e.g., a eukaryotic cell, a plant cell, or a prokaryotic cell), and expressed using any art recognized expression system.

Whether the polypeptide is generated using peptide synthesis techniques or recombinant techniques, the polypeptides generated may be substantially comprised of a single chiral form of amino acid residues. Thus, polypeptides of the invention may be substantially comprised either L-amino acids or D-amino acids; although a combination of L-amino acids and D-amino acids may also be employed.

As the polypeptides provided herein are derived from the Z-domain of protein A, residues on the binding interface may be conservatively substituted while preserving binding activity. In some embodiments, the substituted residues may be any of the 20 naturally occurring amino acids or any of analog thereof.

The polypeptides provided herein consist essentially of polypeptides between 49 and 71 residues in length. The length of the polypeptides may be about 49 residues to about 130 residues.

TABLE 1

| Name | Sequence | Length |
|---|---|---|
| SEQ. ID NO. 1 | KERQVAAAEIDALPNLNRGQWNAF IASLVDDPSQSANLLAEAKKLNDAQ | 49 |
| SEQ. ID NO. 2 | KELSDAAQEIDSLPNLNRSQWNAFI KSLIDDPSQSANLLAEAKKLNDAQ- | 49 |
| SEQ. ID NO. 3 | KERREAAKEIDSLPNLNRTQWNAFI RSLADDPSQSANLLAEAKKLNDAQ | 49 |
| SEQ. ID NO. 4 | KELVRAAQEIDELPNLNRGQWNAFI KSLVDDPSQSANLLAEAKKLNDAQ | 49 |
| SEQ. ID NO. 5 | KELIAAAAEIDRLPNLNRVQWNAFIK SLVDDPSQSANLLAEAKKLNDAQ | 49 |
| SEQ. ID NO. 6 | KELIEAAAEIDALPNLNRRQWNAFIK SLVDDPSQSANLLAEAKKLNDAQ | 49 |
| SEQ. ID NO. 7 | KELVRAAEEIDNLPNLNRKQWNAFI KSLVDDPSQSANLLAEAKKLNDAQ | 49 |
| SEQ. ID NO. 8 | KELVKAAAEIDALPNLNRRQWNAFI KSLVDDPSQSANLLAEAKKLNDAQ | 49 |
| SEQ. ID NO. 9 | KELIEAAAEIDALPNLTRRQWNAF IKKLVDDPSQSSELLSEAKK LNDSQ | 49 |

TABLE 2

| Name | | Sequence | Length |
|---|---|---|---|
| Ztaq (SEQ. ID NO. 10) | control | GSSHHHHHHYYLEVDNKFNKELG WATWEIFNLPNLNGVQVKAFIDSLR DDPSQSANLLAEAKKLNDAQAPKV DC | 74 |

TABLE 2-continued

| Name | Sequence | Length |
|---|---|---|
| Z1977 (SEQ. ID NO. 11) | GSSHHHHHHLQVDNKFNKERQVA AAEIDALPNLRGQWNAFIASLVDD PSQSANLLAEAKKLNDAQAPKVDC | 72 |
| Z1978 (SEQ. ID NO. 12) | GSSHHHHHHLQVDNKFNKELSDAA QEIDSLPNLNRSQWNAFIKSLIDDP SQSANLLAEAKKLNDAQAPKVDC | 72 |
| Z1980 (SEQ. ID NO. 13) | GSSHHHHHHLQVDNKFNKERREA AKEIDSLPNLNRTQWNAFIRSLADD PSQSANLLAEAKKLNDAQAPKVDC | 72 |
| Z1982 (SEQ. ID NO. 14) | GSSHHHHHHLQVDNKFNKELVRAA QEIDELPNLNRGQWNAFIKSLVDDP SQSANLLAEAKKLNDAQAPKVDC | 72 |
| Z1995 (SEQ. ID NO. 15) | GSSHHHHHHLQVDNKFNKERLKAA AEIDALPNLRKQWNAFISSLRDDP SQSANLLAEAKKLNDAQAPKVDC | 72 |
| Z2465 (SEQ. ID NO. 16) | GSSHHHHHHLQVDNKFNKELIEAA AEIDALPNLNRRQWNAFIKSLVDDP SQSANLLAEAKKLNDAQAPKVDC | 72 |
| Z2516 (SEQ. ID NO. 17) | GSSHHHHHHLQVDNKFNKELVRAA EEIDNLPNLNRKQWNAFIKSLVDDP SQSANLLAEAKKLNDAQAPKVDC | 72 |
| Z2483 (SEQ. ID NO. 18) | GSSHHHHHHLQVDNKFNKELVKAA AEIDALPNLNRRQWNAFIKSLVDDP SQSANLLAEAKKLNDAQAPKVDC | 72 |
| (Z2465)$_2$ (SEQ. ID NO. 19) | GSSHHHHHHLQVDNKFNKELIEAA AEIDALPNLNRRQWNAFIKSLVDDP SQSANLLAEAKKLNDAQAPKVDNK FNKELIEAAAEIDALPNLNRRQWNA FIKSLVDDPSQSANLLAEAKKLNDA QAPKVDC | 130 |
| (Z2516)$_2$ (SEQ. ID NO. 20) | GSSHHHHHHLQVDNKFNKELVRAA EEIDNLPNLNRKQWNAFIKSLVDDP SQSANLLAEAKKLNDAQAPKVDNK FNKELVRAAEEIDNLPNLNRKQWN AFIKSLVDDPSQSANLLAEAKKLND AQAPKVDC | 130 |
| (Z2483)$_2$ (SEQ. ID NO. 21) | GSSHHHHHHLQVDNKFNKELVKAA AEIDALPNLNRRQWNAFIKSLVDDP SQSANLLAEAKKLNDAQAPKVDNK FNKELVKAAAEIDALPNLNRRQWN AFIKSLVDDPSQSANLLAEAKKLND AQAPKVDC | 130 |
| (Z2477)$_2$ (SEQ. ID NO. 22) | GSSHHHHHHLQVDNKFNKELIAAA AEIDRLPNLNRVQWNAFIKSLVDDP SQSANLLAEAKKLNDAQAPKVDNK FNKELIAAAEIDRLPNLNRVQWNA FIKSLVDDPSQSANLLAEAKKLNDA QAPKVDC | 130 |
| Z02465 (SEQ. ID NO. 23) | GSSLQVDNKFNKELIEAAAEIDALP NLNRRQWNAFIKSLVDDPSQSANL LAEAKKLNDAQAPKVDC | 66 |
| Z03358 (SEQ. ID NO. 24) | AEAKYAKELIEAAAEIDALPNLTRRQ WNAFIKKLVDDPSQSSELLSEAKKL NDSQAPSC | 59 |
| Z2477 (SEQ. ID NO. 25) | GSSHHHHHHLQVDNKFNKELIAAA AEIDRLPNLNRVQWNAFIKSLVDDP SQSANLLAEAKKLNDAQAPKVDC | 72 |

Table 3 (below) provides binding affinity measurements for selected polypeptides toward human PDGF-R beta and mouse PDGF-R beta as well as the isoelectric point (pI), relevant towards labeling conditions, of those polypeptides.

TABLE 3

|  | Affinity (human) | Affinity (mouse) | pI | MW (kD) |
|---|---|---|---|---|
| Ztaq (SEQ. ID NO. 10) | None (neg. control) | None (neg. control) | 6.5 | 8321 |
| Z1982 (SEQ. ID NO. 14) | 4 nM | 27 nM | 6.8 | 7987 |
| Z2465 (SEQ. ID NO. 16) | 500 pM | 7 nM | 6.29 | 8186 |
| Z2477 (SEQ. ID NO. 25) | <1 nM | N/A | 6.63 | 8156 |
| Z2483 (SEQ. ID NO. 18) | 400 pM | 6 nM | 7.19 | 8171 |
| Z2516 (SEQ. ID NO. 17) | <1 nM | N/A | 6.64 | 8272 |
| Z(2465)$_2$ (SEQ. ID NO. 19) | <500 pM | <7 nM | 6.06 | 14616 |

Additional sequence may be added to the termini to impart selected functionality. Thus, additional sequences may be appended to one or both termini to facilitate purification or isolation of a PDGF-R binder, alone or coupled to a binding target (e.g., by appending a his tag to the polypeptide).

A signal generator may be incorporated into the polypeptide at terminal position or at an internal position. Suitable examples of signal generators may include a chromophore, a fluorophore, a Raman-active tag, a radioactive label, an enzyme, an enzyme substrate, or combinations thereof. Suitable examples of a detectable signal may include an optical signal, and electrical signal, or a radioactive signal.

In some embodiments of the invention, a radiometal may be chelated by certain residues in the polypeptide, e.g. Tc-99m contained in an N3S chelator formed by a cysteine thiol together with backbone amine groups of the cysteine and the two preceding residues.

A linker may be appended to the polypeptide to facilitate linkage to a separate chemical entity (e.g., a tag or a label). The polypeptidesdisclosed herein may be further modified to enhance pharmokinetics (e.g., by appending polyglycans to modulate blood circulation half life).

The linkers may be used to attach a thiol-containing compound at one end via the thiol-reactive terminus, and for attachment to aldehydes, especially fluorine-substituted aldehydes at the other end via the aldehyde-reactive terminus. Some examples of linkers are shown in structures (I)-(IV).

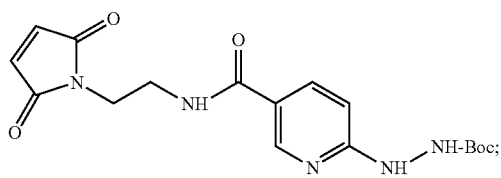

(I)

(II)

(III)

(IV)

where "Boc" is an abbreviation for the protecting group benzyloxycarbonyl.

In some embodiments, the thiol-reactive terminus, the aldehyde-reactive terminus, or both thiol-reactive terminus and the aldehyde-reactive terminus may be replaced with an analogous protected derivative. The linkers may be used to attach a thiol-containing compound at one end via the thiol-reactive terminus, and/or to attach aldehydes, (e.g., fluorine-substituted aldehydes) at the other end via the aldehyde-reactive terminus.

The linker may be prepared by any method that makes both the thiol-reactive group and the aldehyde-reactive group accessible for reaction with (i) the polypeptide having at least one thiol group, and (ii) the fluorine-substituted aldehyde, respectively. In one embodiment, the linker is prepared by reacting an amine compound comprising a thiol-reactive functional group with a carboxylic acid or an activated ester comprising an aldehyde-reactive functional group. Any amine compound having a thiol-reactive functional group may be used. In an embodiment, the amine compound comprises a structure (V),

G-J-NHR1 (V)

wherein G is a thiol-reactive functional group, J is a linking unit, and R1 is H, an aliphatic radical, an aromatic radical, or a cycloaliphatic radical. The nature of the divalent linking unit J may be designed to minimize steric hindrance, which could adversely affect the reactivity of the thiol-reactive and the aldehyde-reactive functional groups. One of the advantages of the present approach is that the linking unit may be tailored to alter the final properties of the bioconjugate. Thus, the linkers may vary in size, polarity, charge, and chemical composition to modify properties of the final conjugates, such as solubility and PK/PD properties. Furthermore, the linkers may include additional handles for attachment of groups that would improve targeting and/or solubility.

In other embodiments, the linker may be prepared by reacting an amine compound comprising an aldehyde-reactive group with a carboxylic acid or an activated ester compound comprising a thiol-reactive functional group.

The activated ester comprises a structure (VI),

L-M-COR2 (VI)

wherein L comprises an aldehyde-reactive functional group, a ketone-reactive functional group, or a protected derivative thereof; M is a divalent linking unit, and R2 is OH or an activating group. The activating group R2 facilitates the reaction of the amine compound having the thiol group with the carbonyl carbon atom of structure (VI). Exemplary synthetic approaches for preparing the linker having structure (X) are shown in Schemes 1 and 2.

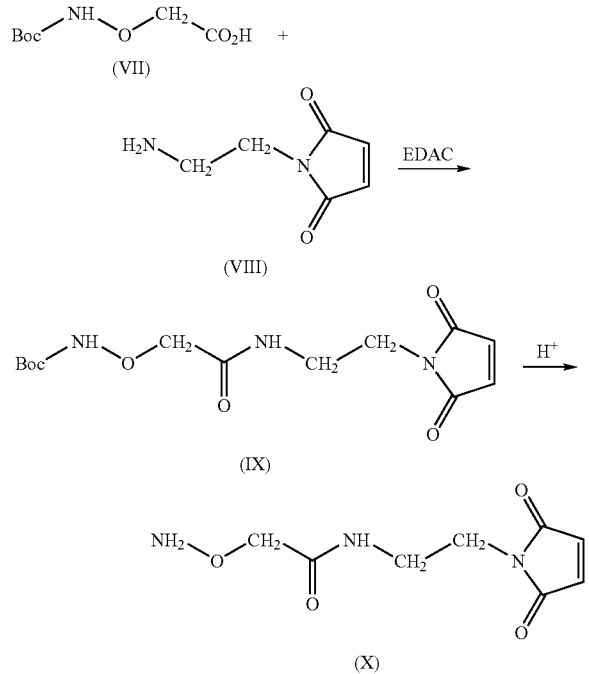

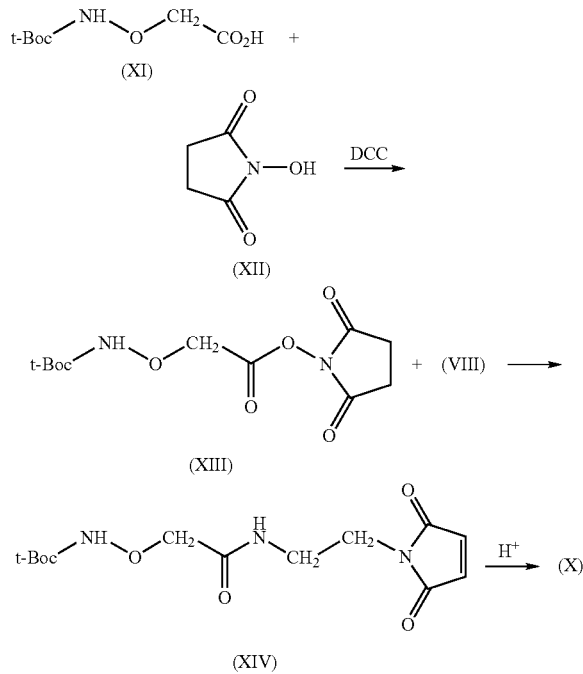

In Scheme 1, EDAC stands for 1-Ethyl-3-(3-dimethylaminopropyl)carbodiimide and in Scheme 2, DCC stands for dicyclohexyl carbodiimide. Some examples of linkers that may be prepared using these methods are shown above in structures (I) and (II).

The aldehyde-reactive terminus of the linker may either be present in a protected form or an un-protected form. In some particular embodiments, the aldehyde-reactive terminus is selected from $-ONH_2$, $-CONHNH_2$, $-NHNH_2$, $-NHCONH_2$, and $-NHCSNH_2$. In an embodiment, the aldehyde-reactive terminus is present in the protected form since this may allow for a cleaner and more selective reaction of the thiol-reactive terminus with the thiol group of the polypeptide. Examples of suitable protecting groups for the aldehyde-reactive terminus include, but are not limited to tert-butoxycarbonyl, triphenylmethyl, 9-fluorenylmethylcarbonyl, benzyloxycarbonyl, 4-methoxybenzyloxycarbonyl, 4-azidobenzylcarbamate, 4-nitrobenzyloxycarbonyl, 9-fluorenylmethoxycarbonyl, 4-dinitrobenzenesulfonyl, and diphenylphosphinoyl groups.

The methods described herein enable the preparation of fluorine-labeled bioconjugates, more particularly radiofluorine (e.g., F-18) labeled bioconjugates. One of the advantages of these methods is that the linker may be attached selectively to a biomolecule such as a polypeptide under non-radioactive conditions in which the thiol group of the polypeptide may be reacted selectively with the thiol-reactive group of the linker, and the resulting bioconjugate may be purified prior to reaction with an F-18 or a normal fluorine-substituted aldehyde. Another advantage is that the radiofluorine label may be added selectively in a final step, eliminating the need for time consuming additional purification steps before the preparation of the final bioconjugate, especially at tracer levels.

In one aspect, methods for introducing one or more fluorine atom(s) onto a polypeptide are disclosed. The methods may comprise: (i) providing a linker comprising a thiol-reactive terminus and an aldehyde-reactive terminus; (ii) reacting the thiol-reactive terminus of the linker with a polypeptide comprising at least one thiol group or a reactive derivative thereof; and (iii) subsequently reacting the aldehyde-reactive terminus of the linker with a fluorine-substituted aldehyde.

In some embodiments of the methods for introducing the fluorine atom onto the polypeptide, the thiol-reactive terminus of the linker is selected from a maleimido group, a haloaliphatic group, a haloaromatic group, a halocycloaliphatic group, a (haloacetyl)alkyl group, a (haloacetyl)cycloalkyl group, a (haloacetyl)aryl group, a vinyl sulfone group, an acryloyl group, an epoxy group, an aziridine group, and a disulfide group capable of a thiol exchange reaction with a thiol group. [Maureen—these are not claimed specifically, but only generally, included in the examples, so how do we deal with the language here?]

More specifically, the methods described herein may be employed to introduce one or more fluorine atoms onto a polypeptide using 2-(aminooxy)-N-(2-(2,5-dioxo-2,5-dihydro-1H-pyrrol-1-yl)ethyl)acetamide as the linker. Such methods comprise: (i) reacting the thiol-reactive group of 2-(aminooxy)-N-(2-(2,5-dioxo-2,5-dihydro-1H-pyrrol-1-yl)ethyl)acetamide with a polypeptide comprising at least one thiol group; and (ii) subsequently reacting the aminooxy group of the intermediate product resulting from step (i) with a fluorine-substituted aldehyde. [Maureen—these are not claimed specifically, but only generally, included in the examples, so how do we deal with the language here?]

When a linker having a protected form of the aldehyde-reactive terminus is used, subsequent reaction with the fluorine-substituted aldehyde may be carried out, in an embodiment, by (i) deprotecting the aldehyde-reactive terminus, and (ii) reacting the deprotected aldehyde-reactive terminus with the fluorine-substituted aldehyde. In other embodiments, the user may choose reaction conditions for the reaction of the protected aldehyde-reactive terminus with the fluorine-substituted aldehyde so that the deprotection step occurs in situ.

The reaction of the aldehyde-reactive terminus of the linker with the fluorine-substituted aldehyde may be carried out in any medium that may range from about neutral to acidic. In an embodiment, the reaction may be conducted in a medium having a pH in a range from about 2 to about 7; and in another embodiment, in a pH range from about 2 to about 5. The reaction temperature may be varied from ambient temperature to about 70° C. Reaction time may vary, but generally may be from about 10 minutes to about 60 minutes. In some embodiments, the reaction time varies from about 10 minutes to about 30 minutes. However, longer reaction times may also be employed.

The products resulting from the reaction of the linker with the polypeptide having at least one thiol group is termed as a bioconjugate. Thus in an embodiment, the bioconjugate comprises structural units derived from: (i) a polypeptide comprising at least one thiol group; and (ii) a linker; where the linker is prepared by a method comprising reacting an amine compound comprising a thiol-reactive functional group with an activated ester comprising an aldehyde-reactive functional group. Scheme 3 shows two possible approaches to prepare the bioconjugate (XVII).

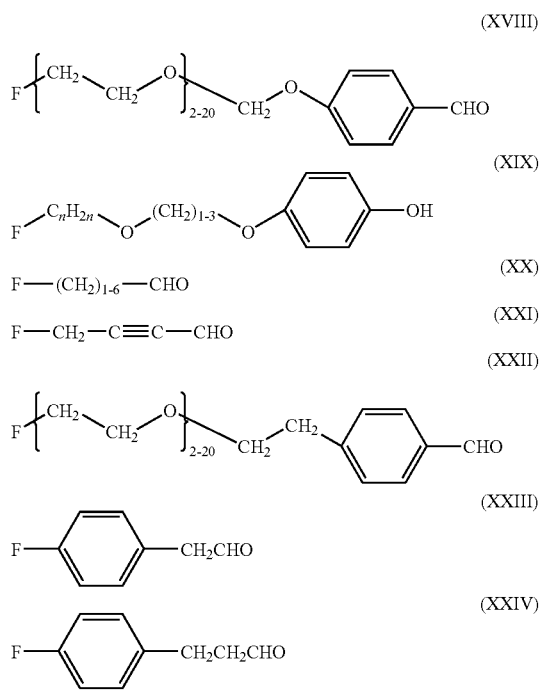

Scheme 3

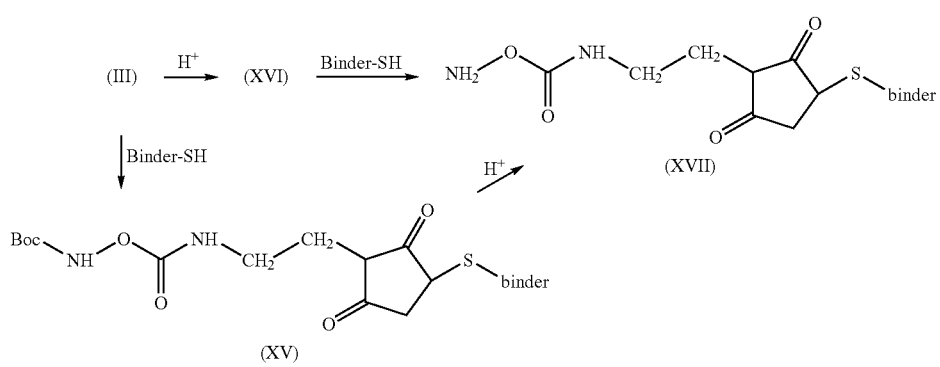

In one approach, the Boc-protected linker may be first reacted with a polypeptide comprising a thiol group and the resulting Boc-protected intermediate (XXV) is deprotected to give the desired bioconjugate (XXVII). Alternatively, the Boc-protected linker may be first deprotected to give linker (XVI), which may then be reacted with the polypeptide comprising the thiol group to give product (XXVII).

Using the above-described techniques, one may introduce fluorine or radiofluorine atom(s), such as F-18, onto polypeptides. When a fluorine-substituted aldehyde is reacted with a bioconjugate, a fluorine-substituted bioconjugate results. And, when a radiofluorine-substituted aldehyde is reacted with bioconjugate, a radiofluorine-labeled bioconjugate results. A non-limiting set of suitable fluorine-substituted aldehydes are shown in structures (XVIII)-(XXVIII). Fluorodeoxyglucose (FDG) or F-18 labeled FDG may also be used for preparing fluorine substituted radiolabeled bioconjugates. Further, each of these aldehydes may have a radiofluorine (F-18) substituent, enabling preparation of the corresponding radiofluorine-labeled bioconjugates.

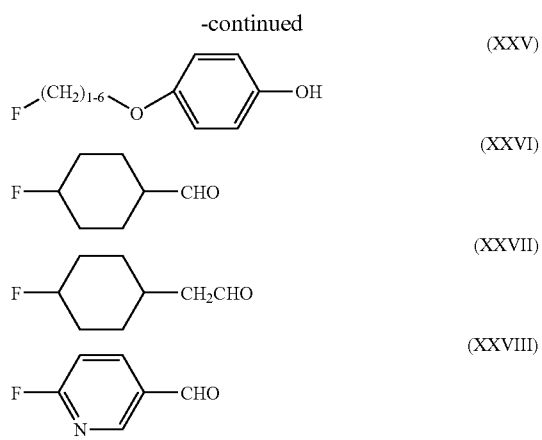

Any of the polypeptides described previously having at least one thiol group may be used for preparing the bioconjugates. Polypeptides such as scaffold-based proteins and engineered binding proteins having at least one thiol group are especially valuable since such materials have potentially valuable diagnostic and therapeutic value. Thus in an embodiment, valuable bioconjugates may be produced by reacting scaffold-based proteins such as affibodies with 2-(aminooxy)-N-(2-(2,5-dioxo-2,5-dihydro-1H-pyrrol-1-yl)ethyl)acetamide linker. Further, valuable fluorine-labeled bioconjugates may be produced by reacting the bioconjugate with a fluorine-substituted aldehyde.

The fluorine-labeled bioconjugates are valuable materials in diagnostic applications. F-18 labeled bioconjugates may be visualized using imaging techniques known in the art, such as for example PET (positron emission tomography)

The techniques disclosed herein also provide a broad general approach to produce various types of linkers that may or may not have a chelating group. As will be evident from the Examples provided further below, the methods for forming the linkers having structures (I) and (II), which do not have a chelating group may also be used for forming linkers comprising chelating groups, such as for example structures (III) and (IV). Further, the linkers comprising chelating groups may be reacted with suitable polypeptides comprising a thiol group to form bioconjugates. These bioconjugates may then be complexed with various types of radioactive metals, such as for example, Cu-64, Ga-67, Ga-68, Zr-89, Ru-97, Tc-99m, Tc-94m, Rh-105, Pd-109, In-111, Re-186, Re-188, Au-198, Au-199, Pb-203, At-211, Gd-153 or Bi-212 for imaging applications. Where are structures (I), (II), (III) and (IV)?

The compositions disclosed herein may be administered to humans and other animals parenterally. Pharmaceutical compositions of this invention for parenteral injection comprise pharmaceutically-acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

These compositions may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents such as sugars, sodium chloride, and the like. Prolonged absorption of the injectable pharmaceutical form may be brought about by the inclusion of agents, which delay absorption such as aluminum monostearate and gelatin.

The disclosed agents may be dispersed in physiologically acceptable carrier to minimize potential toxicity. Thus, the agents of the present invention may be dispersed in a biocompatible solution with a pH of about 6 to about 8. In some embodiments, the agent is dispersed in a biocompatible solution with a pH of about 7 to about 7.4. In other embodiments, the agent is dispersed in a biocompatible solution with a pH of about 7.4.

The disclosed agents may be combined with additives that are commonly used in the pharmaceutical industry to suspend or dissolve the compounds in an aqueous medium, and then the suspension or solution can be sterilized by techniques known in the art. The agents of the present invention or their pharmaceutically acceptable salts can be administered to the subject in a variety of forms adapted to the chosen route of administration. Thus, the disclosed agents may be topically (i.e., by the administration to the tissue or mucus membranes), intravenously, intramuscularly, intradermally, or subcutaneously. Forms suitable for injection include sterile aqueous solutions or dispersions and sterile powders for the preparation of sterile injectable solutions, dispersions, liposomal, or emulsion formulations. In all cases, the form must be sterile and should be fluid to enable administration by a syringe. Forms suitable for inhalation use include agents dispersed in a sterile aerosol. Forms suitable for topical administration include creams, lotions, ointments, and the like.

In some embodiments, the agents of the invention are concentrated to conveniently deliver a preferred amount of the agents to a subject and packaged in container in the desired form. Thus, in some embodiments the agent is dispensed in a container dispersed in physiologically acceptable solution, that conveniently facilitates administering the agent in concentrations between 0.1 mg and 50 mg of the agent per kg body weight of the subject.

The target tissue is imaged less than or approximately 3 hours after administering the agents. In alternative embodiments, the target tissue is imaged less than or approximately 24 hours after administering to the subject the agents.

In another series of embodiments, the present invention provides for methods of imaging PDGFR-β-associated diseases. The methods of managing conditions associated PDGFR-β may include imaging the target tissue before, after, or both before and after treating the subject to treat or ameliorate the symptoms of the PDGFR-β-associated diseases. Thus, the disclosed methods of PDGFR-β-associated diseases may include (a) imaging the target tissue to obtain base-line or diagnostic information, (b) treating the subject, and (c) imaging the subject a one or more times to obtain further information about the disease condition.

A medical professional may opt not to image the subject both before and after treatment, relying on other techniques to initially characterize the diseased tissue or subsequently assess the diseased tissue. Thus, in an alternative embodiment, the methods of managing conditions associated with PDGFR-β includes treating the disease condition that was identified by a technique not emplying the disclosed agents imaging the target issue subsequent to treatment. Likewise, in another alternative embodiment, the disclosed methods of managing conditions may include imaging a subject or target tissue followed by treatment without subsequently re-imaging the target tissue.

When the disease management is directed to determining the efficacy of a treatment, the methods comprise imaging the tissue of interest before administration of a treatment to obtain a pre-treatment assessment, followed by administration of the treatment and imaging the tissue of interest one or more times subsequent to the treatment to obtain a post-treatment assessment of the tissue of interest. The pre-treatment assessment and the post-treatment assessment(s) may be compared to determine the efficacy of the treatment.

When the disease management includes treatments that are localized to the diseased tissue rather than a holistic or systemic administration of treatment (e.g., surgical or radiological intervention), the disease management methods may include using the disclosed agents to determine the spatial localization of the diseased tissue to define the specific area to be treated (e.g., excised or irradiated).

EXAMPLES

Practice of the invention will be still more fully understood from the following examples, which are presented herein for illustration only and should not be construed as limiting the invention in any way.

In Vitro and In Vivo Models to Study Binderss

To carry out in vivo studies, we developed an animal model that reliably expresses high levels of PDGF-Rβ. Tumor xenograft models were chosen because they allow the possibility of using a model expressing the human target. One clear advantage of a xenograft with human cells is that the results from a model expressing the human target would more relevant to human systems than those for the murine target.

A panel of tumorigenic cell lines with a reasonable probability of expressing PDGF-Rβ was selected based on available literature on (Bronzer et al, 1987; Strawn et al, 1994; Khana et al, 2001; Fitzer-Attas et al, 1993). Along with positive and negative controls, this panel was used to find suitable cell lines for in vivo experimentation (Table 4).

TABLE 4

| Cell line | Species | Type | Purpose | Tumorigenic |
|---|---|---|---|---|
| 3T3 | Mouse | Fibroblast | +control | No |
| C6 | Rat | Glioma | Candidate | Yes |
| LLC | Mouse | Lung carcinoma | Candidate | Yes |
| K7M2 | Mouse | Osteosarcoma | Candidate | Yes |
| A172 | Human | Brain glioblastoma | +control | No |
| U87 | Human | Brain glioblastoma | Candidate | Yes |
| MDA-MB-231 ("M231") | Human | Breast adenocarcinoma | Candidate | Yes |
| HT29 | Human | Colorectal adenocarcinoma | −control | Yes |
| LS174T | Human | Colorectal adenocarcinoma | candidate | Yes |

All cell lines were obtained from the American Type Culture Collection (ATCC) and cultured as recommended. Cells were cultured to >90% confluence prior to use.

Flow cytometry (Beckman Coulter Cytomics FC500 MPL) was carried out on the human-derived cell lines listed in table 3 using anti-hPDGF-Rβ primary antibodies (R&D Systems, PN Mab1263) and an anti-mouse IgG-Alexa488 secondary antibody (Invitrogen). Flow cytometry of the rodent cell lines listed in table 3 was carried out with an R&D systems primary antibody (anti-mPDGF-R β antibody Mab1042) and an Invitrogen secondary antibody (anti-mouse IgG-Alexa488), or a directly labeled primary anti-mCD140b-PE (Ebioscience). In all cases, appropriate isotype controls were obtained from the corresponding vendors.

Adherent cells were released from their flasks using cell dissociation buffer (PBS+10 mM EDTA) rather than trypsin to avoid proteolysis of cell surface receptors. Cells were washed twice in PBS and resuspended in ice-cold FC buffer (PBS+0.5% BSA w/v) to a concentration of $5\text{-}10 \times 10^6$ cells/ml. 200 ul aliquots of cells were mixed with 1.5 ug of primary antibody and incubated, on ice, for 45 minutes. Cells were then washed twice with 1 ml of ice cold PBS, and resuspended in 1 ml of flow cytometry (FC) buffer (PBS with 0.2% bovine serum albumin) for analysis in the case of directly labeled primaries, or in 100-200 ul of FC buffer for further staining with secondary antibodies. For flow cytometry experiments performed with a primary-secondary antibody combination, 3 ug of secondary antibody was added to each tube and cells were incubated on ice for 30 minutes, washed twice, and resuspended in 1 ml of FC buffer for analysis. All stained cells were passed through a 100-micron filter prior to flow cytometry to prevent clogs of the flow cell. LS174T cells, which clumped extensively during staining, could not be readily put through this filter.

Flow Cytometry

Flow cytometry was carried out on a Beckman Coulter Cytomics FC500 MPL. A minimum of $5 \times 10^4$ events was collected for each tube. All analyses were single color, with detection of Alexa-488 in FL1, or detection of PE in FL2. Forward scatter (FS) and side scatter (SS) data demonstrated that all cell populations were tightly grouped.

Figure 3:
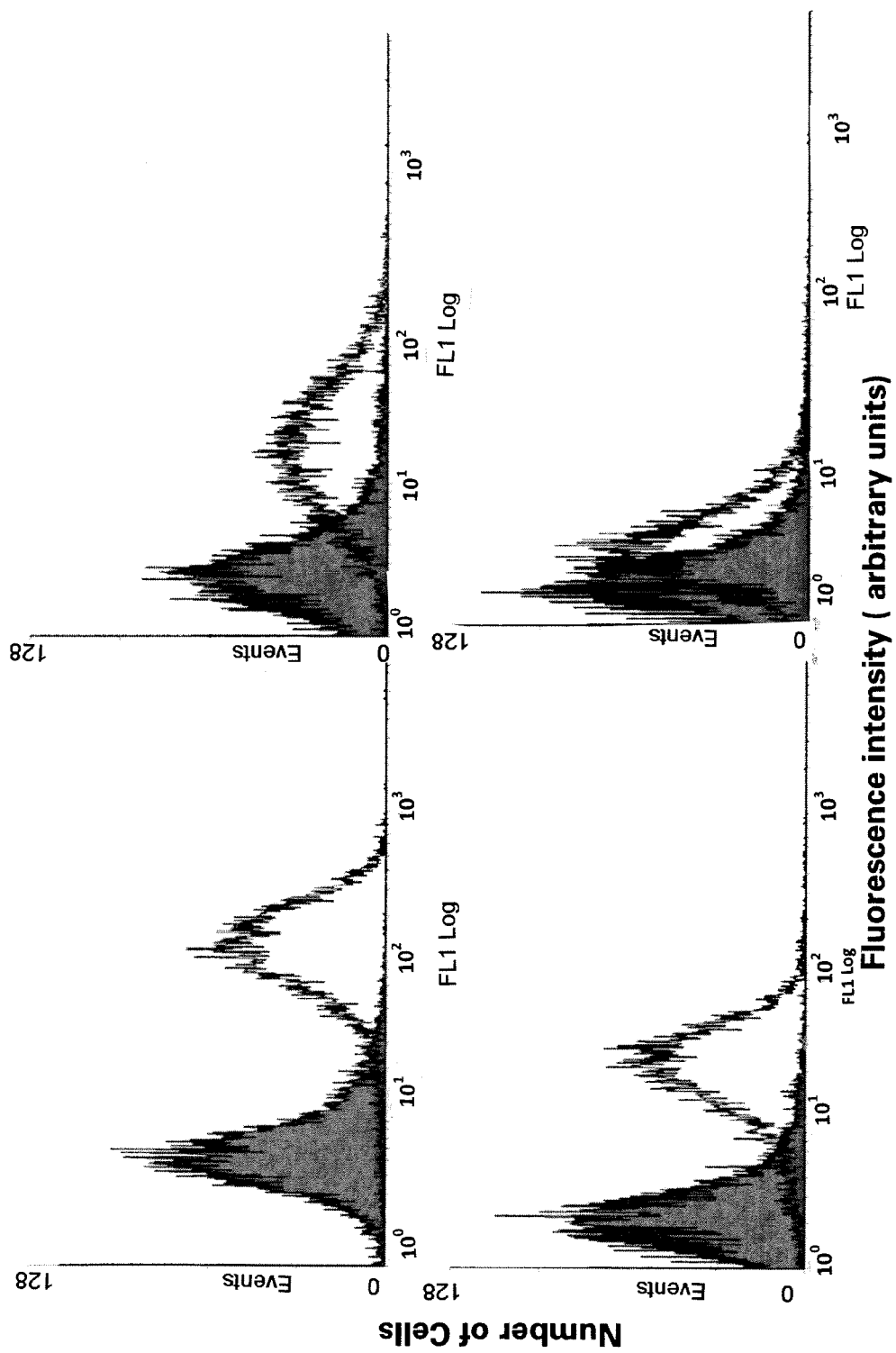
FIG. 3 shows qualitative flow cytometry results for anti-human PDGF-Rβ antibody against four cell types A172 (human brain glioblastoma, positive control), U87 (human brain glioblastoma), M231 (human breast adenocarcinoma) and HT29 (human colorectal adenocarcinoma, negative control).

Flow cytometry was used to evaluate the cells for their PDGF-Rβ expression in vitro (Table 5). One cell line, LS174T, was not analyzed due to extensive clumping, which interfered with the analysis. FIG. 3 shows representative results for the two highest expressing cell lines, along with positive and negative controls. The results in FIG. 3 were reproducible (n=3).

TABLE 5

| Cell line | Qualitative FCM result |
|---|---|
| 3T3 | + |
| C6 | + |
| LLC | + |
| K7M2 | − |
| A172 | − |
| U87 | ++ |
| M231 | +++ |
| HT29 | − |
| LS174T | − |

The highest expressing cell lines were U87 and M231, both of human origin. These two lines, along with a negative control line (HT29) were injected into 6-12 week old immunocompromised mice and allowed to grow tumors. Tumor growth curves and success rates were dependent on the number of cells inoculated. Optimal tumor growth was obtained for the HT29 and U87 cell lines with three to four million cells/mouse, for M231, optimal results were obtained with ten million.

In vivo studies were carried out with female CD-1 nude mice (Charles River Labs, Hopkinton, Mass.) with an age range between 8 and 15 weeks. Mice were housed in a ventilated rack with food and water ad libitum and a standard 12 hour day-night lighting cycle. For xenografts, animals were injected with 100 μl of cells in a 50/50 v/v mix of matrigel and PBS. Cells were implanted subcutaneously in the left hindquarter. Implantation was performed under isoflurane anesthesia. For HT29 and U87 $3\text{-}4 \times 10^6$ cells were implanted in each mouse. For M231, $1 \times 10^7$ cells were implanted in each mouse. Under these conditions, useable tumors (100 to 300 ug) were obtained in 3 to 4 weeks in greater than 80% of the injected animals.

ELISA

Tumors were collected from mice by dissection, and whole tumors were stored at −20° C. until processing. Tumors were ground on ice in 1 ml of RIPA buffer supplemented with a protease inhibitor cocktail (Santa Cruz Biotech, Santa Cruz, Calif. #24948) in a dounce homogenizer. Homogenates were then incubated on ice for 30 minutes, then centrifuged at 10,000×G for 10 minutes in a refrigerated centrifuge. Supernatants were collected and stored on ice or at 4° C. until further processing. Protein concentrations in lysates were determined using a BCA protein assay kit (Pierce Biotechnology 23225). Lysates were diluted to a standard concentration to yield 20 ug of protein/well in the microtiter plate. ELISA's were run with a commercially available human PDGF-Rβ kit (R&D Systems, DYC385) according to the manufacturer's instructions. Each sample was run in triplicate, and data are reported as pg PDGF-Rβ/ug total protein, errors are reported as standard deviations.

Figure 4:
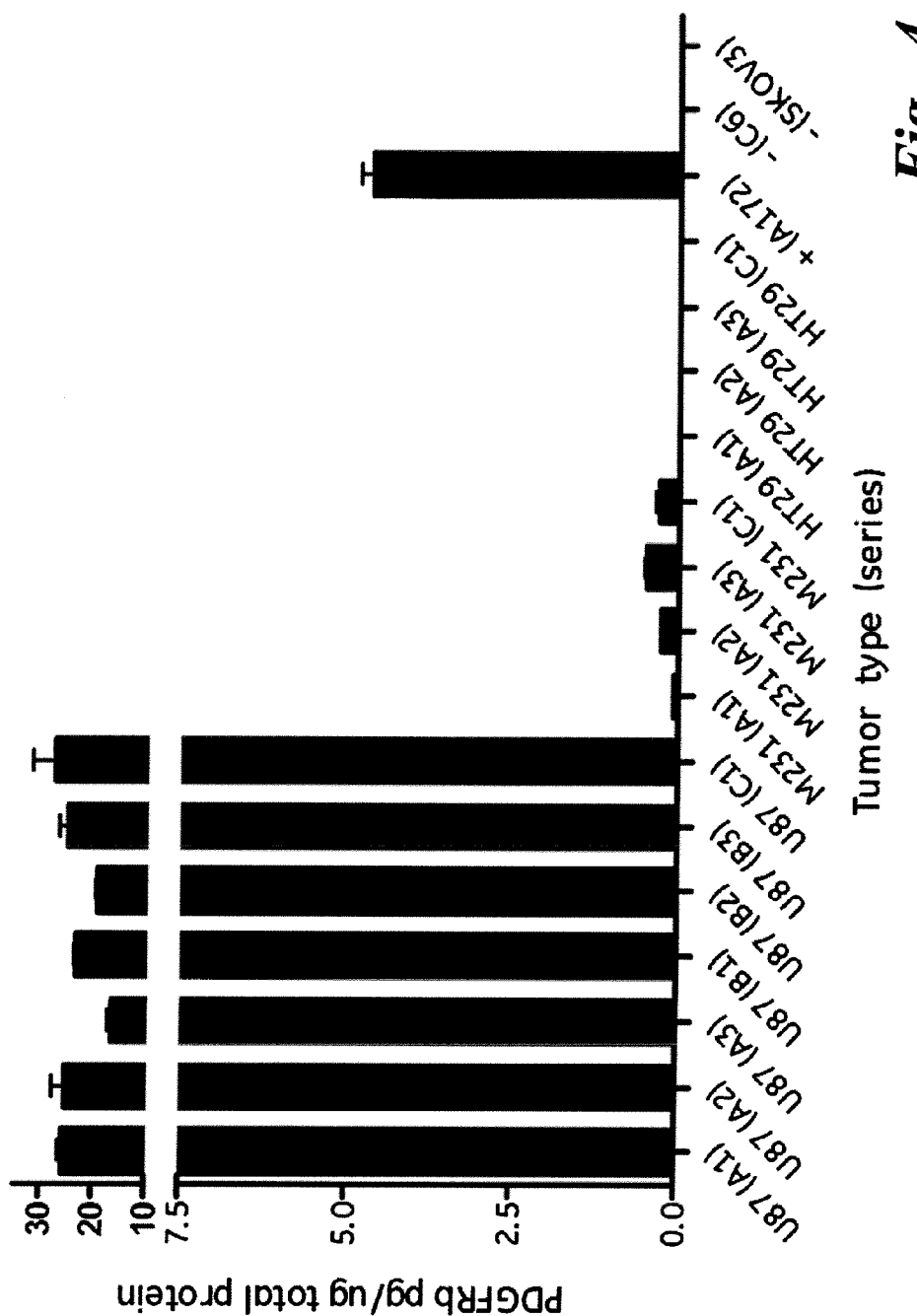
FIG. 4 shows the results of ELISA assays against a panel of tumor types.

Target expression in vivo was measured by ELISA. Excised tumors were homogenized and analyzed for PDGF-R β using a commercially available matched pair kit (R&D systems, Minneapolis, Minn.). The results, in FIG. 4, show that the U87 cell line grows a high-expressing tumor, M231 a low expressing tumor, and HT29 a tumor with no expression. The analysis was carried out on tumors from multiple sources (groups A and C), including at least three U87 tumors from an independent investigator at GRC (group B). ELISA controls were cell-culture lysates of the positive and negative control lines used for flow cytometry. These results indicate that tumor xenografts of U87, M231, and HT29 are appropriate for the in vivo study of molecules targeting human PDGF-R β.

Optical Imaging

A monoclonal antibody to human PDGF-R β (R&D Systems, Mab1263) or an isotype control (R&D Systems, Mab002) was labeled with Alexa-fluor 647 using an antibody labeling kit (Invitrogen, A20186). The antibody was subsequently purified away from the remaining dye. UV/Vis spectroscopy indicated 6 dyes/antibody on average.

Figure 5:
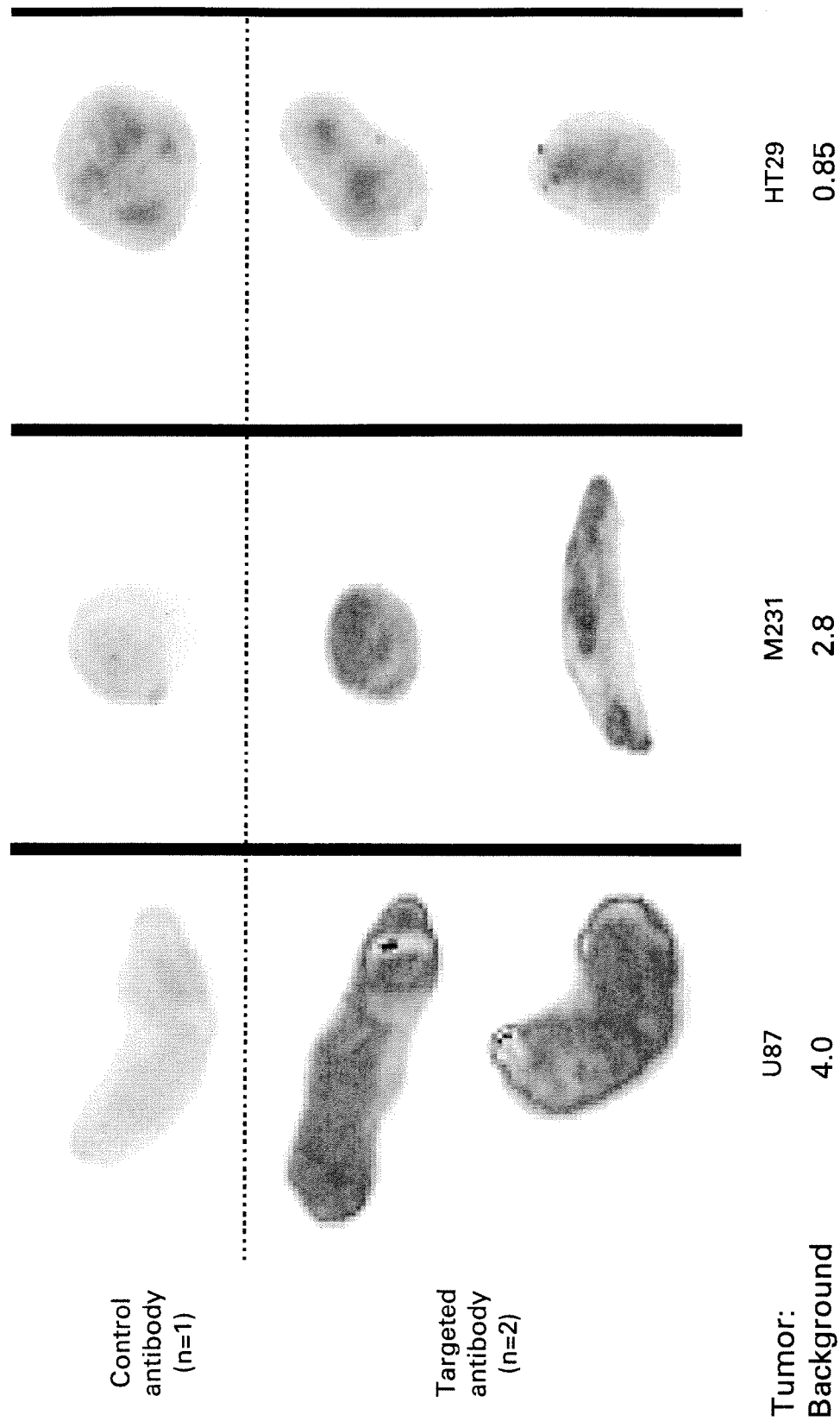
FIG. 5 shows an in vivo optical assay using anti-human PDGF-Rβ in U87 (high PDGF-Rβ expression), M231 (moderate/low PDGF-Rβ expression) and HT29 (no PDGF-Rβ expression) tumors.

Labeled antibodies were used to confirm target expression in vivo. Alexa647 functionalized antibodies (either an isotype control or an anti-human-PDGF-Rβ antibody) was injected into mice carrying U87, M231, or HT29 tumors. The tumors were excised 72 hours later, and imaged on a scanning fluorescence imager. The results show the highest antibody uptake in U87 tumors, followed by M231 tumors. No significant uptake was seen in HT29 tumors. Uptake was quantified by drawing a freeform ROI around each tumor and calculating the mean fluorescence intensity. The tumor:background fluorescence ratios are shown in FIG. 5.

The results show that the highest amount of target expression in the tumors is found in the U87 model, and a moderate amount is found in the M231 model. The HT29 model is used to evaluate background signal. These results confirm the results demonstrated with the ELISA kit. Based on these results, the U87 model was chosen for biodistribution studies of the PDGF-Rβ polypeptides. Polypeptides were also evaluated in the M231 model to assess their ability to target a lower expressing tissue.

His6-Polypeptide (SEQ ID NO: 26) Biodistribution Studies

All polypeptides were received from Affibody AB in Sweden. The polypeptides are referred to by their numeric internal development codes, which are prefixed with "Z". Table 1 details the polypeptides described herein. The polypeptides include one control polypeptide Ztaq (SEQ. ID NO. 10)), one low affinity monovalent anti-PDGF-Rβ polypeptide (Z1982; SEQ. ID NO. 14), a panel of three high affinity, monomeric anti-PDGF-Rβ polypeptides (Z2465; SEQ. ID NO. 16), Z2483 (SEQ. ID NO. 18), Z2516 (SEQ. ID NO. 17) and a dimer of one of the high affinity anti-PDGF-Rβ polypeptides, Z(2465)$_2$ (SEQ. ID NO. 19). All the His6-containing (SEQ ID NO: 26) sequences contain a C-terminal cysteine, of which the thiol group has been blocked using N-ethyl Maleimide (NEM).

Figure 1A:
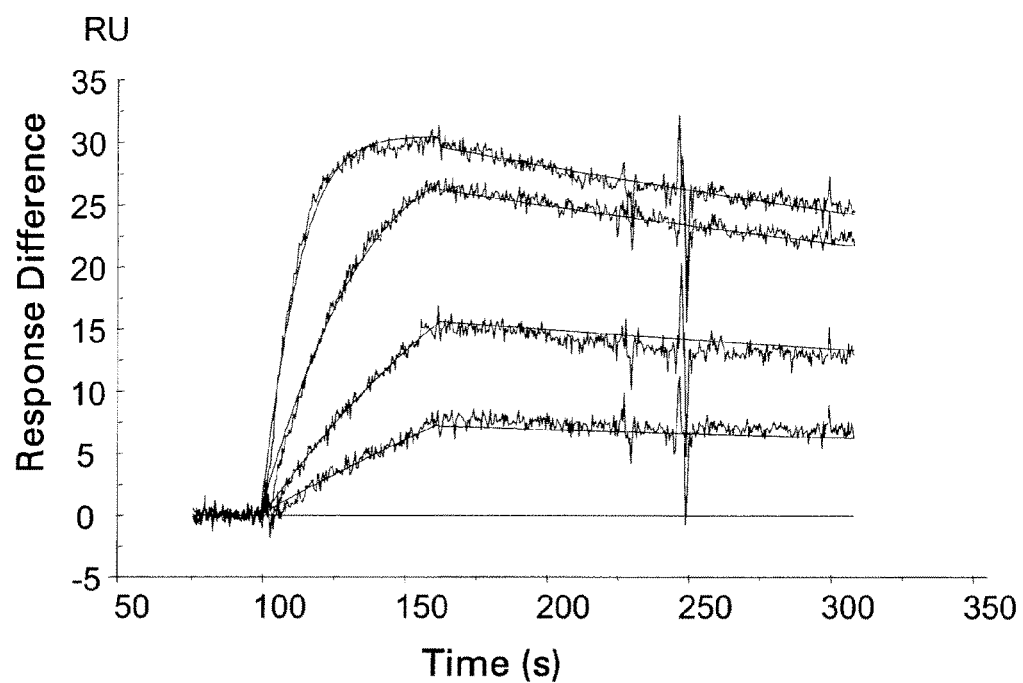
Figure 1B:
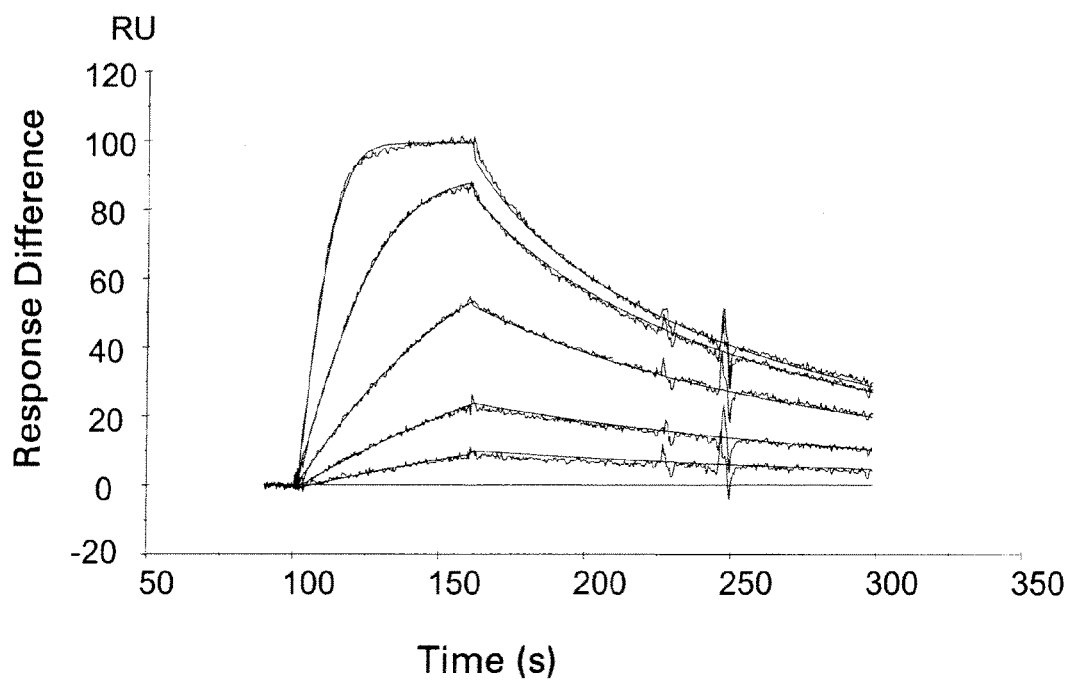
Figure 2:
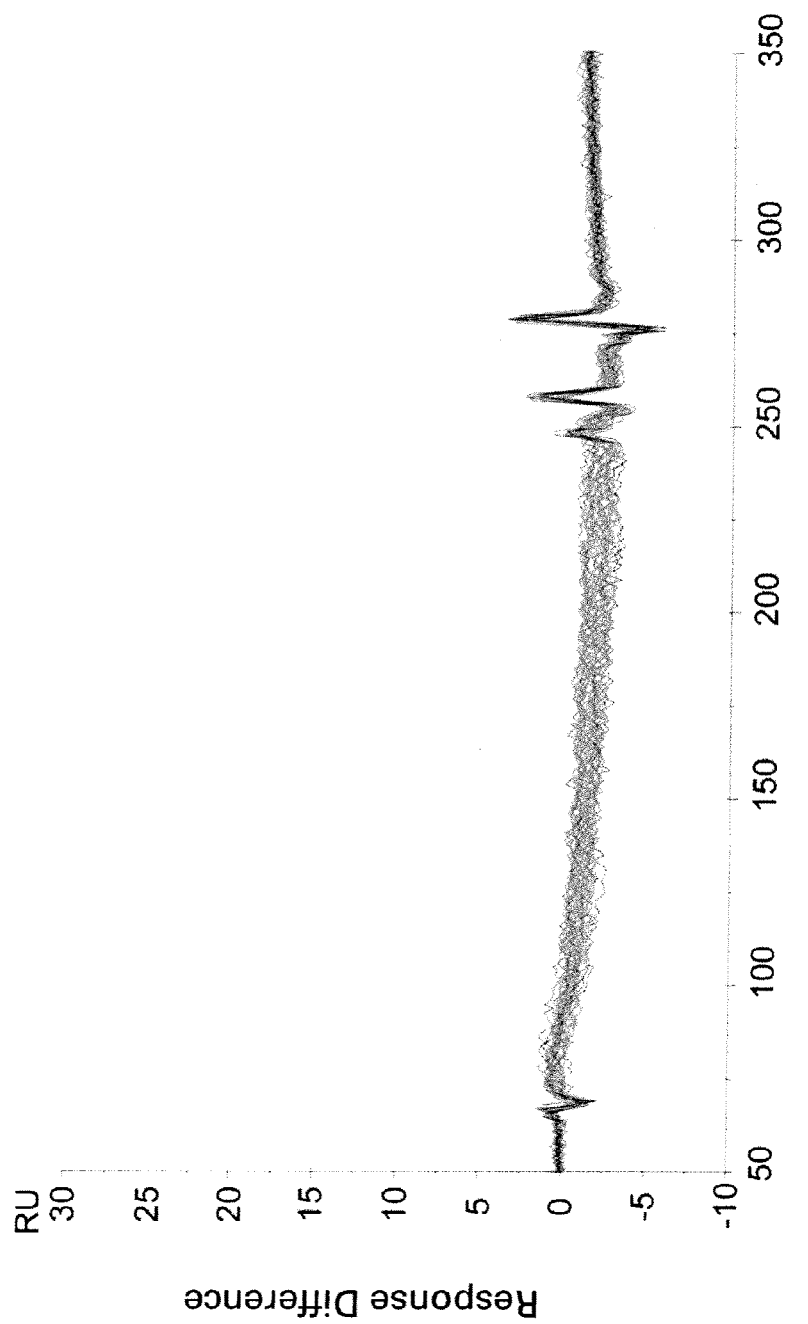
FIG. 2 shows the SPR of Z2465 (SEQ. ID NO. 16) against human PDGF-Rα(hPDGF-Rα).

FIG. 1 shows example surface plasmon resonance (SPR) data obtained for Z2465 (SEQ. ID NO. 16) when run on human (A) and murine (B) PDGF-Rβ-functionalized surfaces. All polypeptides were raised against human PDGF-Rβ, but affinity values for the murine target are relevant for preclinical studies in mouse models. The data in FIG. 1 indicate that for this particular polypeptide, the affinity for the murine target is poorer than for the human one. This relationship holds true for all polypeptides for which the affinities are known (Table 2), in which the values for the dimer Z(2465)$_2$ (SEQ. ID NO. 19) are estimates based on avidity affect. The polypeptides are also specific for PDGF-Rβ, over PDGF-Rα. FIG. 2 shows SPR data for the Z2465 (SEQ. ID NO. 16) polypeptide when run on a human PDGF-R Rβ-functionalized chip. These data demonstrate that while the polypeptide has high affinity for its intended target, it has none for the highly homologous PDGF-R Rβ.

Tc-99m Radiolabeling via the "6-his" tag (SEQ ID NO: 26) to produce $^{99m}$Tc(CO)$_3$(His6)-Polypeptide ('His6' disclosed as SEQ ID NO: 26)

Labeling of His6-tagged (SEQ ID NO: 26) Polypeptides with the fac-[$^{99}$mTc(CO)$_3$]$^+$ core was accomplished using modifications to a previously published procedure (Waibel, R.; et al., A. Nat. Biotechnol. 1999, 17, 897.). Briefly, Na[$^{99}$TcO$_4$] in saline (4 mCi, 2 mL) was added to an Isolink® boranocarbonate kit (Alberto, R. et al, J. Am. Chem. Soc. 2001, 123, 3135.). The resulting solution was heated to 95° C. for 15-20 minutes, to give fac-[$^{99m}$Tc(CO)$_3$(H$_2$O)$_3$]$^+$. A portion (2 mCi, 1 mL) of the solution was removed and neutralized to pH ~7 with 1 N HCl. A 325 µL aliquot was removed and added to a solution of the His6-Polypeptide (SEQ ID NO: 26) (100 µg). The resulting solution was heated in a water bath at 35-37° C. for 40 minutes. Typical radiochemical yields ranged from 80-95% (determined by ITLC-SG, Biodex, 0.9% NaCl). The crude reaction products were chromatographed on a NAP-5 column (GE Healthcare, 10 mM PBS) to give products of >99% radiochemical purity. Typical specific activities obtained were 3-4 µCi/µg. The resulting solution was then diluted with 10 mM PBS to give the proper concentration for subsequent biodistribution studies.

HPLC was carried out on an Agilent 1100 series HPLC equipped with a Grace-Vydac Peptide/Protein C4 (4.6×250 mm) column and a Raytest GABI radioactivity detector. Solvent A was 95:5 water:MeCN with 0.1% TFA, and solvent B was 5:95 water:MeCN with 0.1% TFA. The gradient was as follows (all changes linear; t/%/B): 0/0, 4/20, 16/60, 20/100, 25/100, 26/0, 31/0.

Each polypeptide was labeled with the tricarbonyltechnetium core in high yield (>90%) before purification. Purification by NAP-5 chromatography gave samples of Tc-99m-labeled Polypeptides in >99% radiochemical purity (Table 6).

TABLE 6

| Compound | Crude yield (%) | NAP-5 RCP (%) |
| --- | --- | --- |
| Z2465 (SEQ. ID NO. 16) | 92 | >99 |
| Z2483 (SEQ. ID NO. 18) | >95 | >99 |
| Z1982 (SEQ. ID NO. 14) | 94 | >99 |

Representative HPLC chromatograms of NAP-5 purified radiolabeled polypeptides are shown in FIG. 6. The retention time of each radiolabeled species was virtually unchanged from the corresponding unlabeled polypeptide's retention time in a 220 nm UV chromatogram (except for the time difference due to the physical separation of the UV and gamma detectors; data not shown). These labeled polypeptides were then used for biodistribution studies.

His and Cys Challenge Studies—$^{99}$Tc(CO)$_3$(His6)-Polypeptide ('His6' Disclosed as SEQ ID NO: 26)

$^{99m}$Tc(CO)$_3$(His6)-22465 ('His6' disclosed as SEQ ID NO: 26) (SEQ. ID NO. 16) was obtained by conjugating N-ethyl-maleimide (NEM) to (His6)-Z2465 ('His6' disclosed as SEQ ID NO: 26) (SEQ. ID NO. 16) and subsequently radiolabeled as described in section "Tc-99m Radiolabeling via the "6-his" tag." (SEQ ID NO: 26) Approximately 300 µCi of final purified product containing no greater than 50 µg (6.25×10-9 mol) of His6-Z2465 ('His6' disclosed as SEQ ID NO: 26) (SEQ. ID NO. 16) in 800 µL of 10 mM PBS was divided equally between two separate 1 dram vials. To the first vial was added 97 µL of L-His (6.25×10$^{-6}$ mol @ 10 mg/mL-1 in saline), the vial capped and placed on a pre-heated lead reaction block at 37° C. To the second 1 dram vial was added 151.4 µL of L-Cys (6.25×10-6 mol @ 5 mg.mL-1 in saline). This second vial was also capped and placed in the leaded reaction block. Both solutions were maintained at 37° C. overnight. At t=6 hrs and t=24 hrs, aliquots were removed and analyzed by SEC HPLC. The initial purity of $^{99m}$Tc(CO)$_3$(His6)-22465 ('His6' disclosed as SEQ ID NO: (SEQ. ID NO. 16) by ITLC was nearly quantitative (99.9%). Upon introduction of a 1000-fold molar excess of L-His challenge showed 95.7% of the product remained intact after 6 hours, and was unchanged at 96.6% after 24 hours. Introduction of a 1000-fold molar excess of L-Cys gave a product mixture containing 69.0% after 6 hours. This remained unchanged overnight with a final mixture containing 70.8% of $^{99m}$Tc(CO)$_3$(His6)-22465 ('His6' disclosed as SEQ ID NO: 26) (SEQ. ID NO. 16).

Biodistribution

Mice were given tail-vein injections of ~1 µg of Tc-99m-labeled polypeptides (~3 µCi/1 µg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The % injected dose for each organ was determined based on this total, and organs were weighed for determination of the % injected dose per gram, (% ID/g). Data is reported as mean value for all three mice in the timepoint with error bars representing the standard deviation of the group.

The Tc-99m labeled Z2465 (SEQ. ID NO. 16) and Ztaq (SEQ. ID NO. 10) polypeptides were injected into U87 mice, and the Z2465 (SEQ. ID NO. 16) polypeptide was injected into HT29 mice, although a more limited set of timepoints were collected. FIG. 7 shows the tumor and blood curves for these experiments. The Z2465 (SEQ. ID NO. 16) polypeptide shows strong tumor uptake in target-expressing U87 tumors, with a maximal value of more than 7% of the injected dose per gram of tissue at 30 minutes post-injection (PI), and a peak tumor:blood ratio of more than 25 at 120 minutes PI. As controls, the Z2465 (SEQ. ID NO. 16) polypeptide was injected into mice carrying non-target-expressing HT29 tumors, and the non-targeted Ztaq (SEQ. ID NO. 10) polypeptide was injected into mice carrying target-expressing U87 tumors. Both control experiments have nominal tumor uptake values of 0% to 1%, and tumor:blood ratios of <5. These results, also shown in FIG. 7, indicate that the Z2465 (SEQ. ID NO. 16) polypeptide is specifically targeting the PDGF-R-β-expressed in the U87 tumors.

Polypeptides exhibit a monoexponential clearance from the blood with half-lives of less than two minutes. This clearance is primarily mediated by the kidneys. Activity is eventually secreted in the urine. Polypeptide uptake in the spleen was minimal, and variable uptake in the liver is observed. These results indicate that the polypeptides are effectively cleared via a renal route.

Downselection

The Z2465 (SEQ. ID NO. 16) polypeptide exhibited maximum tumor:blood ratios at 120 minutes PI, so this timepoint was chosen for comparison studies. Single point biodistributions were carried out with all four monomeric polypeptides and tumor:blood and absolute tumor uptake ratios were compared (FIG. 9). The Z2483 (SEQ. ID NO. 18) polypeptide had the highest absolute tumor uptake, while the Z2465 (SEQ. ID NO. 16) polypeptide had the highest tumor:blood ratio due to a slightly lower blood value. These results clearly indicate that the Z2465 (SEQ. ID NO. 16) is the best-performing of the monomeric polypeptides.

Valency

Bivalent polypeptides exhibit higher affinity than the corresponding monomers, presumably due to the avidity effect. Their larger size, however, may hinder tumor penetration. For the PDGF-Rβ polypeptides, bivalent forms of each the four high affinity polypeptides were available. The Z2465 (SEQ. ID NO. 16) dimer, (Z2465)$_2$ (SEQ. ID NO. 19), was radiolabeled and used for a four-hour biodistribution experiment in U87-tumored mice. The results (FIG. 10) show that the bivalent polypeptide does not have tumor uptake as high as that observed for the corresponding monomer, but that it does not exhibit any washout. This is likely due to a decreased off rate. By four hours PI, the mono- and bivalent polypeptides have comparable tumor:blood ratios.

The monovalent and bivalent polypeptides otherwise exhibit similar biodistribution characteristics, and blood half-lives are observed for both in the one to two minute range. The results clearly indicate that both monomeric and divalent polypeptides can be targeted to PDGF-Rβ in vivo.

Low-Expressing Model

To evaluate the ability of the polypeptide to detect its target at lower copy number, the Z2465 (SEQ. ID NO. 16) polypeptide was used for biodistribution experiments with M231-tumored mice. The M231 tumors exhibit lower levels of PDGF-RB-beta expression, as described above. The results (FIG. 11) show that the Z2465 (SEQ. ID NO. 16) polypeptide still exhibits uptake and tumor:blood ratios above background levels, but that they are reduced compared to those observed in the high-expressing model. This clearly demonstrates that PDGF-RB-beta targeted polypeptides can be used to detect even low levels of target in vivo.

When the bivalent polypeptide, (Z(2465)$_2$ (SEQ. ID NO. 19) was used in M231-tumored mice, no effect was observed on uptake or tumor:blood ratios. The values were unchanged from the high-expressing model (FIG. 12). These data indicate that the uptake observed with the monovalent polypeptide is target concentration limited, but that some other process, possibly tumor penetration, limits the uptake observed for the bivalent polypeptide. Again, these results indicate that both monovalent and divalent polypeptides can be used for targeting applications, and that the choice depends on the specific nature of the application. For example, the divalent polypeptide might be chosen for an application where a lower level of target expression is expected.

Low Affinity Polypeptide

The Z1982 (SEQ ID NO. 14) polypeptide, which has an affinity of only 4 nM, was used for a single point biodistribution in tumored mice. The results (FIG. 13) show increased uptake in the high-expressing model with respect to the lower- or non-expressing model. The tumor:blood ratios are higher than those observed in control tumors or those observed with the Ztaq (SEQ. ID NO. 10) control, although in the case of Ztaq (SEQ. ID NO. 10), this difference is driven by high (~1%) blood values.

Polypeptides, Tc-99m-Labeled via cPn216

Z02465 (SEQ. ID NO. 23) and Z03358 (SEQ. ID NO. 24) were functionalized with an engineered C-terminal cysteine residue for site-specific labeling and without a His6-tag (SEQ ID NO: 26). Polypeptide affinities were determined for Z2465 (SEQ. ID NO. 16), by Affibody AB using BIAcore (GEHC) and shown to have a Kd of 600 pM. As the polypeptides were raised against human PDGF-RBβ, the affinity for the murine target is lower, with a Kd value of about 4 nM. The compounds provided are also highly specific as demonstrated both in vitro and in vivo.

The epitope for the all listed polypeptides is shared with the receptor's natural ligand PDGF-β. Z2465 (SEQ. ID NO. 16) is able to completely compete off PDGF-BB in a BIAcore competition experiment.

Z2465 (SEQ. ID NO. 16) demonstrated favorable biodistribution characteristics, specifically high target uptake coupled with minimal liver non-specific retention. Z03358 (SEQ. ID NO. 24) is a derivative of Z2465 and Z02465 (SEQ. ID NO. 16 and SEQ. ID 23, respectively). The purity of the polypeptide molecules were determined to be >95% by High Performance Liquid Chromatography (HPLC).

TABLE 7

| Polypeptide | Chelators |
| --- | --- |
| Z02465 (SEQ. ID NO. 23) | cPn216 |
|  | PEG$_4$-cPn216 |
| Z03358 (SEQ. ID NO. 24) | cPn216 |

Mal-cPn216

To introduce the Tc-99m chelator cPn216 (FIG. 14), a bifunctional compound Mal-cPn216 was synthesized consisting of a thiol-reactive maleimide group for conjugation to a terminal cysteine of a polypeptide and an amine oxime group for chelating Tc-99m.

cPn216-amine was obtained from GE Healthcare. N-β-maleimidopropionic acid was purchased from Pierce Technologies (Rockford, Ill.). N-methylmorpholine, (benzotriazol-1-yloxy)tripyrrolidinophosphonium hexafluorophosphate (PyBoP), dithiothreitol (DTT), ammonium bicarbonate, and anhydrous DMF were purchased from Aldrich (Milwaukee, Wis.). PBS buffer (1x, pH 7.4) was obtained from Invitrogen (Carlsbad, Calif.). HPLC-grade acetonitrile ($CH_3CN$), HPLC-grade trifluoroacetic acid (TFA), and Millipore 18 mΩ water were used for HPLC purifications.

To a ice-cooled solution of N-β-maleimidopropionic acid (108 mg, 0.64 mmol), cPn216-amine (200 mg, 0.58 mmol), and PyBoP (333 mg, 0.64 mmol) in anhydrous DMF at 0° C. was added 0.4 M of N-methylmorpholine in DMF (128 μL, 1.16 mmol). The ice bath was removed after 2 hrs, and the mixture was stirred at room temperature overnight before being subjected to HPLC purification. The product was obtained as a white powder (230 mg, 80% yield). $^1$H-NMR (400 MHz, DMSO-d$_6$): δ 1.35 (m, 2H), 1.43 (s, 12H), 1.56 (m, 5H), 1.85 (s, 6H), 2.33 (dd, J1=8 Hz, J2=4 Hz, 2H), 2.78 (m, 4H), 3.04 (m, 2H), 3.61 (dd, J1=8 Hz, J2=4 Hz, 2H), 7.02 (s, 2H), 8.02 (s, 1H), 8.68 (s, 4H), 11.26 (s, 2H); m/z=495.2 for [M+H]+($C_{24}H_{43}N_6O_5$, Calculated MW=495.3).

Mal-PEG$_4$-cPn216

To evaluate the effect of PEGylated linker on the performance of the polypeptide molecules a bifunctional compound Mal-PEG$_4$-cPn216 (FIG. 15) was synthesized consisting of a thiol-reactive maleimide group for conjugation to the terminal cysteine and an amine oxime group for chelating Tc-99m. The maleimide group and the amine oxime group was connected by a PEG$_4$ linker.

cPn216-amine was obtained from GE Healthcare. NHS-PEG$_4$-maleimide was purchased from Pierce Technologies (Rockford, Ill.). HPLC grade acetonitrile ($CH_3CN$), trifluoroacetic acid (TFA), and Millipore 18 mΩ water were used for HPLC purifications.

A mixture of cPn216-amine (5 mg, 0.0145 mmol) and NHS-PEG$_4$-maleimide (9 mg, 0.0174 mmol) in anhydrous DMSO (0.5 mL) was stirred at room temperature for 18 h. Resulting mixture was purified by HPLC (0 to 30% CH3CN in water) to obtain 5.1 mg of the title compound as a white solid (46%). $^1$H-NMR (400 MHz, MeOH-d$_4$): δ 1.55 (m, 15H), 1.65-1.78 (m, 6H), 1.94 (s, 6H), 2.48 (q, J=7.23 Hz, 4H), 3.03 (t, J=8.25 Hz, 4H), 3.52 (t, J=5.05 Hz, 2H), 3.60-3.66 (m, 14H), 3.75 (t, J=8.00 Hz, 2H), 3.79 (t, J=8.00 Hz, 2H), 6.84 (s, 2H); High resolution MS m/z calcd for $C_{35}H_{64}N_7O_{10}$ [M+H]+742.4715, found 742.4853.

Bioconjugation of Mal-cPn216 and Mal-PEG$_4$-cPn216 to Polypeptide Molecules

The polypeptide was dissolved with freshly degassed PBS buffer (1x, pH 7.4) at a concentration of approximately 1 mg/mL. The disulfide linkage in the polypeptide was reduced by the addition of DTT solution in freshly degassed PBS buffer (1x, pH 7.4). The final concentration of DTT was 20 mM. The reaction mixture was vortexed for 2 hours and passed through a Zeba desalt spin column (Pierce Technologies) pre-equilibrated with degassed PBS buffer (1x, pH 7.4) to remove excess of DTT reagent. The eluted reduced polypeptide molecule was collected, and the bifunctional compound mal-cPn216 or Mal-PEG$_4$-cPn216 was added (20 equivalents per equivalent of the polypeptide) as a solution in DMSO, and the mixture was vortexed at room temperature. The reaction was allowed to proceed overnight to ensure the complete conversion of the Polypeptide molecules. For some polypeptide molecules, for example, Z02465 (SEQ. ID NO. 23), reaction monitoring with liquid chromatography followed by electrospray ionization time of flight mass spectrometer (LC-MS) suggested that the reaction with mal-cPn216 could be shortened to 2 hours.

Initial purification of the target product with either dialysis or desalt spin column was not sufficient in removing the excess of mal-cPn216. Also the recovery of the target product was low (~20%). Reverse phase HPLC was then chosen as the purification method based on the highly stable nature of polypeptide molecules.

The HPLC purification was performed on a MiCHROM Magic C18AQ 5μ 200 A column (MiChrom Bioresources, Auburn, Calif.). Solvent A: H2O (with 0.1% formic acid), Solvent B: $CH_3CN$ (with 0.1% formic acid). Gradient: 5-100% B over 30 mins.

The fractions containing desired product were combined and neutralized with 100 mM ammonium bicarbonate solution, and the solvents were removed by lyophilization to give the conjugated polypeptide as a white solid. A significant improvement in purity (>95% as determined by HPLC shown in FIG. 16) and yield (66-93%) was achieved.

LC-MS analysis of the purified product confirmed the presence of the desired product, and the MW suggested that only one cPn216 or PEG4-cPn216 label was added to polypeptide constructs including Z02465 (SEQ. ID NO. 23) and Z03358

(SEQ. ID NO. 24). (calculated MW: 7732 Da, 7979 Da, and 7011 Da, found: 7732 Da, 7979 Da, and 7011 Da for Z02465 (SEQ. ID NO. 23)-cPn216, Z02465 (SEQ. ID NO. 23)—PEG$_4$-cPn216, and Z03358 (SEQ. ID NO. 24)-cPn216, respectively).

Tc-99m Labeling via cPn216: Low Volume Chelakit Assembly

To a 20 mL vial was added 10.00 mL of distilled, deionized water. Nitrogen gas was bubbled through this solution for approximately 30 minutes prior to addition of the NaHCO$_3$ (450 mg, 5.36×10$^{-3}$ mol), Na$_2$CO$_3$ (60 mg, 5.66×10$^{-4}$ mol) and sodium para-aminobenzoate (20 mg, 1.26×10$^{-4}$ mol). FIG. 17 shows the results to explore the concentration requirements for effective labeling. All reagents were weighed independently and added to the vial containing water. Tin chloride (1.6 mg, 7.09×10$^{-6}$ mol) and MDP (2.5 mg, 1.42×10$^{-5}$ mol) were weighed together into a 1 dram vial and subsequently transferred (with 1 subsequent wash) by rapid suspension in approximately 1 mL of the carbonate buffer mixture. 10 µL aliquots were removed and transferred under a stream of nitrogen to silanized vials, immediately frozen and maintained in a liquid nitrogen bath until lyophilization. Each vial was partially capped with rubber septa and placed in a tray lyophilizer overnight. Vials were sealed under vacuum, removed from the lyophilizer, crimp-sealed with aluminum caps, re-pressurized with anhydrous nitrogen and stored in a freezer until future use.

Tc-99m labeling of Polypeptide-Cys-mal-cPn216

Synthesis of the radiolabeled polypeptide was performed using a one-step kit formulation produced in house (Chelakit A+) containing a lyophilized mixture of stannous chloride as a reducing agent for technetium, methylene diphosphonic acid, p-aminobenzoate as a free-radical scavenger and sodium bicarbonate/sodium carbonate (pH 9.2) as buffer. In rapid succession, 20 µL of a 2 µg/µL solution of polypeptide in saline was added to the Chelakit, followed immediately by Na99 mTcO4 (0.8 mCi, 29.6 MBq) in 0.080 mL of saline (0.15M NaCl) obtained from Cardinal Health (Albany, N.Y.). The mixture was agitated once and allowed to sit at ambient temperature for 20 min. Upon completion, the crude radiochemical yield was determined by ITLC (Table 8 below according to ITLC-SG, Biodex, 0.9% NaCl).

TABLE 8

| Compound | Crude RCP (%) | purified RCP (%) | RYC (%) decay corrected/ (uncorrected) | n |
|---|---|---|---|---|
| Z02465 (SEQ. ID NO. 23) | 93.6 (4.8) | 95.3 (3.4) | 53.9 (13.1) | 5 |
| Z02465PEG (SEQ. ID NO. 23) | 98.2 | 89.6 | 65.9 | 1 |
| Z2483 (SEQ. ID NO. 18) | 68.7 | 83.7 | 11.3 | 1 |
| Z03358 (SEQ. ID NO. 24) | 96.4 (0.2) | 96.1 (3.7) | 62.8 (5.3) | 2 |

The reaction volume was increased to 0.45 mL with 0.35 mL of 150 mM sterile NaCl, and the final product purified by size exclusion chromatography (NAP5, GE Healthcare, charged with 10 mM PBS). The crude reaction mixture was loaded onto the NAP5 column, allowed to enter the gel bed and the final purified product isolated after elution with 0.8 mL of 10 mM PBS. Final activity was assayed in a standard dose calibrator (CRC-15R, Capintec, Ramsey, N.J.). Radiochemical yield (Table 8) and purity were determined by ITLC (>98.5%), C4 RP-HPLC and SEC-HPLC analysis. FIG. 18 shows the monomeric and chemically predictable behavior of the labeled Polypeptide-cPn construct Z02465 (SEQ. ID NO. 23) relative to the His6-construct Z2465 (SEQ. ID NO. 16) ('His6' disclosed as SEQ ID NO: 26). The final product (10-15 µCi/µg, 0.2-0.5 µCi/µL (0.37 MBq/µg, 7.4 MBq/mL)) was used immediately for biodistribution studies.

The corresponding Z02465 (SEQ. ID NO. 23)-Cys-cPn216, Z02465 (SEQ. ID NO. 23)-Cys-PEG$_4$-cPn216 and Z03358-(SEQ. ID NO. 24) Cys-cPn216 derivatives were labeled using a standard one-step kit-based procedure (Chelakit A+—assembled in house). Previous work established that a cPn-containing vector labels best when the vector concentration is at or above 1×10$^{-5}$ M when working at ambient temperature. To achieve this concentration with a reasonable amount of Z02465 (SEQ. ID NO. 23)-Cys-cPn216 (MW=7733 g·mol$^{-1}$) and Z03358 (SEQ. ID NO. 24)-Cys-cPn216 (MW=7011 g·mol$^{-1}$) the reaction volume was kept below about 100 µL to 120 µL; requiring the use of 20-40 µg of material. Chelakits were altered to include a reduced amount of SnCl2, methylene diphosphonic acid, p-aminobenzoate, potassium carbonate and potassium bicarbonate to accommodate the lower volume. Z02465 (SEQ. ID NO. 23)-Cys-cPn216 and Z03358(SEQ. ID NO. 24)-Cys-cPn216 were labeled in respectable radiochemical yield (Table 8) by combining 0.5-1.2 mCi (18.5-44.4 MBq) of Na99 mTcO4 at 10-25 mCi/mL with 20 µL of a 2 µg/µL solution of the polypeptide in a low volume Chelakit for 20 min. at ambient temperature. RP-HPLC analysis of these derivatives were a challenge when performed at basic pH using 0.06% ammonia in water as the mobile phase (vide infra). NAP5 purification resulted in a final product with high radiochemical purity and an isolated radiochemical yield between 54 and 67%.

The HPLC conditions used for this experiment were as follows: C4 RP-HPLC method 1: Solvent A: 95/5H$_2$O/CH$_3$CN (with 0.05% TFA), Solvent B: 95/5 CH$_3$CN/H$_2$O with 0.05% TFA. Gradient elution: 0 min. 0% B, 4 min. 20% B, 16 min. 60% B, 20 min. 100% B, 25 min. 100% B, 26 min. 0% B, 31 min. 0% B.

C4 RP-HPLC method 2: Solvent A: 0.06% NH3 in water, Solvent B: CH$_3$CN. Gradient elution: 0 min. 0% B, 4 min. 20% B, 16 min. 60% B, 20 min. 100% B, 25 min. 100% B, 26 min. 0% B, 31 min. 0% B.

RP-HPLC analysis performed on an HP Agilent 1100 with a G1311A QuatPump, G1313A autoinjector with 100 µL syringe and 2.0 mL seat capillary, Grace Vydac—protein C4 column (S/N E050929-2-1, 4.6 mm×150 mm), G1316A column heater, G1315A DAD and Ramon Star—GABI gamma-detector.

SEC HPLC: Solvent: 1× (10 mM) PBS (Gibco, Invitrogen, pH 7.4 containing CaCl$_2$ and MgCl$_2$). Isocratic elution for 30 min. Analysis performed on a: Perkin Elmer SEC-4 Solvent Environmental control, Series 410 LC pump, ISS 200 Advanced LC sample processor and Series 200 Diode Array Detector. A Raytest GABI with Socket 8103 0111 pinhole (0.7 mm inner diameter with 250 µL volume) flow cell gamma detector was interfaced through a Perkin Elmer NCI 900 Network Chromatography Interface. The column used was a Superdex 75 10/300 GL High Performance SEC column (GE Healthcare. code: 17-5174-01, ID no. 0639059).

Lack of Non-Specific Tc-99m Labeling of Polypeptide-Cys-mal-cPn216

In order to establish that the Tc-99m metal does not coordinate to alternative sites on the polypeptide construct, an attempt to incorporate Tc-99m onto the polypeptide backbone was performed using a one-step kit formulation Chelakit A+ containing a lyophilized mixture of stannous chloride as a reducing agent for technetium, methylene diphosphonic acid, p-aminobenzoate as a free-radical scavenger and sodium bicarbonate/sodium carbonate (pH 9.2) as buffer. In rapid succession, 50 μL of a 0.69 μg·μL$^{-1}$ solution of Z02465 (SEQ. ID NO. 23)-Cys-NEM in saline was added to the Chelakit, followed immediately by Na[$^{99m}$TcO$_4$] (0.5 mCi, 18.5 MBq) in 0.050 mL of saline (0.15M NaCl) obtained from Cardinal Health (Albany, N.Y.). The mixture was agitated once and allowed to sit at ambient temperature for 20 min. After 20 minutes, an aliquot of the crude reaction mixture was removed and analyzed by SEC HPLC His and Cys Challenge Studies—Z02465 (SEQ. ID NO. 23)-Cys-cPn216-$^{99m}$Tc(O)$_2$ In vitro stability of the Polypeptide-cPn-$^{99m}$Tc(O)$_2$ constructs were determined via cysteine and histidine challenge. To ensure an adequate excess of challenge agent, A 1000-fold excess relative to the total amount of polypeptide present (labeled and unlabeled) of either amino acid was added to a 10 mM PBS solution and incubated at 37° C. overnight (L-His and L-Cys mole amounts). Briefly, Z02465 (SEQ. ID NO. 23)-Cys-cPn-$^{99m}$Tc(O)$_2$ was obtained as described above [section Tc-99m labeling of Polypeptide-Cys-mal-cPn216]. Approximately 300 μCi of final purified product containing no greater than 40 μg (5.17×10$^{-9}$ mol) of Z02465 (SEQ. ID NO. 23)-Cys-cPn216 in 800 μL of 10 mM PBS was divided equally between two separate 1 dram vials. To the first vial was added 97 μL of L-His (6.25×10$^{-6}$ mol@ 10 mg/mL in saline), the vial capped and placed on a pre-heated lead reaction block at 37° C. To the second 1 dram vial was added 151.4 μL of L-Cys (6.25×10$^{-6}$ mol@ 5 mg/mL in saline). This second vial was also capped and placed in the leaded reaction block. Both solutions were maintained at 37° C. overnight. At t=7 hrs and t=24 hrs, aliquots were removed and analyzed by ITLC. At t=7 hrs, Z02465 (SEQ. ID NO. 23)-cPn-$^{99m}$Tc(O)$_2$ showed 31.5% degradation with L-His and 69% degradation with L-Cys while after 24 hrs 74.1 and 93.6% degradation was observed respectively.

Variable pH Analysis of Polypeptide Constructs cPn216-$^{99m}$Tc(O)$_2$ constructs are generally analyzed by reverse phase HPLC at pH 9 using a 0.06% ammonia in water solution as the aqueous mobile phase. This is due to the inherent instability and rapid degradation of the cPn216-$^{99m}$Tc(O)$_2$ complex under acidic conditions (i.e. 0.05% trifluoroacetic acid in water) that are widely used for the analysis of biological constructs by HPLC. $^{99m}$Tc(CO)$_3$(His6)-polypeptide ('His6' disclosed as SEQ ID NO:) constructs are more robust and can be analyzed using 0.05% TFA in water as the aqueous mobile phase. Using a series of $^{99m}$Tc(CO)$_3$(His6)-labeled ('His6' disclosed as SEQ ID NO: 26) polypeptide constructs, namely variant Z2465 the chemically robust His6-derivatives (SEQ ID NO: 26) were analyzed using three different aqueous mobile phases, 1) 0.05% TFA in water (pH<2), 2) 50 mM ammonium acetate (pH ~7) and 3) 0.06% ammonia in water (pH ~9). The results demonstrated aberrant HPLC behavior of an polypeptide at basic pH, indicating that analyses should be performed at pH 7 or lower. These results caused us to analyze our polypeptide-cPn216-$^{99m}$Tc(O)$_2$ constructs at pH 7 instead of the usual pH 9 conditions.

Animal Models Used to Study 99mTc-Polypeptide-cPn216 Conjugates

In vivo studies were carried out with female CD-1 nude mice (Charles River Labs, Hopkinton, Mass.) with an age range between 8 and 15 weeks. Mice were housed in a ventilated rack with food and water ad libitum and a standard 12 hour day-night lighting cycle. For xenografts, animals were injected with 100 ul of cells in a 50/50 v/v mix of matrigel and PBS. Cells were implanted subcutaneously in the left hindquarter. Implantation was performed under isoflurane anesthesia. For HT29 and U87, 3-4×10$^6$ cells were implanted in each mouse. For M231, 1×10$^7$ cells were implanted in each mouse. Under these conditions, useable tumors (100 to 300 ug) were obtained in 3 to 4 weeks in greater than 80% of animals injected.

Biodistribution of Tc-99m-Polypeptide-cPn216 Conjugates

Mice were given tail-vein injections of ~1 μg of Tc-99m-labeled polypeptides (~3 μCi/1 μg). Mice were placed in filter-paper lined cages until euthanasia. Three mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The % injected dose for each organ was determined based on this total, and organs were weighed for determination of the % injected dose per gram, (% ID/g). Data is reported as mean value for all three mice in the timepoint with error bars representing the standard deviation of the group. Four timepoints were taken over four hours (5, 30, 120, and 240 minutes post-injection).

The Z02465 (SEQ. ID NO. 23)-cPn216-Tc-99m polypeptide shows strong tumor uptake in target-expressing U87 tumors, with a value of 7.15±3.39% (n=6) of the injected dose per gram of tissue at 30 minutes post-injection (PI), which remains fairly constant over the time-course of the study up to 240 min PI. Tumor:blood ratios were 5, 12, and 15 at 30, 120, and 240 min post injection, respectively. The decreasing blood values predominantly drives the tumor:blood ratios over time. FIG. 19 shows the tumor, blood and tumor:blood curves for these experiments.

As controls, the polypeptide was injected into mice carrying non-target-expressing HT29 tumors, and the biodistribution study in section "His6-Polypeptide Biodistribution Studies" ('His6' disclosed as SEQ ID NO: 26) had examined non-targeted Ztaq (SEQ. ID NO. 10) polypeptide in mice carrying target-expressing U87 tumors. In the control HT29 model, no significant uptake was observed—tumor:blood ratios were between 1 to 2 over the course of the study, with absolute tumor uptake of ca. 1% ID/g over the course of the study. The blood curve between HT29 and U87 lines were nearly identical ruling out the differences in vasularity contributing to the observed tumor uptakes. In the case of the non-targeted Ztaq (SEQ. ID NO. 10) polypeptide injected into mice carrying target-expressing U87 tumors, similar behavior was observed. Both controls suggest a very high degree of specificity of Z02465 (SEQ. ID NO. 23)-cPn216-99 mTc for PDGF-Rβ in the xenograft models.

The Polypeptides exhibit a monoexponential clearance from the blood with half-lives of less than two minutes. This clearance is primarily mediated by the kidneys, with 39.30±7.30 (n=10) ID/organ at 240 min post-injection PI. Activity is secreted primarily in the urine. Polypeptide uptake in the spleen was minimal, and low uptake in the liver is observed, ca. 1.5% ID/organ (equivalent in value in mice to % ID/g) over the course of the study past one-half hour post injection.

Biodistribution Results for Z03358(SEQ. ID NO. 24)-cPn216-Tc-99m

No significant difference was observed between the biodistributions of (SEQ. ID NO. 24)-cPn216-Tc-99m and Z02465 (SEQ. ID NO. 23)-cPn216-Tc-99m. FIG. 21 shows the critical organ uptakes over the course of the study.

Biodistribution Results for Z02465 (SEQ. ID NO. 23)—PEG-cPn216-Tc-99m

No significant difference was observed between the tumor uptake of Z02465 (SEQ. ID NO. 23)-cPn216-Tc-99m and Z02465 (SEQ. ID NO. 23)—PEG4-cPn216-Tc-99m, though higher blood and liver retention were observed for the PEGylated version. FIG. 22 shows the critical organ uptakes over the course of the study.

TABLE 9

% ID/g Z02465 (SEQ. ID NO. 23) cPn216 in U87 Tumor Bearing Mice

|  | 5 Minutes | 30 Minutes | 120 Minutes | 240 Minutes |
| --- | --- | --- | --- | --- |
| Blood | 4.75 ± 0.17 (n = 6) | 1.43 ± 0.268 (n = 6) | 0.47 ± 0.07 (n = 10) | 0.32 ± 0.06 (n = 10) |
| Tumor | 4.06 ± 2.56 (n = 6) | 7.15 ± 3.38 (n = 6) | 5.80 ± 3.17 (n = 10) | 4.75 ± 2.37 (n = 10) |
| Liver | 3.70 ± 0.909 (n = 6) | 2.19 ± 0.77 (n = 6) | 1.81 ± 0.47 (n = 10) | 1.72 ± 0.41 (n = 10) |
| Kidney | 74.56 ± 16.20 (n = 6) | 94.98 ± 11.96 (n = 6) | 52.97 ± 8.08 (n = 10) | 39.30 ± 7.30 (n = 10) |
| Spleen | 5.96 ± 1.08 (n = 6) | 2.00 ± 0.31 (n = 6) | 0.94 ± 0.26 (n = 10) | 0.69 ± 0.17 (n = 10) |

TABLE 10

Z02465 (SEQ. ID NO. 23) cPn216 in HT29 Tumor Bearing Mice

|  | 5 Minutes | 30 Minutes | 120 Minutes | 240 Minutes |
| --- | --- | --- | --- | --- |
| Blood | 5.06 ± 0.06 (n = 3) | 1.23 ± 0.10 (n = 3) | 0.45 ± 0.06 (n = 7) | 0.32 ± 0.04 (n = 7) |
| Tumor | 2.28 ± 0.26 (n = 3) | 1.74 ± 0.27 (n = 3) | 0.83 ± 0.17 (n = 7) | 0.51 ± 0.18 (n = 7) |
| Liver | 3.60 ± 0.39 (n = 3) | 1.68 ± 0.27 (n = 3) | 1.32 ± 0.17 (n = 7) | 1.58 ± 0.09 (n = 7) |
| Kidney | 96.29 ± 11.43 (n = 3) | 96.08 ± 2.54 (n = 3) | 46.67 ± 4.96 (n = 7) | 44.24 ± 6.90 (n = 7) |
| Spleen | 6.86 ± 0.66 (n = 3) | 1.69 ± 0.48 (n = 3) | 0.85 ± 0.19 (n = 7) | 0.71 ± 0.12 (n = 7) |

Biodistribution: Metabolite Study

Tissue samples were collected from blood, urine, kidney homogenate and tumor homogenate in order to determine the size and composition of the radioactive species present in each at t=5, 30, 60 and 120 minutes post injection. Kidney and Tumor tissues were excised and homogenized by mechanical grinding using a mortar and pestle. Radioactive species were extracted into RIPA buffer with protease inhibitors (Santa Cruz Biotech, Santa Cruz, Calif. #24948) and all samples centrifuged for 5 min. at 10000 rpm. The resulting supernatant was removed and filtered through a 0.2 µm PTFE filter. HPLC injection volumes were determine by net activity present with an 'on column' target activity of 0.5 to 1 µCi.

Four separate tissues were extracted and analyzed for their radioactive content, blood, urine, kidneys and tumor at timepoints 5, 30, 60 and 120 min. ITLC, reverse phase and size exclusion HPLC analysis were performed for each timepoint for filtered and centrifuged tissue homogenate. Blood showed the presence of the injected tracer Z02465 (SEQ. ID NO. 23)-cPn216-$^{99m}$Tc(O)$_2$ with a decreasing signal to noise ratio over time, suggesting slow clearance of the tracer from the blood. Analysis of the radioactive species present in kidney tissue revealed little, if any of the injected tracer with a large proportion of the activity present as lower molecular weight, more hydrophilic compounds. Likewise, urine analysis established that only small, hydrophilic radioactive species infiltrated the urine for excretion. The signal:noise ratio for urine analysis increased with time, illustrating the in vivo accumulation of activity over time, a result consistent with the biodistribution data. Finally, analysis of tumor homogenate showed the presence of radioactive species similar in composition to the injected tracer, but also compounds both larger and smaller in molecular weight. Reverse phase HPLC analysis did give a peak with a similar retention time of the injected tracer.

Polypeptides, F-18-Labeled via Aminoxy Functionality

Z02465 (SEQ. ID NO. 23)-cysteine polypeptide was functionalized with an aminoxy group via an engineered C-terminal cysteine. The purity of the polypeptide molecules provided was determined to be >95% by High Performance Liquid Chromatography (HPLC).

Synthesis of Mal-Aminoxy (Mal-AO)

To incorporate F-18 into the Polypeptide molecules, a bifunctional linker Mal-AO was synthesized consisting of two orthogonal groups: a thiol-reactive maleimide group for conjugation to the engineered cysteine and an F-18-aldehyde-reactive aminoxy group. This linker was prepared by reacting N-(2-aminoethyl)malemide with 2-(tert-butoxycarbonylaminooxy)acetic acid using 1-ethyl-3-[3-dimethylaminopropyl] carbodiimide (EDC)-mediated coupling conditions yielding the Boc-protected form of the linker. The Boc protecting group was then de-protected by acid cleavage to give the final Mal-AO product in quantitative yield. The final product was used directly without further purification.

Dichloromethane, 2-(tert-butoxycarbonylaminooxy) acetic acid, triethylamine, N-(2-aminoethyl)maleimide trifluoroacetic acid (TFA) salt, N-hydroxybenzotriazole hydrate (HOBT), 1-ethyl-3-[3-dimethylaminopropyl]carbodiimide (EDC), dithiothriotol (DTT), and all other standard synthesis reagents were purchased from Sigma-Aldrich Chemical Co. (St. Louis, Mo.). All chemicals were used without further purification. PBS buffer (1×, pH 7.4) was obtained from Invitrogen (Carlsbad, Calif.). HPLC-grade ethyl acetate, hexanes, acetonitrile (CH$_3$CN), trifluoroacetic acid (TFA), and Millipore 18 mΩ water were used for purifications.

Procedure for preparing the bifunctional compound tert-butyl-2-(2-(2,5-dioxo-2,5-dihydro-1H-pyrrol-1-yl)ethylamino)-2-oxoethoxycarbamate (FIG. 23A), abbreviated as "Mal-AO-Boc".

To a solution of 2-(tert-butoxycarbonylaminooxy)acetic acid (382 mg, 2 mmol) in anhydrous dichloromethane (20 mL) was added sequentially triethylamine (307 µL, 2.2 mmol), N-(2-aminoethyl)maleimide-TFA salt (508 mg, 2 mmol), HOBT(306 mg, 2 mmol), and EDC (420 mg, 2.2 mmol). After being stirred for 24 hrs at room temperature, the reaction mixture was diluted with ethyl acetate (50 mL) and washed with saturated sodium bicarbonate solution (3×30 mL), water (30 mL), and brine (30 mL). The organic layer was dried over anhydrous magnesium sulfate and filtered. The filtrate was concentrated to a pale yellow solid, which was purified by column chromatography (70% ethyl acetate in hexanes) to give the product as a white powder (500 mg, 80% yield).

Procedure for preparing the bifunctional compound 2-(aminooxy)-N-(2-(2,5-dioxo-2,5-dihydro-1H-pyrrol-1-yl) ethyl)acetamide hydrochloride (FIG. 23B), abbreviated as "Mal-AO".

A solution of 9.3 mg of Mal-AO-Boc in 1 mL of 3M HCl in methanol was stirred at room temperature for 18 hours. Solvents were removed under vacuum to yield Mal-AO as a light yellow solid.

Bioconjugation of Mal-AO to Polypeptide Molecules

The polypeptide was dissolved with freshly degassed PBS buffer (1×, pH 7.4) at a concentration of approximately 1 mg/mL. The disulfide linkage in the polypeptide was reduced by the addition of dithiothreitol (DTT) solution in freshly degassed PBS buffer (1×, pH 7.4). The final concentration of DTT is 20 mM. The reaction mixture was vortexed for 2 hours and eluted through a Zeba desalt spin column (Pierce Technologies) pre-equilibrated with degassed PBS buffer to remove excess of DTT reagent. The reduced polypeptide was collected, and the bifunctional Mal-AO compound was added (15 equivalents per equivalent of the polypeptide) as a solution in DMSO. After being vortexed at room temperature overnight, the reaction mixture was purified with High Performance Liquid Chromatography (HPLC).

The HPLC purification was performed on a MiCHROM Magic C18AQ 5μ 200A column (MiChrom Bioresources, Auburn, Calif.). Solvent A: H2O (with 0.1% formic acid), Solvent B: $CH_3CN$ (with 0.1% formic acid). Gradient: 5-100% B over 30 mins. The fractions containing desired product was combined and neutralized with 100 mM ammonium bicarbonate solution, and the solvents were removed by lyophilization to give the aminoxy-modified polypeptide as a white solid (62% yield).

ESI-TOF-MS analysis confirmed the presence of target product with the expected molecular weights (calculated MW: 7451 Da, found: 7451 Da for Z02465 (SEQ. ID NO. 23)—ONH2). No byproduct in which 2 ONH$_2$ labels were added to the polypeptide molecules was observed.

Radiolabeling

General: All reactions were performed either under a nitrogen atmosphere or in a crimp-top sealed vial purged with nitrogen. Kryptofix 222 (Aldrich) and $K_2CO_3$ (EMD Science) were purchased and used as received. Optima™-grade acetonitrile was used as both HPLC and reaction solvents.

[F-18]KF (40mCi·$mL^{-1}$ (1480 MBq·$mL^{-1}$) in purified water) was obtained from either IBA Molecular (Albany, N.Y.) or PETNET Solutions (Albany, N.Y.) and used as received. The [F-18]fluoride was first immobilized on a Chromafix 30-PS-HCO$_3$ anion exchange cartridge (ABX, Radeberg, Germany), then eluted into a drydown vessel with a 1 mL, 4:1 mixture of acetonitrile:H$_2$O containing Kryptofix K222 (376 g·$mol^{-1}$, 8 mg, $2.13 \times 10^{-5}$ mol) and potassium carbonate (138.2 g·$mol^{-1}$, 2.1 mg, $1.52 \times 10^{-5}$ mol). The solvent was removed under partial vacuum and a flow of nitrogen with gentle heating (~45° C.) (~15 min). The source vial and anion exchange cartridge were then washed with 0.5 mL of acetonitrile containing K222 (8 mg) and the reaction mixture again brought to dryness under partial vacuum and gentle heating (~10 min). The reaction vessel was repressurized with N$_2$ and the azeotropic drydown repeated once with an additional 0.5 mL of acetonitrile. 4-formyl-N,N,N-trimethylanilinium triflate (313.30 g·$mol^{-1}$, 3.1 mg, $9.89 \times 10^{-6}$ mol) was dissolved in 0.35 mL of anhydrous DMSO (Acros) and added directly to the reaction vessel containing the [F-18]KF·K222, K$_2$CO$_3$. The reaction mixture was heated to 90° C. for 15 min and immediately cooled and quenched with 3 mL of distilled, deionized H$_2$O (ddH$_2$O). This mixture was subsequently passed through a cation exchange cartridge (Waters SepPak Light Accell Plus CM), diluted to 10 mL with ddH$_2$O, and loaded onto a reverse phase C18 SepPak (Waters SepPak Plus C18). The SepPak was flushed with 10 mL of ddH$_2$O then purged with 30 mL of air. [F-18]4-fluorobenzaldehyde ([F-18]FBA), was eluted in 1.0 mL of methanol.

Separately, a high recovery vial (2 mL, National Scientific) was charged with the Z02465-(SEQ. ID NO. 23)-Cys-ONH$_2$ (0.35-0.5 mg). The solid was suspended in 25 μL of ddH$_2$O and 8 μL of trifluoroacetic acid. 25 μL of [F-18]FBA in methanol (see above) was transferred to the reaction vial. The vessel was capped, crimped, placed in a heating block and maintained at 60° C. for 15 minutes; at which point a small aliquot (<5 μL) was removed for analytical HPLC analysis (FIG. 1). 450 μL of ddH$_2$O with 0.1% TFA was used to dilute the solution to approx. 500 μL in preparation for semi-preparative HPLC purification. [F-18]FB-Polypeptide was isolated and purified by semi-preparative HPLC. The HPLC fraction containing the product (0.113 mCi/4.18 MBq) was diluted 5:1 with ddH$_2$O and subsequently immobilized on a tC18 Plus Sep Pak (Waters). The SepPak was flushed first with 5 mL of ddH$_2$O then 30 mL of air. [F-18]FB-Polypeptide (0.073 mCi, 2.70 MBq) was isolated in a minimal amount of ethanol by first eluting the void volume (approx. 0.5 mL) followed by collecting 250 to 300 μL of eluent in a separate flask. RP-HPLC analysis was performed on the isolated product in order to establish radiochemical and chemical purity. Typically, 10 μL of a 0.1 μCi/μL solution was injected for post formulation analysis. Isolated radiochemical yield was 16% (27% decay corrected from addition of [F-18]FBA) and radiochemical purity of >99%. This is illustrated in FIG. 24.

TABLE 11

| Compound | Yield (%) | HPLC RCP (%) |
|---|---|---|
| Z02465 (SEQ. ID NO. 23) | 16% (real) 27% (decay corrected) | >99% |

Analytical HPLC conditions used are as follows: Analysis performed on an HP Agilent 1100 with a G1311A QuatPump, G1313A autoinjector with 100 μL syringe and 2.0 mL seat capillary, Phenomenex Gemini C18 column (4.6 mm×150 mm), 5μ, 100 Å (S/N 420-477-10), G1316A column heater, G1315A DAD and Ramon Star—GABI gamma-detector. 95:5 ddH$_2$O:CH$_3$CN with 0.05% TFA, Solvent B: CH$_3$CN with 0.05% TFA. Gradient elution (1.0 mL·$min^{-1}$): 0 min. 0% B, 1 min. 15% B, 21 min. 50% B, 22 min. 100% B, 26 min. 100% B, 27 min. 0% B, 32 min. 0% B. (TR ~15 min) or Gradient elution (1.2 mL·$min^{-1}$): 0 min. 0% B, 1 min. 15% B, 10 min. 31% B, 10.5 min. 100% B, 13.5 min. 100% B, 14 min. 0% B, 17 min. 0% B. (TR ~13.2 min).

Semipreparative HPLC conditions used are as follows: Purification was performed on a Jasco LC with a DG-2080-54 4-line Degasser, an MX-2080-32 Dynamic Mixer and two PU-2086 Plus Prep pumps, an AS-2055 Plus Intelligent autoinjector with large volume injection kit installed, a Phenomenex 5μ Luna C18(2) 100 Å, 250×10 mm, 5μ, column with guard (S/N 295860-1, P/N 00G-4252-N0), an MD-2055 PDA and a Carroll & Ramsey Associates Model 105S Analogue Ratemeter attached to a solid-state SiPIN photodiode gamma detector. Gradient elution: 0 min. 5% B, 32 min. 20% B, 43 min. 95% B, 46 min. 95% B, 49 min. 5% B, Solvent A: ddH$_2$O:CH$_3$CN with 0.05% TFA, Solvent B: CH$_3$CN with 0.05% TFA (TR ~39.5 min).

Animal Models used to Study F-18-Polypeptide-Aminoxy Conjugates

In vivo studies were carried out with female CD-1 nude mice (Charles River Labs, Hopkinton, Mass.) with an age range between 8 and 15 weeks. Mice were housed in a ventilated rack with food and water ad libitum and a standard 12 hour day-night lighting cycle. For xenografts, animals were injected with 100 ul of cells in a 50/50 v/v mix of matrigel and PBS. Cells were implanted subcutaneously in the left hindquarter. Implantation was performed under isoflurane anesthesia. For HT29 and U87, between $3 \times 10^6$ to $4 \times 10^6$ cells were implanted in each mouse. For M231, $1 \times 10^7$ cells were implanted in each mouse. Under these conditions, useable tumors (100 to 300 ug) were obtained in 3 to 4 weeks in greater than 80% of animals injected.

Biodistribution of Z02465 (SEQ. ID NO. 23)-fluorobenzyl-F-18

Mice were given tail-vein injections of ~1 ug of F-18-labeled polypeptide (~2 uCi/1 ug). Mice were placed in filter-paper lined cages until euthanasia. Three to five mice were euthanized at each timepoint and tissues of interest dissected and counted on a Perkin Elmer Wallac Wizard 1480 Gamma Counter. Data were collected for blood, kidney, liver, spleen, and injection site (tail). Urine from cages was pooled with the bladder and also counted. The remaining tissues were counted and the sum of all tissues plus urine for each animal was summed to provide the total injected dose. The percent injected dose for each organ was determined based on this total, and organs were weighed for determination of the percent injected dose per gram, (% ID/g). Data is reported as mean value for all three mice in the timepoint with error bars representing the standard deviation of the group.

The polypeptides underwent biodistribution studies in U87 cell xenograft models. Four timepoints were taken over four hours (5, 30, 120, and 240 minutes post-injection). Complete biodistribution data are included in table 11 (% ID/g Z02465 (SEQ. ID NO. 23)-fluorobenzyl-F-18 in U87 Tumor Bearing Mice)

FIGS. 26 and 27 shows the tumor, blood, tumor:blood, and clearance curves for these experiments.

The Z02465 (SEQ. ID NO. 23)-fluorobenzyl-F-18 polypeptide shows strong tumor uptake in target-expressing U87 tumors, with a value of 5.53±0.78 (n=5) of the injected dose per gram of tissue at 30 minutes post-injection (PI). Tumor:blood ratios were approximately 5, 10, and 32 at 30, 120, and 240 min post injection, respectively.

The polypeptides exhibit a monoexponential clearance from the blood with half-lives of less than two minutes. This clearance is primarily mediated by the kidneys, with 2.32±0.307 (n=5) ID/organ at 240 min PI. Activity is secreted primarily in the urine. Polypeptide uptake in the spleen was minimal, and low uptake in the liver is observed, ca. 0.5% ID/organ (equivalent in value in mice to % ID/g) over the course of the study (four hours post injection).

TABLE 12

% ID/g Z02465 (SEQ. ID NO. 23)-fluorobenzyl-F-18 in U87 Tumor Bearing Mice

|        | 5 Minutes          | 30 Minutes         | 120 Minutes        | 240 Minutes          |
|--------|--------------------|--------------------|--------------------|----------------------|
| Blood  | 7.31 ± 0.15 (n = 3) | 1.20 ± 0.15 (n = 5) | 0.55 ± 0.30 (n = 5) | 0.062 ± 0.027 (n = 5) |
| Tumor  | 3.53 ± 0.64 (n = 3) | 5.53 ± 0.78 (n = 5) | 3.95 ± 0.53 (n = 5) | 1.82 ± 0.50 (n = 5)  |
| Liver  | 3.32 ± 0.08 (n = 3) | 2.14 ± 0.29 (n = 5) | 0.91 ± 0.42 (n = 5) | 0.50 ± 0.15 (n = 5)  |
| Kidney | 95.90 ± 27.62 (n = 3) | 24.99 ± 1.95 (n = 5) | 4.93 ± 1.10 (n = 5) | 2.32 ± 0.31 (n = 5) |
| Spleen | 2.79 ± 0.34 (n = 5) | 1.35 ± 0.25 (n = 5) | 0.53 ± 0.10 (n = 5) | 0.24 ± 0.09 (n = 5)  |

Iodine(I)-Radiolabeling of Polypeptides

All reactions are performed either under a nitrogen atmosphere or in a crimp-top sealed vial purged with nitrogen. Optima™-grade acetonitrile is used as both HPLC and reaction solvents.

[$^{123}$I]4-iodobenzaldehyde ([$^{123}$I]IBA) is added to a high recovery vial (2 mL, National Scientific) containing the polypeptide-ONH$_2$ (Z02465, SEQ. ID NO 23), 0.35-0.5 mg). The reaction commences by dissolving the polypeptide in 25 μL of ddH$_2$O and adding 8 μL of trifluoroacetic acid followed by the addition of IBA in methanol. The vessel is capped, crimped, placed in a heating block and maintained at 60° C. for 15 minutes; removing a small aliquot (<5 μL) for analytical HPLC analysis is done to assess the status of the reaction. The reaction mixture is diluted to a minimum 1:1 mixture of ddH$_2$O:Acetonitrile mixture containing 0.1% TFA in preparation for semi-preparative HPLC purification. [$^{123}$I]IB-Polypeptide is isolated and purified by semi-preparative HPLC or NAP5 size exclusion chromatography. The HPLC fraction containing the product is further diluted (5:1) with ddH2O and subsequently immobilized on a tC18 Plus Sep Pak (Waters). Flushing the SepPak first with 5 mL of ddH2O then 30 mL of air gives the [$^{123}$I]IB-Polypeptide in a minimal amount of ethanol by first eluting the void volume (approx. 0.5 mL) followed by collecting 250 to 300 μL of eluent in a separate flask. RP-HPLC analysis is performed on the isolated product to establish radiochemical and chemical purity.

Gadolinium (Gd) Radiolabeling of Polypeptides

Polypeptide Z2465 (SEQ. ID 16) was labeled with Gd, specifically Gd-153, after a DOTA (1,4,7,10-tetraazacyclododecane-N,N',N,N'''-tetraacetic acid) chelator was conjugated to the polypeptide.

Bioconjugation of Mal-DOTA to polypeptide molecules were accomplished as follows. The polypeptide was dissolved with freshly degassed PBS buffer (1×, pH 7.4) at a concentration of approximately 1 mg/mL. The disulfide linkage in the polypeptide was reduced by the addition of DTT solution in freshly degassed PBS buffer (1×, pH 7.4). The final concentration of DTT was 20 mM. The reaction mixture was vortexed for 2 hours and passed through a Zeba desalt spin column (Pierce Technologies) pre-equilibrated with degassed PBS buffer (1×, pH 7.4) to remove excess of DTT reagent. The eluted reduced polypeptide molecule was collected, and the bifunctional compound mal-DOTA was added (15 quivalents per equivalent of the polypeptide) as a solution in DMSO, and the mixture was vortexed at room temperature. The reaction was allowed to proceed allowed to proceed overnight to ensure the complete conversion of the polypeptide molecules.

The HPLC purification was performed on a MiCHROM Magic C18AQ 5□ 200A column (MiChrom Bioresources, Auburn, Calif.). Solvent A: H2O (with 0.1% formic acid), Solvent B: CH$_3$CN (with 0.1% formic acid). Gradient: 5-100% B over 30 mins.

The fractions containing desired product were combined and neutralized with 100 mM ammonium bicarbonate solution, and the solvents were removed by lyophilization to give the conjugated polypeptide as a white solid.

LC-MS analysis of the purified product confirmed the presence of the desired product, and the MW suggested that only one DOTA chelator was added to the polypeptide construct (calculated MW: 8587 Da, found: 8588 Da for Z2465 (SEQ. ID NO. 16)-DOTA).

Radiolabeling was subsequently accomplished as follows: 10 μl ammonium acetate solution (pH=6.75) was added to a screw top vial followed by 9511 of $^{153}$GdCl$_3$ (Perkin Elmer) (4.1 MBq) in 0.1M HCl. 400 μg of the Z2465 (SEQ. ID NO. 16)-DOTA Polypeptide (MW=8587 g·mol$^{-1}$, 4.7×10$^{-8}$ mol) in 50 μl H$_2$O was then added to the reaction mixture to give a final Z2465 (SEQ. ID NO. 16)-DOTA concentration of 0.3 mM and a pH of 4.5. The reaction vial was sealed and the reaction maintained at ambient temperature. Reverse phase HPLC analysis of the crude reaction mixture determined the radiochemical purity of the Ga-67-NOTA Her2 Polypeptide to be 64% after 9 days (FIG. 29). The Z2465 (SEQ. ID NO. 16)-DOTA Polypeptide was purified by HPLC giving 0.065 mCi (2.4 MBq) of Z2465 (SEQ. ID NO. 16)-DOTA (yield=57%). HPLC solvents were removed under vacuum giving a final solution containing approximately 0.6 mL of solvent remaining. Approximately 0.9 mL of 50 mM phosphate buffered saline was then added to give a final solution at pH 7 with a final concentration of 0.043 mCi/mL (1.6 MBq/mL). Purified, formulated Z2465 (SEQ. ID NO. 16)-DOTA Polypeptide was found to be stable for at least 43 days when stored at −70° C. (FIG. 30.)

Analytical HPLC conditions used are as follows: Column: Grace Vydac C4 protein 5 micron, 300 Å, 4.6×250 mm. Solvent A=95/5H$_2$O/CH$_3$CN in 0.05% trifluoroacetic acid (TFA). Solvent B=95/5 CH$_3$CN/H$_2$O in 0.05% TFA. HPLC gradient: 0 min, 0% B; 4 min, 20% B; 16 min, 60% B; 20 min, 100% B; 25 min, 100% B; 26 min, 0% B.

Semi-preparative HPLC conditions used are as follows: Column: Grace Vydac C4 protein 5 micron, 300 Å, 4.6×250 mm. Solvent A=95/5H$_2$O/CH$_3$CN in 0.05% trifluoroacetic acid (TFA). Solvent B=95/5 CH$_3$CN/H$_2$O in 0.05% TFA. HPLC gradient: 0 min, 0% B; 4 min, 20% B; 16 min, 60% B; 20 min, 100% B; 25 min, 100% B; 26 min, 0% B.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore intended to be embraced therein.

The invention claimed is:

1. A PDGF-Rβ imaging agent comprising a polypeptide comprising the amino acid sequence selected from the group consisting of SEQ ID NOS: 1, 2, 3, 4, 5, 6, 7, 8, 9; wherein the peptide is labeled with a signal generator; and wherein the polypeptide binds specifically to PDGF-Rβ-.

2. The imaging agent of claim 1, wherein polypeptide has a binding affinity of at least 10 nM to PDGFR-β expressed by A772 cells, U87 cells or M231 cells.

3. The imaging agent of claim 1, wherein the signal generator comprises a paramagnetic label, a radionuclide, or a fluorophore.

4. The imaging agent of claim 1, further comprising a multivalent polypeptide comprising at least two amino acid sequences selected from the group consisting of SEQ ID NOS: 1, 2, 3, 4, 5, 6, 7, 8, 9.

5. The imaging agent of claim 4, wherein the multivalent polypeptide includes two repeated amino acid sequences having greater than 90% sequence identity to produce a divalent homogenous polypeptide.

6. The imaging agent of claim 1, wherein the signal generator is an radionuclide is selected from fluorine, iodine, technechium, gallium, or gadolinium.

7. The imaging agent of claim 6, wherein the fluorine comprises $^{18}$F.

8. The imaging agent of claim 6, wherein the $^{18}$F is attached to the polypeptide via an aminoxy linker.

9. The imaging agent of claim 6, wherein the $^{18}$F is attached to the polypeptide via an aminoxy linker at the N-terminus of the polypeptide.

10. The imaging agent of claim 6, wherein the iodine comprises $^{123}$I.

11. The imaging agent of claim 10, wherein the $^{123}$I is attached to the polypeptide via an aminoxy linker.

12. The imaging agent of claim 10, wherein the $^{123}$I is attached to the polypeptide via an aminoxy linker at the N-terminus of the polypeptide.

13. The imaging agent of claim 10, wherein the technecium comprises $^{99m}$Tc.

14. The imaging agent of claim 13, wherein the $^{99m}$Tc is attached to the polypeptide via an PN linker.

15. The imaging agent of claim 14, wherein the PN linker comprises CPN216.

16. The imaging agent of claim 14, wherein the $^{99m}$Tc is attached to the polypeptide via a PN linker at the N-terminus of the polypeptide.

17. The imaging agent of claim 3, wherein the signal generator is a paramagnetic label selected from $^{157}$Gd, $^{55}$Mn, $^{162}$Dy, $^{52}$Cr, and $^{56}$Fe.

18. The imaging agent of claim 17, wherein the paramagnetic label is attached to the polypeptide via a chelator selected from NOTA, DOTA, DTPA.

19. The imaging agent of claim 6, wherein the radionuclide is comprised of $^1$Gd-153 or Ga-67, Co-55, Co-57, Cu-64, Cu-67, Zr-89, Y-86.

20. The imaging agent of claim 19, wherein the radionuclide label is attached to the polypeptide via a chelator selected from NOTA, DOTA, DTPA.

21. A method of imaging a PDGF-R-associated disease condition in a mammal comprising introducing into the mammal a polypeptide comprising the amino acid sequence selected from the group consisting of SEQ ID NOS: 1, 2, 3, 4, 5, 6, 7, 8, 9 or a conservative variant thereof labeled with a signal generator, wherein the polypeptide binds specifically to PDGF-Rβ-, permitting the agent to migrate to the disease tissue, and image the diseased tissue.

22. The method of claim 21, wherein the mammal is a human.

23. The method of claim 21, wherein the PDGF-Rβ-associated disease condition is liver fibrosis, cirrhosis, or abnormal liver function or a combination thereof.

24. The method of claim 21, wherein the imaging method is selected from PET, SPECT, MRI, radioimaging, and optical imaging.

25. The method of claim 21, further comprising treating the mammal before, after, or before and after imaging, and using the results of the imaging step to manage the disease condition.

26. The method of claim 21, wherein the agent is dispersed in a pharmaceutically acceptable solution with a pH of about 6 to about 8.

* * * * *

SEQUENCE LISTING

```
<160> NUMBER OF SEQ ID NOS: 26

<210> SEQ ID NO 1
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Lys Glu Arg Gln Val Ala Ala Ala Glu Ile Asp Ala Leu Pro Asn Leu
1               5                   10                  15

Asn Arg Gly Gln Trp Asn Ala Phe Ile Ala Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 2
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Lys Glu Leu Ser Asp Ala Ala Gln Glu Ile Asp Ser Leu Pro Asn Leu
1               5                   10                  15

Asn Arg Ser Gln Trp Asn Ala Phe Ile Lys Ser Leu Ile Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 3
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3
```

```
Lys Glu Arg Arg Glu Ala Ala Lys Glu Ile Asp Ser Leu Pro Asn Leu
1               5                   10                  15

Asn Arg Thr Gln Trp Asn Ala Phe Ile Arg Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 4
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Lys Glu Leu Val Arg Ala Ala Gln Glu Ile Asp Glu Leu Pro Asn Leu
1               5                   10                  15

Asn Arg Gly Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 5
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Lys Glu Leu Ile Ala Ala Ala Ala Glu Ile Asp Arg Leu Pro Asn Leu
1               5                   10                  15

Asn Arg Val Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 6
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Lys Glu Leu Ile Glu Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 7
```

```
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Lys Glu Leu Val Arg Ala Ala Glu Glu Ile Asp Asn Leu Pro Asn Leu
1               5                   10                  15

Asn Arg Lys Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 8
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Lys Glu Leu Val Lys Ala Ala Ala Glu Ile Asp Ala Leu Pro Asn Leu
1               5                   10                  15

Asn Arg Arg Gln Trp Asn Ala Phe Ile Lys Ser Leu Val Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 9
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Lys Glu Leu Ile Glu Ala Ala Ala Glu Ile Asp Ala Leu Pro Asn Leu
1               5                   10                  15

Thr Arg Arg Gln Trp Asn Ala Phe Ile Lys Lys Leu Val Asp Asp Pro
            20                  25                  30

Ser Gln Ser Ser Glu Leu Leu Ser Glu Ala Lys Lys Leu Asn Asp Ser
        35                  40                  45

Gln

<210> SEQ ID NO 10
<211> LENGTH: 74
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Gly Ser Ser His His His His His His Tyr Tyr Leu Glu Val Asp Asn
1               5                   10                  15

Lys Phe Asn Lys Glu Leu Gly Trp Ala Thr Trp Glu Ile Phe Asn Leu
            20                  25                  30
```

Pro Asn Leu Asn Gly Val Gln Val Lys Ala Phe Ile Asp Ser Leu Arg
            35                  40                  45

Asp Asp Pro Ser Gln Ser Ala Asn Leu Leu Ala Glu Ala Lys Lys Leu
50                      55                  60

Asn Asp Ala Gln Ala Pro Lys Val Asp Cys
65                  70

<210> SEQ ID NO 11
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Gly Ser Ser His His His His His His Leu Gln Val Asp Asn Lys Phe
1               5                   10                  15

Asn Lys Glu Arg Gln Val Ala Ala Ala Glu Ile Asp Ala Leu Pro Asn
            20                  25                  30

Leu Asn Arg Gly Gln Trp Asn Ala Phe Ile Ala Ser Leu Val Asp Asp
            35                  40                  45

Pro Ser Gln Ser Ala Asn Leu Leu Ala Glu Ala Lys Lys Leu Asn Asp
50                      55                  60

Ala Gln Ala Pro Lys Val Asp Cys
65                  70

<210> SEQ ID NO 12
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Gly Ser Ser His His His His His His Leu Gln Val Asp Asn Lys Phe
1               5                   10                  15

Asn Lys Glu Leu Ser Asp Ala Ala Gln Glu Ile Asp Ser Leu Pro Asn
            20                  25                  30

Leu Asn Arg Ser Gln Trp Asn Ala Phe Ile Lys Ser Leu Ile Asp Asp
            35                  40                  45

Pro Ser Gln Ser Ala Asn Leu Leu Ala Glu Ala Lys Lys Leu Asn Asp
50                      55                  60

Ala Gln Ala Pro Lys Val Asp Cys
65                  70

<210> SEQ ID NO 13
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gly Ser Ser His His His His His His Leu Gln Val Asp Asn Lys Phe
1               5                   10                  15

Asn Lys Glu Arg Arg Glu Ala Ala Lys Glu Ile Asp Ser Leu Pro Asn
            20                  25                  30

Leu Asn Arg Thr Gln Trp Asn Ala Phe Ile Arg Ser Leu Ala Asp Asp

```
                      35                  40                  45

Pro Ser Gln Ser Ala Asn Leu Leu Ala Glu Ala Lys Lys Leu Asn Asp
 50                  55                  60

Ala Gln Ala Pro Lys Val Asp Cys
 65                  70

<210> SEQ ID NO 14
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gly Ser Ser His His His His His His Leu Gln Val Asp Asn Lys Phe
 1               5                  10                  15

Asn Lys Glu Leu Val Arg Ala Ala Gln Glu Ile Asp Glu Leu Pro Asn
                20                  25                  30

Leu Asn Arg Gly Gln Trp Asn Ala Phe Ile Lys Ser Leu Val Asp Asp
            35                  40                  45

Pro Ser Gln Ser Ala Asn Leu Leu Ala Glu Ala Lys Lys Leu Asn Asp
 50                  55                  60

Ala Gln Ala Pro Lys Val Asp Cys
 65                  70

<210> SEQ ID NO 15
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gly Ser Ser His His His His His His Leu Gln Val Asp Asn Lys Phe
 1               5                  10                  15

Asn Lys Glu Arg Leu Lys Ala Ala Ala Glu Ile Asp Ala Leu Pro Asn
                20                  25                  30

Leu Asn Arg Lys Gln Trp Asn Ala Phe Ile Ser Ser Leu Arg Asp Asp
            35                  40                  45

Pro Ser Gln Ser Ala Asn Leu Leu Ala Glu Ala Lys Lys Leu Asn Asp
 50                  55                  60

Ala Gln Ala Pro Lys Val Asp Cys
 65                  70

<210> SEQ ID NO 16
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Gly Ser Ser His His His His His His Leu Gln Val Asp Asn Lys Phe
 1               5                  10                  15

Asn Lys Glu Leu Ile Glu Ala Ala Ala Glu Ile Asp Ala Leu Pro Asn
                20                  25                  30

Leu Asn Arg Arg Gln Trp Asn Ala Phe Ile Lys Ser Leu Val Asp Asp
            35                  40                  45
```

```
Pro Ser Gln Ser Ala Asn Leu Leu Ala Glu Ala Lys Lys Leu Asn Asp
 50                  55                  60

Ala Gln Ala Pro Lys Val Asp Cys
 65                  70
```

<210> SEQ ID NO 17
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Gly Ser Ser His His His His His His Leu Gln Val Asp Asn Lys Phe
 1               5                  10                  15

Asn Lys Glu Leu Val Arg Ala Ala Glu Ile Asp Asn Leu Pro Asn
             20                  25                  30

Leu Asn Arg Lys Gln Trp Asn Ala Phe Ile Lys Ser Leu Val Asp Asp
             35                  40                  45

Pro Ser Gln Ser Ala Asn Leu Leu Ala Glu Ala Lys Lys Leu Asn Asp
 50                  55                  60

Ala Gln Ala Pro Lys Val Asp Cys
 65                  70
```

<210> SEQ ID NO 18
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Gly Ser Ser His His His His His His Leu Gln Val Asp Asn Lys Phe
 1               5                  10                  15

Asn Lys Glu Leu Val Lys Ala Ala Glu Ile Asp Ala Leu Pro Asn
             20                  25                  30

Leu Asn Arg Arg Gln Trp Asn Ala Phe Ile Lys Ser Leu Val Asp Asp
             35                  40                  45

Pro Ser Gln Ser Ala Asn Leu Leu Ala Glu Ala Lys Lys Leu Asn Asp
 50                  55                  60

Ala Gln Ala Pro Lys Val Asp Cys
 65                  70
```

<210> SEQ ID NO 19
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Gly Ser Ser His His His His His His Leu Gln Val Asp Asn Lys Phe
 1               5                  10                  15

Asn Lys Glu Leu Ile Glu Ala Ala Ala Glu Ile Asp Ala Leu Pro Asn
             20                  25                  30

Leu Asn Arg Arg Gln Trp Asn Ala Phe Ile Lys Ser Leu Val Asp Asp
             35                  40                  45

Pro Ser Gln Ser Ala Asn Leu Leu Ala Glu Ala Lys Lys Leu Asn Asp
 50                  55                  60
```

```
Ala Gln Ala Pro Lys Val Asp Asn Lys Phe Asn Lys Glu Leu Ile Glu
 65                  70                  75                  80

Ala Ala Ala Glu Ile Asp Ala Leu Pro Asn Leu Asn Arg Arg Gln Trp
                 85                  90                  95

Asn Ala Phe Ile Lys Ser Leu Val Asp Asp Pro Ser Gln Ser Ala Asn
            100                 105                 110

Leu Leu Ala Glu Ala Lys Lys Leu Asn Asp Ala Gln Ala Pro Lys Val
        115                 120                 125

Asp Cys
    130

<210> SEQ ID NO 20
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gly Ser Ser His His His His His His Leu Gln Val Asp Asn Lys Phe
 1               5                  10                  15

Asn Lys Glu Leu Val Arg Ala Ala Glu Ile Asp Asn Leu Pro Asn
             20                  25                  30

Leu Asn Arg Lys Gln Trp Asn Ala Phe Ile Lys Ser Leu Val Asp Asp
         35                  40                  45

Pro Ser Gln Ser Ala Asn Leu Leu Ala Glu Ala Lys Lys Leu Asn Asp
     50                  55                  60

Ala Gln Ala Pro Lys Val Asp Asn Lys Phe Asn Lys Glu Leu Val Arg
 65                  70                  75                  80

Ala Ala Glu Glu Ile Asp Asn Leu Pro Asn Leu Asn Arg Lys Gln Trp
                 85                  90                  95

Asn Ala Phe Ile Lys Ser Leu Val Asp Asp Pro Ser Gln Ser Ala Asn
            100                 105                 110

Leu Leu Ala Glu Ala Lys Lys Leu Asn Asp Ala Gln Ala Pro Lys Val
        115                 120                 125

Asp Cys
    130

<210> SEQ ID NO 21
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Gly Ser Ser His His His His His His Leu Gln Val Asp Asn Lys Phe
 1               5                  10                  15

Asn Lys Glu Leu Val Lys Ala Ala Glu Ile Asp Ala Leu Pro Asn
             20                  25                  30

Leu Asn Arg Arg Gln Trp Asn Ala Phe Ile Lys Ser Leu Val Asp Asp
         35                  40                  45

Pro Ser Gln Ser Ala Asn Leu Leu Ala Glu Ala Lys Lys Leu Asn Asp
     50                  55                  60

Ala Gln Ala Pro Lys Val Asp Asn Lys Phe Asn Lys Glu Leu Val Lys
 65                  70                  75                  80
```

```
Ala Ala Ala Glu Ile Asp Ala Leu Pro Asn Leu Asn Arg Arg Gln Trp
                85                  90                  95
Asn Ala Phe Ile Lys Ser Leu Val Asp Asp Pro Ser Gln Ser Ala Asn
            100                 105                 110
Leu Leu Ala Glu Ala Lys Lys Leu Asn Asp Ala Gln Ala Pro Lys Val
        115                 120                 125
Asp Cys
    130
```

<210> SEQ ID NO 22
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Gly Ser Ser His His His His His His Leu Gln Val Asp Asn Lys Phe
1               5                   10                  15
Asn Lys Glu Leu Ile Ala Ala Ala Glu Ile Asp Arg Leu Pro Asn
            20                  25                  30
Leu Asn Arg Val Gln Trp Asn Ala Phe Ile Lys Ser Leu Val Asp Asp
        35                  40                  45
Pro Ser Gln Ser Ala Asn Leu Ala Glu Ala Lys Lys Leu Asn Asp
    50                  55                  60
Ala Gln Ala Pro Lys Val Asp Asn Lys Phe Asn Lys Glu Leu Ile Ala
65                  70                  75                  80
Ala Ala Glu Ile Asp Arg Leu Pro Asn Leu Asn Arg Val Gln Trp
                85                  90                  95
Asn Ala Phe Ile Lys Ser Leu Val Asp Asp Pro Ser Gln Ser Ala Asn
            100                 105                 110
Leu Leu Ala Glu Ala Lys Lys Leu Asn Asp Ala Gln Ala Pro Lys Val
        115                 120                 125
Asp Cys
    130
```

<210> SEQ ID NO 23
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Gly Ser Ser Leu Gln Val Asp Asn Lys Phe Asn Lys Glu Leu Ile Glu
1               5                   10                  15
Ala Ala Ala Glu Ile Asp Ala Leu Pro Asn Leu Asn Arg Arg Gln Trp
            20                  25                  30
Asn Ala Phe Ile Lys Ser Leu Val Asp Asp Pro Ser Gln Ser Ala Asn
        35                  40                  45
Leu Leu Ala Glu Ala Lys Lys Leu Asn Asp Ala Gln Ala Pro Lys Val
    50                  55                  60
Asp Cys
65
```

<210> SEQ ID NO 24
<211> LENGTH: 59
<212> TYPE: PRT

```
-continued

<213> ORGANISM: Artificial Sequence
<220> FEATURE:
<223> OTHER INFORMATION: Description of Artificial Sequence: Synthetic
      polypeptide

<400> SEQUENCE: 24

Ala Glu Ala Lys Tyr Ala Lys Glu Leu Ile Glu Ala Ala Ala Glu Ile
1               5                   10                  15

Asp Ala Leu Pro Asn Leu Thr Arg Arg Gln Trp Asn Ala Phe Ile Lys
            20                  25                  30

Lys Leu Val Asp Asp Pro Ser Gln Ser Ser Glu Leu Leu Ser Glu Ala
        35                  40                  45

Lys Lys Leu Asn Asp Ser Gln Ala Pro Ser Cys
    50                  55

<210> SEQ ID NO 25
<211> LENGTH: 72
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gly Ser Ser His His His His His His Leu Gln Val Asp Asn Lys Phe
1               5                   10                  15

Asn Lys Glu Leu Ile Ala Ala Ala Glu Ile Asp Arg Leu Pro Asn
            20                  25                  30

Leu Asn Arg Val Gln Trp Asn Ala Phe Ile Lys Ser Leu Val Asp Asp
        35                  40                  45

Pro Ser Gln Ser Ala Asn Leu Leu Ala Glu Ala Lys Lys Leu Asn Asp
    50                  55                  60

Ala Gln Ala Pro Lys Val Asp Cys
65                  70

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 26

His His His His His His
1               5
```